United States Patent
Emi et al.

(10) Patent No.: US 9,353,416 B2
(45) Date of Patent: May 31, 2016

(54) GENE RELATING TO ESTIMATION OF POSTOPERATIVE PROGNOSIS FOR BREAST CANCER

(71) Applicants: MITSUBISHI RAYON CO., LTD, Tokyo (JP); NIPPON MEDICAL SCHOOL, Tokyo (JP)

(72) Inventors: Mitsuru Emi, Tokyo (JP); Masamitsu Onda, Tokyo (JP); Hisaki Nagai, Tokyo (JP)

(73) Assignees: Mitsubishi Rayon Co., Ltd., Tokyo (JP); Nippon Medical School, Tokyo (JP)

( * ) Notice: Subject to any disclaimer, the term of this patent is extended or adjusted under 35 U.S.C. 154(b) by 0 days.

(21) Appl. No.: 13/737,349

(22) Filed: Jan. 9, 2013

(65) Prior Publication Data

US 2013/0203621 A1    Aug. 8, 2013

Related U.S. Application Data

(62) Division of application No. 12/785,213, filed on May 21, 2010, now abandoned, which is a division of application No. 10/590,219, filed as application No. PCT/JP2004/012455 on Aug. 24, 2004, now abandoned.

(30) Foreign Application Priority Data

Feb. 24, 2004 (JP) ................................. 2004-048593

(51) Int. Cl.
  *C12Q 1/68* (2006.01)
  *G01N 33/574* (2006.01)

(52) U.S. Cl.
  CPC ........ *C12Q 1/6886* (2013.01); *G01N 33/57415* (2013.01); *C12Q 2600/118* (2013.01)

(58) Field of Classification Search
  None
  See application file for complete search history.

(56) References Cited

U.S. PATENT DOCUMENTS

| | | | | |
|---|---|---|---|---|
| 6,258,540 B1* | 7/2001 | Lo | ......................... | C12Q 1/6879 435/440 |
| 6,355,623 B2* | 3/2002 | Seidman | ................ | A61K 31/52 514/263.4 |
| 2001/0041339 A1 | 11/2001 | Anderson et al. | | |
| 2003/0087251 A1 | 5/2003 | Kurn | | |
| 2008/0026950 A1* | 1/2008 | Emi | ..................... | C12Q 1/6886 506/9 |

FOREIGN PATENT DOCUMENTS

WO    WO 02/46467 A2    6/2002

OTHER PUBLICATIONS

UniGene entry Hs.94653 has been retired (http://www.ncbi.nlm.nih.gov/UniGene/clust.cgi?UGID=141679&TAXID=0&SEARCH=hs.94653, downloaded Jul. 24, 2014).*
NCBI Blast:dbj| AB011179.1| (http://blast.ncbi.nlm.nih.gov/Blast.cgi Jul. 24, 2014.*
UniGene entry Hs.5002/has been retired (http://www.ncbi.nlm.nih.gov/UniGene/clust.cgi?UGID=131599&TAXID=0&SEARCH=hs.5002, downloaded Jul. 24, 2014).*
D67025 (*Homo sapiens* mRNA for proteasome subunit p58, complete cds, Dec. 2, 1997.*
Proteasome (prosome, macropain) 26S subunit, non-ATPase, 3 (PSMD3) (UniGene http://www.ncbi.nlm.nih.gov/UniGene/clust.cgi?UGID=133044&TAXID=9606&SEARCH=d67025, Jul. 24, 2014).*
NCBI Blast:dbj| D67025.1|( http://blast.ncbi.nlm.nih.gov/Blast.cgi, Jul. 24, 2014).*
UniGene entry Hs. 4864/has been retired (http://www.ncbi.nlm.nih.gov/UniGene/clust.cgi?UGID=755122&TAXID=0&SEARCH=hs.4864, downloaded Jul. 24, 2014).*
UniGene entry Hs.06326/has been retired (http://www.ncbi.nlm.nih.gov/UniGene/clust.cgi?UGID=844484&TAXID=0&SEARCH=hs.106326, downloaded Jul. 24, 2014).*
Pritzker (Clinical Chemistry, 2002, 48:1147-1150).*
Adlard et al. (The Lancet Oncology, Feb. 2002, 3:75-82).*
NCBI/ Primer-BLAST: (http://www.ncbi.nlm.nih.gov/tools/primer-blast/ Sep. 22, 2015).*
Chu, Mon-li et al., "Isolation of cDNA and Genomic Clones Encoding Human pro-alpha1(III) Collagen", Partial Characterization of the 3' End Region of The Gene, vol. 260, No. 7, pp. 4357-4363, 1985.
Van De Vijver, Marc J. et al., "A Gene-Expression Signature as a Predictor of Survival in Breast Cancer", The New England Journal of Medicine, vol. 347, No. 25, pp. 1999-2009, 2002.
Nagahata, Takemitsu et al., "Expression Profiling to Predict Postoperative Prognosis for Estrogen Receptor-Negative Breast Cancers by Analysis of 25,344 Genes on a cDNA Microaray", Cancer Sci., vol. 95, No. 3, pp. 218-225, 2004.
Mackay, et al, (Oncogene May 1, 2003, 22: 2680-8).
Soares, et al. (GenBank: AI066764.1, ov25h01.x1, Aug. 13, 1998).
Couraud, et al (NM_002305,galectin-1, LGALS Mar. 1, 1999).

(Continued)

*Primary Examiner* — Peter J Reddig
(74) *Attorney, Agent, or Firm* — Oblon, McClelland, Maier & Neustadt, L.L.P.

(57) ABSTRACT

It is intended to provide a system of predicting the postoperative prognosis in a patient with breast cancer from the viewpoint of gene expression based on the data obtained by genome-wide and comprehensive analysis on gene expression in breast cancer. Expression of human genes is comprehensively analyzed by using a DNA microarray and gene expression functions in various breast cancer conditions are compared, thereby establishing a system of predicting the postoperative prognosis of breast cancer.

9 Claims, 11 Drawing Sheets

(3 of 11 Drawing Sheet(s) Filed in Color)

(56) References Cited

OTHER PUBLICATIONS

Ross and Fletcher (The Oncologist 1998-3:237-252.
Human mRNA for pro-alpha-1 type 3 Collagen. [online]. [retrieved on Sep. 17, 2010]. Retrieved from the Internet: <http://www.ncbi.nlm.nih.gov/sviewer/viewer.fcgi?val=30057&sat=OLDID&satkey=18987>., Aug. 4, 1992, 3 pages.
Masamitsu Onda, et al., "Potentials of Genes Indentified through Microarray Analyses as Markers for Breast Cancer Prognosis", J. Nippon Med. Sch., 2003, 70(6), p. 593, P-60 with English translation.
Mitsuru Emi, et al., "Estimation of Postoperative Prognosis for Breast Cancer by Systemic Expression Analysis Using cDNA Microarray", J. Nippon Med. Sch., 2002, 69(6), p. 658, P-79 with English translation.
Takemitsu Nagahata, et al., "DNA-RNA Based Diagnosis of Postoperative Prognosis for Breast Cancer", Japan Society of Clinical Oncology, 2002, vol. 37, No. 2, p. 182, Sp3-1 with English translation.
Office Action issued Sep. 30, 2010, in Japanese Patent Application No. 2004-318585 (with English translation).

* cited by examiner

FIG. 9
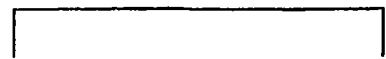

SEQUENCE LISTING

<160> NUMBER OF SEQ ID NOS: 181

<210> SEQ ID NO 1
<211> LENGTH: 19

```
<212> TYPE: DNA
<213> ORGANISM: Artificial Sequence
<220> FEATURE:
<223> OTHER INFORMATION: Synthetic DNA

<400> SEQUENCE: 1
ggaaggtgaa ggtcggagt                                           19

<210> SEQ ID NO 2
<211> LENGTH: 20
<212> TYPE: DNA
<213> ORGANISM: Artificial Sequence
<220> FEATURE:
<223> OTHER INFORMATION: Synthetic DNA

<400> SEQUENCE: 2
tgggtggaat catattggaa                                          20

<210> SEQ ID NO 3
<211> LENGTH: 23
<212> TYPE: DNA
<213> ORGANISM: Artificial Sequence
<220> FEATURE:
<223> OTHER INFORMATION: Synthetic DNA

<400> SEQUENCE: 3
acacttcatc tgctccctca tag                                      23

<210> SEQ ID NO 4
<211> LENGTH: 23
<212> TYPE: DNA
<213> ORGANISM: Artificial Sequence
<220> FEATURE:
<223> OTHER INFORMATION: Synthetic DNA

<400> SEQUENCE: 4
ctgcctagac ctgaggactg tag                                      23

<210> SEQ ID NO 5
<211> LENGTH: 21
<212> TYPE: DNA
<213> ORGANISM: Artificial Sequence
<220> FEATURE:
<223> OTHER INFORMATION: Synthetic DNA

<400> SEQUENCE: 5
actgaggcct tttggtagtc g                                        21

<210> SEQ ID NO 6
<211> LENGTH: 24
<212> TYPE: DNA
<213> ORGANISM: Artificial Sequence
<220> FEATURE:
<223> OTHER INFORMATION: Synthetic DNA

<400> SEQUENCE: 6
tctctttatt gtgatgctca gtgg                                     24

<210> SEQ ID NO 7
<211> LENGTH: 23
<212> TYPE: DNA
<213> ORGANISM: Artificial Sequence
<220> FEATURE:
<223> OTHER INFORMATION: Synthetic DNA

<400> SEQUENCE: 7
```
aaatccttct cgtgtgttga ctg                                                   23

<210> SEQ ID NO 8
<211> LENGTH: 23
<212> TYPE: DNA
<213> ORGANISM: Artificial Sequence
<220> FEATURE:
<223> OTHER INFORMATION: Synthetic DNA

<400> SEQUENCE: 8
cagtcatgag ggctaaaaac tga                                                   23

<210> SEQ ID NO 9
<211> LENGTH: 22
<212> TYPE: DNA
<213> ORGANISM: Artificial Sequence
<220> FEATURE:
<223> OTHER INFORMATION: Synthetic DNA

<400> SEQUENCE: 9
gaagacaaca agttttaccg gg                                                    22

<210> SEQ ID NO 10
<211> LENGTH: 22
<212> TYPE: DNA
<213> ORGANISM: Artificial Sequence
<220> FEATURE:
<223> OTHER INFORMATION: Synthetic DNA

<400> SEQUENCE: 10 atggtttat tgacggcaga ag                                                     22

<210> SEQ ID NO 11
<211> LENGTH: 22
<212> TYPE: DNA
<213> ORGANISM: Artificial Sequence
<220> FEATURE:
<223> OTHER INFORMATION: Synthetic DNA

<400> SEQUENCE: 11
aggacacgtc ctctcctctc tc                                                    22

<210> SEQ ID NO 12
<211> LENGTH: 23
<212> TYPE: DNA
<213> ORGANISM: Artificial Sequence
<220> FEATURE:
<223> OTHER INFORMATION: Synthetic DNA

<400> SEQUENCE: 12
taaagctagc gaaggaacgt aca                                                   23

<210> SEQ ID NO 13
<211> LENGTH: 22
<212> TYPE: DNA
<213> ORGANISM: Artificial Sequence
<220> FEATURE:
<223> OTHER INFORMATION: Synthetic DNA

<400> SEQUENCE: 13
tcccttctgt ttcctcagtg tt                                                    22

<210> SEQ ID NO 14
<211> LENGTH: 23
<212> TYPE: DNA
<213> ORGANISM: Artificial Sequence

```
<220> FEATURE:
<223> OTHER INFORMATION: Synthetic DNA

<400> SEQUENCE: 14
cctgccccga taaaaatatc tac                                              23

<210> SEQ ID NO 15
<211> LENGTH: 23
<212> TYPE: DNA
<213> ORGANISM: Artificial Sequence
<220> FEATURE:
<223> OTHER INFORMATION: Synthetic DNA

<400> SEQUENCE: 15
ttgaccttaa gcctctttc ctc                                               23

<210> SEQ ID NO 16
<211> LENGTH: 23
<212> TYPE: DNA
<213> ORGANISM: Artificial Sequence
<220> FEATURE:
<223> OTHER INFORMATION: Synthetic DNA

<400> SEQUENCE: 16
ataacgtaca ttcccatgac acc                                              23

<210> SEQ ID NO 17
<211> LENGTH: 21
<212> TYPE: DNA
<213> ORGANISM: Artificial Sequence
<220> FEATURE:
<223> OTHER INFORMATION: Synthetic DNA

<400> SEQUENCE: 17
actttcaaga tgggaccaag g                                                21

<210> SEQ ID NO 18
<211> LENGTH: 23
<212> TYPE: DNA
<213> ORGANISM: Artificial Sequence
<220> FEATURE:
<223> OTHER INFORMATION: Synthetic DNA

<400> SEQUENCE: 18
atatacacag aagcatgacg cag                                              23

<210> SEQ ID NO 19
<211> LENGTH: 22
<212> TYPE: DNA
<213> ORGANISM: Artificial Sequence
<220> FEATURE:
<223> OTHER INFORMATION: Synthetic DNA

<400> SEQUENCE: 19
ttgctggact ctgaaatatc cc                                               22

<210> SEQ ID NO 20
<211> LENGTH: 24
<212> TYPE: DNA
<213> ORGANISM: Artificial Sequence
<220> FEATURE:
<223> OTHER INFORMATION: Synthetic DNA

<400> SEQUENCE: 20
ttcccctgta cagtatttca ctca                                             24
```

<210> SEQ ID NO 21
<211> LENGTH: 23
<212> TYPE: DNA
<213> ORGANISM: Artificial Sequence
<220> FEATURE:
<223> OTHER INFORMATION: Synthetic DNA

<400> SEQUENCE: 21
ctgagcaatc tgctctatcc tct                                          23

<210> SEQ ID NO 22
<211> LENGTH: 23
<212> TYPE: DNA
<213> ORGANISM: Artificial Sequence
<220> FEATURE:
<223> OTHER INFORMATION: Synthetic DNA

<400> SEQUENCE: 22
gttccagatt cgtgagaatg act                                          23

<210> SEQ ID NO 23
<211> LENGTH: 22
<212> TYPE: DNA
<213> ORGANISM: Artificial Sequence
<220> FEATURE:
<223> OTHER INFORMATION: Synthetic DNA

<400> SEQUENCE: 23
accagtaaca actgtgggat gg                                           22

<210> SEQ ID NO 24
<211> LENGTH: 23
<212> TYPE: DNA
<213> ORGANISM: Artificial Sequence
<220> FEATURE:
<223> OTHER INFORMATION: Synthetic DNA

<400> SEQUENCE: 24
caaatgagct acaacacaca agg                                          23

<210> SEQ ID NO 25
<211> LENGTH: 22
<212> TYPE: DNA
<213> ORGANISM: Artificial Sequence
<220> FEATURE:
<223> OTHER INFORMATION: Synthetic DNA

<400> SEQUENCE: 25
cccnctccac cttgtacata at                                           22

<210> SEQ ID NO 26
<211> LENGTH: 21
<212> TYPE: DNA
<213> ORGANISM: Artificial Sequence
<220> FEATURE:
<223> OTHER INFORMATION: Synthetic DNA

<400> SEQUENCE: 26
gttttcgttt ggctggttgt g                                            21

<210> SEQ ID NO 27
<211> LENGTH: 21
<212> TYPE: DNA
<213> ORGANISM: Artificial Sequence
<220> FEATURE:
<223> OTHER INFORMATION: Synthetic DNA

```
<400> SEQUENCE: 27
gtctgagatt ttactgcacc g                                              21

<210> SEQ ID NO 28
<211> LENGTH: 23
<212> TYPE: DNA
<213> ORGANISM: Artificial Sequence
<220> FEATURE:
<223> OTHER INFORMATION: Synthetic DNA

<400> SEQUENCE: 28
attgctaagg ataagtgctg ctc                                            23

<210> SEQ ID NO 29
<211> LENGTH: 23
<212> TYPE: DNA
<213> ORGANISM: Artificial Sequence
<220> FEATURE:
<223> OTHER INFORMATION: Synthetic DNA

<400> SEQUENCE: 29
tgtcagtata gaagcctgtg ggt                                            23

<210> SEQ ID NO 30
<211> LENGTH: 23
<212> TYPE: DNA
<213> ORGANISM: Artificial Sequence
<220> FEATURE:
<223> OTHER INFORMATION: Synthetic DNA

<400> SEQUENCE: 30
ttcttaggcc atccctttc tac                                             23

<210> SEQ ID NO 31
<211> LENGTH: 23
<212> TYPE: DNA
<213> ORGANISM: Artificial Sequence
<220> FEATURE:
<223> OTHER INFORMATION: Synthetic DNA

<400> SEQUENCE: 31
gcatctgaat gtctttctcc cta                                            23

<210> SEQ ID NO 32
<211> LENGTH: 23
<212> TYPE: DNA
<213> ORGANISM: Artificial Sequence
<220> FEATURE:
<223> OTHER INFORMATION: Synthetic DNA

<400> SEQUENCE: 32
ccataggatc ttgactccaa cag                                            23

<210> SEQ ID NO 33
<211> LENGTH: 23
<212> TYPE: DNA
<213> ORGANISM: Artificial Sequence
<220> FEATURE:
<223> OTHER INFORMATION: Synthetic DNA

<400> SEQUENCE: 33
actgggagtg gaggaaatta gag                                            23

<210> SEQ ID NO 34
```

```
<210> SEQ ID NO 34
<211> LENGTH: 23
<212> TYPE: DNA
<213> ORGANISM: Artificial Sequence
<220> FEATURE:
<223> OTHER INFORMATION: Synthetic DNA

<400> SEQUENCE: 34
ctaatgtaag ctccattggg atg                                              23

<210> SEQ ID NO 35
<211> LENGTH: 23
<212> TYPE: DNA
<213> ORGANISM: Artificial Sequence
<220> FEATURE:
<223> OTHER INFORMATION: Synthetic DNA

<400> SEQUENCE: 35
caaactgcaa actagctccc taa                                              23

<210> SEQ ID NO 36
<211> LENGTH: 23
<212> TYPE: DNA
<213> ORGANISM: Artificial Sequence
<220> FEATURE:
<223> OTHER INFORMATION: Synthetic DNA

<400> SEQUENCE: 36
aggtaaccca aagtgacaaa cct                                              23

<210> SEQ ID NO 37
<211> LENGTH: 23
<212> TYPE: DNA
<213> ORGANISM: Artificial Sequence
<220> FEATURE:
<223> OTHER INFORMATION: Synthetic DNA

<400> SEQUENCE: 37
aagactaaga gggaaaatgt ggg                                              23

<210> SEQ ID NO 38
<211> LENGTH: 23
<212> TYPE: DNA
<213> ORGANISM: Artificial Sequence
<220> FEATURE:
<223> OTHER INFORMATION: Synthetic DNA

<400> SEQUENCE: 38
aggtaaccca aagtgacaaa cct                                              23

<210> SEQ ID NO 39
<211> LENGTH: 23
<212> TYPE: DNA
<213> ORGANISM: Artificial Sequence
<220> FEATURE:
<223> OTHER INFORMATION: Synthetic DNA

<400> SEQUENCE: 39
ttaagtgagt ctccttggct gag                                              23

<210> SEQ ID NO 40
<211> LENGTH: 23
<212> TYPE: DNA
<213> ORGANISM: Artificial Sequence
<220> FEATURE:
<223> OTHER INFORMATION: Synthetic DNA

<400> SEQUENCE: 40
``` agggcccta tatccaatac cta    23

<210> SEQ ID NO 41
<211> LENGTH: 23
<212> TYPE: DNA
<213> ORGANISM: Artificial Sequence
<220> FEATURE:
<223> OTHER INFORMATION: Synthetic DNA

<400> SEQUENCE: 41
agtcattcag aagccattga gac    23

<210> SEQ ID NO 42
<211> LENGTH: 20
<212> TYPE: DNA
<213> ORGANISM: Artificial Sequence
<220> FEATURE:
<223> OTHER INFORMATION: Synthetic DNA

<400> SEQUENCE: 42
tgggtggaat catattggaa    20

<210> SEQ ID NO 43
<211> LENGTH: 19
<212> TYPE: DNA
<213> ORGANISM: Artificial Sequence
<220> FEATURE:
<223> OTHER INFORMATION: Synthetic DNA

<400> SEQUENCE: 43
gaaaggtgaa ggtcggagt    19

<210> SEQ ID NO 44
<211> LENGTH: 20
<212> TYPE: DNA
<213> ORGANISM: Artificial Sequence
<220> FEATURE:
<223> OTHER INFORMATION: Synthetic DNA

<400> SEQUENCE: 44
tgggtggaat catattggaa    20

<210> SEQ ID NO 45
<211> LENGTH: 23
<212> TYPE: DNA
<213> ORGANISM: Artificial Sequence
<220> FEATURE:
<223> OTHER INFORMATION: Synthetic DNA

<400> SEQUENCE: 45
ccagacatcc atggtaccta taa    23

<210> SEQ ID NO 46
<211> LENGTH: 23
<212> TYPE: DNA
<213> ORGANISM: Artificial Sequence
<220> FEATURE:
<223> OTHER INFORMATION: Synthetic DNA

<400> SEQUENCE: 46
tatgcattga aaccttacag ggg    23

<210> SEQ ID NO 47
<211> LENGTH: 24
<212> TYPE: DNA

```
<213> ORGANISM: Artificial Sequence
<220> FEATURE:
<223> OTHER INFORMATION: Synthetic DNA

<400> SEQUENCE: 47
ctgttaaaca aagcgaggtt aagg                                          24

<210> SEQ ID NO 48
<211> LENGTH: 23
<212> TYPE: DNA
<213> ORGANISM: Artificial Sequence
<220> FEATURE:
<223> OTHER INFORMATION: Synthetic DNA

<400> SEQUENCE: 48
gggttctgca tctcgtttat tag                                           23

<210> SEQ ID NO 49
<211> LENGTH: 23
<212> TYPE: DNA
<213> ORGANISM: Artificial Sequence
<220> FEATURE:
<223> OTHER INFORMATION: Synthetic DNA

<400> SEQUENCE: 49
gacacatagc tcataggcac aca                                           23

<210> SEQ ID NO 50
<211> LENGTH: 23
<212> TYPE: DNA
<213> ORGANISM: Artificial Sequence
<220> FEATURE:
<223> OTHER INFORMATION: Synthetic DNA

<400> SEQUENCE: 50
ttctggtaca tggtaagtgc tca                                           23

<210> SEQ ID NO 51
<211> LENGTH: 22
<212> TYPE: DNA
<213> ORGANISM: Artificial Sequence
<220> FEATURE:
<223> OTHER INFORMATION: Synthetic DNA

<400> SEQUENCE: 51
tccgccatat tgattctgct ta                                            22

<210> SEQ ID NO 52
<211> LENGTH: 23
<212> TYPE: DNA
<213> ORGANISM: Artificial Sequence
<220> FEATURE:
<223> OTHER INFORMATION: Synthetic DNA

<400> SEQUENCE: 52
gtttgctttc tggaccatgg ata                                           23

<210> SEQ ID NO 53
<211> LENGTH: 22
<212> TYPE: DNA
<213> ORGANISM: Artificial Sequence
<220> FEATURE:
<223> OTHER INFORMATION: Synthetic DNA

<400> SEQUENCE: 53
gataacaact ggaccacatc cc                                            22
```

<210> SEQ ID NO 54
<211> LENGTH: 22
<212> TYPE: DNA
<213> ORGANISM: Artificial Sequence
<220> FEATURE:
<223> OTHER INFORMATION: Synthetic DNA

<400> SEQUENCE: 54
aacaggcaga cgaggtagac ac                                              22

<210> SEQ ID NO 55
<211> LENGTH: 21
<212> TYPE: DNA
<213> ORGANISM: Artificial Sequence
<220> FEATURE:
<223> OTHER INFORMATION: Synthetic DNA

<400> SEQUENCE: 55
gagaaggatg ggtccaccag t                                               21

<210> SEQ ID NO 56
<211> LENGTH: 23
<212> TYPE: DNA
<213> ORGANISM: Artificial Sequence
<220> FEATURE:
<223> OTHER INFORMATION: Synthetic DNA

<400> SEQUENCE: 56
gtacatgggc agcacaaatg tat                                             23

<210> SEQ ID NO 57
<211> LENGTH: 23
<212> TYPE: DNA
<213> ORGANISM: Artificial Sequence
<220> FEATURE:
<223> OTHER INFORMATION: Synthetic DNA

<400> SEQUENCE: 57
atttcattgg tagtatggcc cac                                             23

<210> SEQ ID NO 58
<211> LENGTH: 23
<212> TYPE: DNA
<213> ORGANISM: Artificial Sequence
<220> FEATURE:
<223> OTHER INFORMATION: Synthetic DNA

<400> SEQUENCE: 58
ataccatggg acaggattgt aag                                             23

<210> SEQ ID NO 59
<211> LENGTH: 23
<212> TYPE: DNA
<213> ORGANISM: Artificial Sequence
<220> FEATURE:
<223> OTHER INFORMATION: Synthetic DNA

<400> SEQUENCE: 59
gctcagacca gctcatactt cat                                             23

<210> SEQ ID NO 60
<211> LENGTH: 23
<212> TYPE: DNA
<213> ORGANISM: Artificial Sequence
<220> FEATURE:

<223> OTHER INFORMATION: Synthetic DNA

<400> SEQUENCE: 60
ccaaagactg gggtaggtaa aac                                              23

<210> SEQ ID NO 61
<211> LENGTH: 23
<212> TYPE: DNA
<213> ORGANISM: Artificial Sequence
<220> FEATURE:
<223> OTHER INFORMATION: Synthetic DNA

<400> SEQUENCE: 61
ctggtgcttt ctatcacctc ttc                                              23

<210> SEQ ID NO 62
<211> LENGTH: 23
<212> TYPE: DNA
<213> ORGANISM: Artificial Sequence
<220> FEATURE:
<223> OTHER INFORMATION: Synthetic DNA

<400> SEQUENCE: 62
gactagtgtg aaacaagatg ggc                                              23

<210> SEQ ID NO 63
<211> LENGTH: 22
<212> TYPE: DNA
<213> ORGANISM: Artificial Sequence
<220> FEATURE:
<223> OTHER INFORMATION: Synthetic DNA

<400> SEQUENCE: 63
cttgaaccca ggagtttgag ac                                               22

<210> SEQ ID NO 64
<211> LENGTH: 22
<212> TYPE: DNA
<213> ORGANISM: Artificial Sequence
<220> FEATURE:
<223> OTHER INFORMATION: Synthetic DNA

<400> SEQUENCE: 64
gtgcctcagc tttctgagta gc                                               22

<210> SEQ ID NO 65
<211> LENGTH: 22
<212> TYPE: DNA
<213> ORGANISM: Artificial Sequence
<220> FEATURE:
<223> OTHER INFORMATION: Synthetic DNA

<400> SEQUENCE: 65
ctggtgctga ctatccagtt ga                                               22

<210> SEQ ID NO 66
<211> LENGTH: 23
<212> TYPE: DNA
<213> ORGANISM: Artificial Sequence
<220> FEATURE:
<223> OTHER INFORMATION: Synthetic DNA

<400> SEQUENCE: 66
ctggtaaact gtccaaaaca agg                                              23

```
<210> SEQ ID NO 67
<211> LENGTH: 22
<212> TYPE: DNA
<213> ORGANISM: Artificial Sequence
<220> FEATURE:
<223> OTHER INFORMATION: Synthetic DNA

<400> SEQUENCE: 67
ctcttacctg gacaaggtgc gt                                           22

<210> SEQ ID NO 68
<211> LENGTH: 21
<212> TYPE: DNA
<213> ORGANISM: Artificial Sequence
<220> FEATURE:
<223> OTHER INFORMATION: Synthetic DNA

<400> SEQUENCE: 68
ggatgagctc tgctccttga g                                            21

<210> SEQ ID NO 69
<211> LENGTH: 21
<212> TYPE: DNA
<213> ORGANISM: Artificial Sequence
<220> FEATURE:
<223> OTHER INFORMATION: Synthetic DNA

<400> SEQUENCE: 69
caatgtttga ccagtcccag a                                            21

<210> SEQ ID NO 70
<211> LENGTH: 24
<212> TYPE: DNA
<213> ORGANISM: Artificial Sequence
<220> FEATURE:
<223> OTHER INFORMATION: Synthetic DNA

<400> SEQUENCE: 70
catgttgtct cagtcctcta ttgg                                         24

<210> SEQ ID NO 71
<211> LENGTH: 21
<212> TYPE: DNA
<213> ORGANISM: Artificial Sequence
<220> FEATURE:
<223> OTHER INFORMATION: Synthetic DNA

<400> SEQUENCE: 71
ggacagcagc tggagtacac a                                            21

<210> SEQ ID NO 72
<211> LENGTH: 21
<212> TYPE: DNA
<213> ORGANISM: Artificial Sequence
<220> FEATURE:
<223> OTHER INFORMATION: Synthetic DNA

<400> SEQUENCE: 72
aatcagattt gtcggtgcct t                                            21

<210> SEQ ID NO 73
<211> LENGTH: 23
<212> TYPE: DNA
<213> ORGANISM: Artificial Sequence
<220> FEATURE:
<223> OTHER INFORMATION: Synthetic DNA
```

<400> SEQUENCE: 73
ggctctgcac taagaacaca gag					23

<210> SEQ ID NO 74
<211> LENGTH: 23
<212> TYPE: DNA
<213> ORGANISM: Artificial Sequence
<220> FEATURE:
<223> OTHER INFORMATION: Synthetic DNA

<400> SEQUENCE: 74
acaactagct ctcagttcag gca					23

<210> SEQ ID NO 75
<211> LENGTH: 23
<212> TYPE: DNA
<213> ORGANISM: Artificial Sequence
<220> FEATURE:
<223> OTHER INFORMATION: Synthetic DNA

<400> SEQUENCE: 75
tggagcagta tgacaagcta caa					23

<210> SEQ ID NO 76
<211> LENGTH: 23
<212> TYPE: DNA
<213> ORGANISM: Artificial Sequence
<220> FEATURE:
<223> OTHER INFORMATION: Synthetic DNA

<400> SEQUENCE: 76
aagcagcact gcataaactg ttc					23

<210> SEQ ID NO 77
<211> LENGTH: 23
<212> TYPE: DNA
<213> ORGANISM: Artificial Sequence
<220> FEATURE:
<223> OTHER INFORMATION: Synthetic DNA

<400> SEQUENCE: 77
taagtacttt cctgtgggtc gct					23

<210> SEQ ID NO 78
<211> LENGTH: 23
<212> TYPE: DNA
<213> ORGANISM: Artificial Sequence
<220> FEATURE:
<223> OTHER INFORMATION: Synthetic DNA

<400> SEQUENCE: 78
ccacaaacag gaagctatgt tct					23

<210> SEQ ID NO 79
<211> LENGTH: 23
<212> TYPE: DNA
<213> ORGANISM: Artificial Sequence
<220> FEATURE:
<223> OTHER INFORMATION: Synthetic DNA

<400> SEQUENCE: 79
gtactattag ccatggtcaa ccc					23

<210> SEQ ID NO 80
<211> LENGTH: 23

```
<212> TYPE: DNA
<213> ORGANISM: Artificial Sequence
<220> FEATURE:
<223> OTHER INFORMATION: Synthetic DNA

<400> SEQUENCE: 80
ctacagaagg aatgatctgg tgg                                          23

<210> SEQ ID NO 81
<211> LENGTH: 23
<212> TYPE: DNA
<213> ORGANISM: Artificial Sequence
<220> FEATURE:
<223> OTHER INFORMATION: Synthetic DNA

<400> SEQUENCE: 81
atcagtacgg ggaccttaca aac                                          23

<210> SEQ ID NO 82
<211> LENGTH: 23
<212> TYPE: DNA
<213> ORGANISM: Artificial Sequence
<220> FEATURE:
<223> OTHER INFORMATION: Synthetic DNA

<400> SEQUENCE: 82
cctgtactga gctctccaaa gac                                          23

<210> SEQ ID NO 83
<211> LENGTH: 20
<212> TYPE: DNA
<213> ORGANISM: Artificial Sequence
<220> FEATURE:
<223> OTHER INFORMATION: Synthetic DNA

<400> SEQUENCE: 83
tccctagctt cctctccaca                                              20

<210> SEQ ID NO 84
<211> LENGTH: 20
<212> TYPE: DNA
<213> ORGANISM: Artificial Sequence
<220> FEATURE:
<223> OTHER INFORMATION: Synthetic DNA

<400> SEQUENCE: 84
agaatcatgc ctcccctct                                               20

<210> SEQ ID NO 85
<211> LENGTH: 22
<212> TYPE: DNA
<213> ORGANISM: Artificial Sequence
<220> FEATURE:
<223> OTHER INFORMATION: Synthetic DNA

<400> SEQUENCE: 85
acccctcaag tgtaaggaac tg                                           22

<210> SEQ ID NO 86
<211> LENGTH: 23
<212> TYPE: DNA
<213> ORGANISM: Artificial Sequence
<220> FEATURE:
<223> OTHER INFORMATION: Synthetic DNA

<400> SEQUENCE: 86
```
ggatcaagag tgtgtgtgtg tgt 23

<210> SEQ ID NO 87
<211> LENGTH: 23
<212> TYPE: DNA
<213> ORGANISM: Artificial Sequence
<220> FEATURE:
<223> OTHER INFORMATION: Synthetic DNA

<400> SEQUENCE: 87
caatgccaga gagaatatcc aga 23

<210> SEQ ID NO 88
<211> LENGTH: 23
<212> TYPE: DNA
<213> ORGANISM: Artificial Sequence
<220> FEATURE:
<223> OTHER INFORMATION: Synthetic DNA

<400> SEQUENCE: 88
gatacccatt gtgtaccctc tcc 23

<210> SEQ ID NO 89
<211> LENGTH: 22
<212> TYPE: DNA
<213> ORGANISM: Artificial Sequence
<220> FEATURE:
<223> OTHER INFORMATION: Synthetic DNA

<400> SEQUENCE: 89
ccactccaca taagggtttt ag 22

<210> SEQ ID NO 90
<211> LENGTH: 23
<212> TYPE: DNA
<213> ORGANISM: Artificial Sequence
<220> FEATURE:
<223> OTHER INFORMATION: Synthetic DNA

<400> SEQUENCE: 90
gaggttctag ctaagtgcag ggt 23

<210> SEQ ID NO 91
<211> LENGTH: 25
<212> TYPE: DNA
<213> ORGANISM: Artificial Sequence
<220> FEATURE:
<223> OTHER INFORMATION: Synthetic DNA

<400> SEQUENCE: 91
ccattgacat tggagttaag tatgc 25

<210> SEQ ID NO 92
<211> LENGTH: 22
<212> TYPE: DNA
<213> ORGANISM: Artificial Sequence
<220> FEATURE:
<223> OTHER INFORMATION: Synthetic DNA

<400> SEQUENCE: 92
ggcaaagacc acatttagca at 22

<210> SEQ ID NO 93
<211> LENGTH: 23
<212> TYPE: DNA
<213> ORGANISM: Artificial Sequence
<220> FEATURE:
<223> OTHER INFORMATION: Synthetic DNA

<400> SEQUENCE: 93
gaaagcctat gtgaaaagct ggt                                           23

<210> SEQ ID NO 94
<211> LENGTH: 22
<212> TYPE: DNA
<213> ORGANISM: Artificial Sequence
<220> FEATURE:
<223> OTHER INFORMATION: Synthetic DNA

<400> SEQUENCE: 94
ttgtttccag gcattaagtg tg                                            22

<210> SEQ ID NO 95
<211> LENGTH: 23
<212> TYPE: DNA
<213> ORGANISM: Artificial Sequence
<220> FEATURE:
<223> OTHER INFORMATION: Synthetic DNA

<400> SEQUENCE: 95
gcatcttagt ccacacagtt ggt                                           23

<210> SEQ ID NO 96
<211> LENGTH: 23
<212> TYPE: DNA
<213> ORGANISM: Artificial Sequence
<220> FEATURE:
<223> OTHER INFORMATION: Synthetic DNA

<400> SEQUENCE: 96
gcccttacag gtggagtatc ttc                                           23

<210> SEQ ID NO 97
<211> LENGTH: 23
<212> TYPE: DNA
<213> ORGANISM: Artificial Sequence
<220> FEATURE:
<223> OTHER INFORMATION: Synthetic DNA

<400> SEQUENCE: 97
ctcatagcca gcatgacttc ttt                                           23

<210> SEQ ID NO 98
<211> LENGTH: 23
<212> TYPE: DNA
<213> ORGANISM: Artificial Sequence
<220> FEATURE:
<223> OTHER INFORMATION: Synthetic DNA

<400> SEQUENCE: 98
ggttcacttg tgactggtca tct                                           23

<210> SEQ ID NO 99
<211> LENGTH: 22
<212> TYPE: DNA
<213> ORGANISM: Artificial Sequence
<220> FEATURE:
<223> OTHER INFORMATION: Synthetic DNA

<400> SEQUENCE: 99 actttctga gcagacgtcc ag                                             22

<210> SEQ ID NO 100
<211> LENGTH: 23
<212> TYPE: DNA
<213> ORGANISM: Artificial Sequence
<220> FEATURE:
<223> OTHER INFORMATION: Synthetic DNA

<400> SEQUENCE: 100
tatcaaaaga acacacaggt ggc                                              23

<210> SEQ ID NO 101
<211> LENGTH: 23
<212> TYPE: DNA
<213> ORGANISM: Artificial Sequence
<220> FEATURE:
<223> OTHER INFORMATION: Synthetic DNA

<400> SEQUENCE: 101
acgttattcc cagttcctaa acc                                              23

<210> SEQ ID NO 102
<211> LENGTH: 23
<212> TYPE: DNA
<213> ORGANISM: Artificial Sequence
<220> FEATURE:
<223> OTHER INFORMATION: Synthetic DNA

<400> SEQUENCE: 102
agtctcgggt gactcaatat gaa                                              23

<210> SEQ ID NO 103
<211> LENGTH: 23
<212> TYPE: DNA
<213> ORGANISM: Artificial Sequence
<220> FEATURE:
<223> OTHER INFORMATION: Synthetic DNA

<400> SEQUENCE: 103
agttgaaccc aggtaccttt ctc                                              23

<210> SEQ ID NO 104
<211> LENGTH: 23
<212> TYPE: DNA
<213> ORGANISM: Artificial Sequence
<220> FEATURE:
<223> OTHER INFORMATION: Synthetic DNA

<400> SEQUENCE: 104 ctaggcccttt ttagaaaaca tgg                                             23

<210> SEQ ID NO 105
<211> LENGTH: 23
<212> TYPE: DNA
<213> ORGANISM: Artificial Sequence
<220> FEATURE:
<223> OTHER INFORMATION: Synthetic DNA

<400> SEQUENCE: 105
tactgggaac gactaaggac tca                                              23

<210> SEQ ID NO 106
<211> LENGTH: 23
<212> TYPE: DNA
<213> ORGANISM: Artificial Sequence
<220> FEATURE:
<223> OTHER INFORMATION: Synthetic DNA

```
<400> SEQUENCE: 106
tgctgtgttg agtaggtttc tga                                              23

<210> SEQ ID NO 107
<211> LENGTH: 23
<212> TYPE: DNA
<213> ORGANISM: Artificial Sequence
<220> FEATURE:
<223> OTHER INFORMATION: Synthetic DNA

<400> SEQUENCE: 107
tgagagtcct cagagggtat cag                                              23

<210> SEQ ID NO 108
<211> LENGTH: 23
<212> TYPE: DNA
<213> ORGANISM: Artificial Sequence
<220> FEATURE:
<223> OTHER INFORMATION: Synthetic DNA

<400> SEQUENCE: 108
cttgaagtca agagtcctgg tgt                                              23

<210> SEQ ID NO 109
<211> LENGTH: 20
<212> TYPE: DNA
<213> ORGANISM: Artificial Sequence
<220> FEATURE:
<223> OTHER INFORMATION: Synthetic DNA

<400> SEQUENCE: 109
tttctgttgg caagttgctg                                                  20

<210> SEQ ID NO 110
<211> LENGTH: 20
<212> TYPE: DNA
<213> ORGANISM: Artificial Sequence
<220> FEATURE:
<223> OTHER INFORMATION: Synthetic DNA

<400> SEQUENCE: 110
ccctttaagc ccacttcctc                                                  20

<210> SEQ ID NO 111
<211> LENGTH: 23
<212> TYPE: DNA
<213> ORGANISM: Artificial Sequence
<220> FEATURE:
<223> OTHER INFORMATION: Synthetic DNA

<400> SEQUENCE: 111
gatgagaaga tgaagagctt gga                                              23

<210> SEQ ID NO 112
<211> LENGTH: 23
<212> TYPE: DNA
<213> ORGANISM: Artificial Sequence
<220> FEATURE:
<223> OTHER INFORMATION: Synthetic DNA

<400> SEQUENCE: 112
gaggaagctt tatttgggaa gag                                              23

<210> SEQ ID NO 113
```

<211> LENGTH: 21
<212> TYPE: DNA
<213> ORGANISM: Artificial Sequence
<220> FEATURE:
<223> OTHER INFORMATION: Synthetic DNA

<400> SEQUENCE: 113
acttccctct ctgcctttct g                                    21

<210> SEQ ID NO 114
<211> LENGTH: 23
<212> TYPE: DNA
<213> ORGANISM: Artificial Sequence
<220> FEATURE:
<223> OTHER INFORMATION: Synthetic DNA

<400> SEQUENCE: 114
cagattgttt tgggcttctc act                                  23

<210> SEQ ID NO 115
<211> LENGTH: 20
<212> TYPE: DNA
<213> ORGANISM: Artificial Sequence
<220> FEATURE:
<223> OTHER INFORMATION: Synthetic DNA

<400> SEQUENCE: 115
gtctggtcag ctttgcttcc                                      20

<210> SEQ ID NO 116
<211> LENGTH: 20
<212> TYPE: DNA
<213> ORGANISM: Artificial Sequence
<220> FEATURE:
<223> OTHER INFORMATION: Synthetic DNA

<400> SEQUENCE: 116
ggcaagttct gcacagatga                                      20

<210> SEQ ID NO 117
<211> LENGTH: 20
<212> TYPE: DNA
<213> ORGANISM: Artificial Sequence
<220> FEATURE:
<223> OTHER INFORMATION: Synthetic DNA

<400> SEQUENCE: 117
cagctcagtg caccatgaat                                      20

<210> SEQ ID NO 118
<211> LENGTH: 20
<212> TYPE: DNA
<213> ORGANISM: Artificial Sequence
<220> FEATURE:
<223> OTHER INFORMATION: Synthetic DNA

<400> SEQUENCE: 118
gtgggactga gatgcaggat                                      20

<210> SEQ ID NO 119
<211> LENGTH: 23
<212> TYPE: DNA
<213> ORGANISM: Artificial Sequence
<220> FEATURE:
<223> OTHER INFORMATION: Synthetic DNA

<400> SEQUENCE: 119

```
cacggactca tgaatgtagt gaa                                                23

<210> SEQ ID NO 120
<211> LENGTH: 23
<212> TYPE: DNA
<213> ORGANISM: Artificial Sequence
<220> FEATURE:
<223> OTHER INFORMATION: Synthetic DNA

<400> SEQUENCE: 120
gtgtagtggc acgatcatag ctt                                                23

<210> SEQ ID NO 121
<211> LENGTH: 20
<212> TYPE: DNA
<213> ORGANISM: Artificial Sequence
<220> FEATURE:
<223> OTHER INFORMATION: Synthetic DNA

<400> SEQUENCE: 121
gggaccaaac agaccaaaga                                                    20

<210> SEQ ID NO 122
<211> LENGTH: 20
<212> TYPE: DNA
<213> ORGANISM: Artificial Sequence
<220> FEATURE:
<223> OTHER INFORMATION: Synthetic DNA

<400> SEQUENCE: 122
caccccacag agcctgtatt                                                    20

<210> SEQ ID NO 123
<211> LENGTH: 22
<212> TYPE: DNA
<213> ORGANISM: Artificial Sequence
<220> FEATURE:
<223> OTHER INFORMATION: Synthetic DNA

<400> SEQUENCE: 123
cggaaaggca ctatttcaca at                                                 22

<210> SEQ ID NO 124
<211> LENGTH: 21
<212> TYPE: DNA
<213> ORGANISM: Artificial Sequence
<220> FEATURE:
<223> OTHER INFORMATION: Synthetic DNA

<400> SEQUENCE: 124
acaggcccac aggtttgtaa c                                                  21

<210> SEQ ID NO 125
<211> LENGTH: 20
<212> TYPE: DNA
<213> ORGANISM: Artificial Sequence
<220> FEATURE:
<223> OTHER INFORMATION: Synthetic DNA

<400> SEQUENCE: 125
aagctcttca gctgcgtctc                                                    20

<210> SEQ ID NO 126
<211> LENGTH: 20
<212> TYPE: DNA
```

```
<213> ORGANISM: Artificial Sequence
<220> FEATURE:
<223> OTHER INFORMATION: Synthetic DNA

<400> SEQUENCE: 126
cctcctcctt ttcagctgtg                                                   20

<210> SEQ ID NO 127
<211> LENGTH: 22
<212> TYPE: DNA
<213> ORGANISM: Artificial Sequence
<220> FEATURE:
<223> OTHER INFORMATION: Synthetic DNA

<400> SEQUENCE: 127
tctggaaccc taaaagtgtc gt                                                22

<210> SEQ ID NO 128
<211> LENGTH: 23
<212> TYPE: DNA
<213> ORGANISM: Artificial Sequence
<220> FEATURE:
<223> OTHER INFORMATION: Synthetic DNA

<400> SEQUENCE: 128
tctttcaaca tctctccacc cta                                               23

<210> SEQ ID NO 129
<211> LENGTH: 21
<212> TYPE: DNA
<213> ORGANISM: Artificial Sequence
<220> FEATURE:
<223> OTHER INFORMATION: Synthetic DNA

<400> SEQUENCE: 129
agatacctgg agaacgggaa g                                                 21

<210> SEQ ID NO 130
<211> LENGTH: 23
<212> TYPE: DNA
<213> ORGANISM: Artificial Sequence
<220> FEATURE:
<223> OTHER INFORMATION: Synthetic DNA

<400> SEQUENCE: 130
ggaagtaaga agttgcagct cag                                               23

<210> SEQ ID NO 131
<211> LENGTH: 18
<212> TYPE: DNA
<213> ORGANISM: Artificial Sequence
<220> FEATURE:
<223> OTHER INFORMATION: Synthetic DNA

<400> SEQUENCE: 131
attaggtttc acccaaag                                                     18

<210> SEQ ID NO 132
<211> LENGTH: 19
<212> TYPE: DNA
<213> ORGANISM: Artificial Sequence
<220> FEATURE:
<223> OTHER INFORMATION: Synthetic DNA

<400> SEQUENCE: 132
agacgagact tgttttctc                                                    19
```

<210> SEQ ID NO 133
<211> LENGTH: 20
<212> TYPE: DNA
<213> ORGANISM: Artificial Sequence
<220> FEATURE:
<223> OTHER INFORMATION: Synthetic DNA

<400> SEQUENCE: 133
cagggacttg gtcacaggtt                                              20

<210> SEQ ID NO 134
<211> LENGTH: 20
<212> TYPE: DNA
<213> ORGANISM: Artificial Sequence
<220> FEATURE:
<223> OTHER INFORMATION: Synthetic DNA

<400> SEQUENCE: 134
ttcttctccc tcccttgat                                               20

<210> SEQ ID NO 135
<211> LENGTH: 21
<212> TYPE: DNA
<213> ORGANISM: Artificial Sequence
<220> FEATURE:
<223> OTHER INFORMATION: Synthetic DNA

<400> SEQUENCE: 135
gattacatcg ccctgaacga g                                            21

<210> SEQ ID NO 136
<211> LENGTH: 22
<212> TYPE: DNA
<213> ORGANISM: Artificial Sequence
<220> FEATURE:
<223> OTHER INFORMATION: Synthetic DNA

<400> SEQUENCE: 136
tccatcaacc tctcatagca aa                                           22

<210> SEQ ID NO 137
<211> LENGTH: 21
<212> TYPE: DNA
<213> ORGANISM: Artificial Sequence
<220> FEATURE:
<223> OTHER INFORMATION: Synthetic DNA

<400> SEQUENCE: 137
gtaagatccg cagacgtaag g                                            21

<210> SEQ ID NO 138
<211> LENGTH: 23
<212> TYPE: DNA
<213> ORGANISM: Artificial Sequence
<220> FEATURE:
<223> OTHER INFORMATION: Synthetic DNA

<400> SEQUENCE: 138
ctgaagtcag cctctgtaac ctc                                          23

<210> SEQ ID NO 139
<211> LENGTH: 20
<212> TYPE: DNA
<213> ORGANISM: Artificial Sequence
<220> FEATURE:

<223> OTHER INFORMATION: Synthetic DNA

<400> SEQUENCE: 139
actgacccca cttcttgtgg                                            20

<210> SEQ ID NO 140
<211> LENGTH: 19
<212> TYPE: DNA
<213> ORGANISM: Artificial Sequence
<220> FEATURE:
<223> OTHER INFORMATION: Synthetic DNA

<400> SEQUENCE: 140
acccttccct gttgctgtc                                             19

<210> SEQ ID NO 141
<211> LENGTH: 23
<212> TYPE: DNA
<213> ORGANISM: Artificial Sequence
<220> FEATURE:
<223> OTHER INFORMATION: Synthetic DNA

<400> SEQUENCE: 141
tcaaagtatt tagctgactc gcc                                        23

<210> SEQ ID NO 142
<211> LENGTH: 23
<212> TYPE: DNA
<213> ORGANISM: Artificial Sequence
<220> FEATURE:
<223> OTHER INFORMATION: Synthetic DNA

<400> SEQUENCE: 142
tagtcactcc aggtttatgg agg                                        23

<210> SEQ ID NO 143
<211> LENGTH: 23
<212> TYPE: DNA
<213> ORGANISM: Artificial Sequence
<220> FEATURE:
<223> OTHER INFORMATION: Synthetic DNA

<400> SEQUENCE: 143
gggaacttga attcgtatcc atc                                        23

<210> SEQ ID NO 144
<211> LENGTH: 23
<212> TYPE: DNA
<213> ORGANISM: Artificial Sequence
<220> FEATURE:
<223> OTHER INFORMATION: Synthetic DNA

<400> SEQUENCE: 144
ctgaatctca aacctggaga gtg                                        23

<210> SEQ ID NO 145
<211> LENGTH: 22
<212> TYPE: DNA
<213> ORGANISM: Artificial Sequence
<220> FEATURE:
<223> OTHER INFORMATION: Synthetic DNA

<400> SEQUENCE: 145
gatcatcttt cctgttccag ag                                         22

```
<210> SEQ ID NO 146
<211> LENGTH: 22
<212> TYPE: DNA
<213> ORGANISM: Artificial Sequence
<220> FEATURE:
<223> OTHER INFORMATION: Synthetic DNA

<400> SEQUENCE: 146
ctggaaggtt ctcaggtctt ta                                              22

<210> SEQ ID NO 147
<211> LENGTH: 20
<212> TYPE: DNA
<213> ORGANISM: Artificial Sequence
<220> FEATURE:
<223> OTHER INFORMATION: Synthetic DNA

<400> SEQUENCE: 147
gtacgaccag gctgagaagc                                                 20

<210> SEQ ID NO 148
<211> LENGTH: 20
<212> TYPE: DNA
<213> ORGANISM: Artificial Sequence
<220> FEATURE:
<223> OTHER INFORMATION: Synthetic DNA

<400> SEQUENCE: 148
atcttcgggg ctatccaact                                                 20

<210> SEQ ID NO 149
<211> LENGTH: 20
<212> TYPE: DNA
<213> ORGANISM: Artificial Sequence
<220> FEATURE:
<223> OTHER INFORMATION: Synthetic DNA

<400> SEQUENCE: 149
tcagccacga tgagatgttc                                                 20

<210> SEQ ID NO 150
<211> LENGTH: 20
<212> TYPE: DNA
<213> ORGANISM: Artificial Sequence
<220> FEATURE:
<223> OTHER INFORMATION: Synthetic DNA

<400> SEQUENCE: 150
tgtggatgac aagcagaagc                                                 20

<210> SEQ ID NO 151
<211> LENGTH: 20
<212> TYPE: DNA
<213> ORGANISM: Artificial Sequence
<220> FEATURE:
<223> OTHER INFORMATION: Synthetic DNA

<400> SEQUENCE: 151
accttaggag ggcagttggt                                                 20

<210> SEQ ID NO 152
<211> LENGTH: 20
<212> TYPE: DNA
<213> ORGANISM: Artificial Sequence
<220> FEATURE:
<223> OTHER INFORMATION: Synthetic DNA
```

```
<400> SEQUENCE: 152 agggtcaca ccttgaacag                                                    20

<210> SEQ ID NO 153
<211> LENGTH: 20
<212> TYPE: DNA
<213> ORGANISM: Artificial Sequence
<220> FEATURE:
<223> OTHER INFORMATION: Synthetic DNA

<400> SEQUENCE: 153
gcatcctacc accaactcgt                                                   20

<210> SEQ ID NO 154
<211> LENGTH: 20
<212> TYPE: DNA
<213> ORGANISM: Artificial Sequence
<220> FEATURE:
<223> OTHER INFORMATION: Synthetic DNA

<400> SEQUENCE: 154
gcagcatcac cagacttcaa                                                   20

<210> SEQ ID NO 155
<211> LENGTH: 20
<212> TYPE: DNA
<213> ORGANISM: Artificial Sequence
<220> FEATURE:
<223> OTHER INFORMATION: Synthetic DNA

<400> SEQUENCE: 155
acaaacccga tatggctgag                                                   20

<210> SEQ ID NO 156
<211> LENGTH: 20
<212> TYPE: DNA
<213> ORGANISM: Artificial Sequence
<220> FEATURE:
<223> OTHER INFORMATION: Synthetic DNA

<400> SEQUENCE: 156
gccaatgctt gtggaatgta                                                   20

<210> SEQ ID NO 157
<211> LENGTH: 22
<212> TYPE: DNA
<213> ORGANISM: Artificial Sequence
<220> FEATURE:
<223> OTHER INFORMATION: Synthetic DNA

<400> SEQUENCE: 157
tcggaccata atccaagtta cc                                                22

<210> SEQ ID NO 158
<211> LENGTH: 23
<212> TYPE: DNA
<213> ORGANISM: Artificial Sequence
<220> FEATURE:
<223> OTHER INFORMATION: Synthetic DNA

<400> SEQUENCE: 158
taacccgaga atacaccatc aac                                               23

<210> SEQ ID NO 159
<211> LENGTH: 22
```

```
<212> TYPE: DNA
<213> ORGANISM: Artificial Sequence
<220> FEATURE:
<223> OTHER INFORMATION: Synthetic DNA

<400> SEQUENCE: 159
atggttttat tgacggcaga ag                                              22

<210> SEQ ID NO 160
<211> LENGTH: 19
<212> TYPE: DNA
<213> ORGANISM: Artificial Sequence
<220> FEATURE:
<223> OTHER INFORMATION: Synthetic DNA

<400> SEQUENCE: 160
ggaaggtgaa ggtcggagt                                                  19

<210> SEQ ID NO 161
<211> LENGTH: 20
<212> TYPE: DNA
<213> ORGANISM: Artificial Sequence
<220> FEATURE:
<223> OTHER INFORMATION: Synthetic DNA

<400> SEQUENCE: 161
tgggtggaat catattggaa                                                 20

<210> SEQ ID NO 162
<211> LENGTH: 20
<212> TYPE: DNA
<213> ORGANISM: Artificial Sequence
<220> FEATURE:
<223> OTHER INFORMATION: Synthetic DNA

<400> SEQUENCE: 162
cctccaactg ctcctactcg                                                 20

<210> SEQ ID NO 163
<211> LENGTH: 20
<212> TYPE: DNA
<213> ORGANISM: Artificial Sequence
<220> FEATURE:
<223> OTHER INFORMATION: Synthetic DNA

<400> SEQUENCE: 163
tcgaagcctc tgtgtccttt                                                 20

<210> SEQ ID NO 164
<211> LENGTH: 20
<212> TYPE: DNA
<213> ORGANISM: Artificial Sequence
<220> FEATURE:
<223> OTHER INFORMATION: Synthetic DNA

<400> SEQUENCE: 164
gaagttgtgg agggacgtgt                                                 20

<210> SEQ ID NO 165
<211> LENGTH: 20
<212> TYPE: DNA
<213> ORGANISM: Artificial Sequence
<220> FEATURE:
<223> OTHER INFORMATION: Synthetic DNA

<400> SEQUENCE: 165
```
gacttccagc agcttccatc 20

<210> SEQ ID NO 166
<211> LENGTH: 20
<212> TYPE: DNA
<213> ORGANISM: Artificial Sequence
<220> FEATURE:
<223> OTHER INFORMATION: Synthetic DNA

<400> SEQUENCE: 166
catgtactga gcaggccaga 20

<210> SEQ ID NO 167
<211> LENGTH: 20
<212> TYPE: DNA
<213> ORGANISM: Artificial Sequence
<220> FEATURE:
<223> OTHER INFORMATION: Synthetic DNA

<400> SEQUENCE: 167
aagatcttgg cagcgtttgt 20

<210> SEQ ID NO 168
<211> LENGTH: 20
<212> TYPE: DNA
<213> ORGANISM: Artificial Sequence
<220> FEATURE:
<223> OTHER INFORMATION: Synthetic DNA

<400> SEQUENCE: 168
ttgtgattga ggacgagcag 20

<210> SEQ ID NO 169
<211> LENGTH: 20
<212> TYPE: DNA
<213> ORGANISM: Artificial Sequence
<220> FEATURE:
<223> OTHER INFORMATION: Synthetic DNA

<400> SEQUENCE: 169 aatggttttcc cgctctaggt 20

<210> SEQ ID NO 170
<211> LENGTH: 20
<212> TYPE: DNA
<213> ORGANISM: Artificial Sequence
<220> FEATURE:
<223> OTHER INFORMATION: Synthetic DNA

<400> SEQUENCE: 170
ctcctgagac caaggctgtc 20

<210> SEQ ID NO 171
<211> LENGTH: 20
<212> TYPE: DNA
<213> ORGANISM: Artificial Sequence
<220> FEATURE:
<223> OTHER INFORMATION: Synthetic DNA

<400> SEQUENCE: 171
tgaaggtctc ggacaaatcc 20

<210> SEQ ID NO 172
<211> LENGTH: 20
<212> TYPE: DNA
<213> ORGANISM: Artificial Sequence
<220> FEATURE:
<223> OTHER INFORMATION: Synthetic DNA

<400> SEQUENCE: 172
ggaacgcctg tcagttgatt                                          20

<210> SEQ ID NO 173
<211> LENGTH: 20
<212> TYPE: DNA
<213> ORGANISM: Artificial Sequence
<220> FEATURE:
<223> OTHER INFORMATION: Synthetic DNA

<400> SEQUENCE: 173
ctcaaagcaa gcattggtga                                          20

<210> SEQ ID NO 174
<211> LENGTH: 20
<212> TYPE: DNA
<213> ORGANISM: Artificial Sequence
<220> FEATURE:
<223> OTHER INFORMATION: Synthetic DNA

<400> SEQUENCE: 174
tctgttcgct caggtccttt                                          20

<210> SEQ ID NO 175
<211> LENGTH: 20
<212> TYPE: DNA
<213> ORGANISM: Artificial Sequence
<220> FEATURE:
<223> OTHER INFORMATION: Synthetic DNA

<400> SEQUENCE: 175
tggtgtggtc agcttcagag                                          20

<210> SEQ ID NO 176
<211> LENGTH: 22
<212> TYPE: DNA
<213> ORGANISM: Artificial Sequence
<220> FEATURE:
<223> OTHER INFORMATION: Synthetic DNA

<400> SEQUENCE: 176
aaaaatggcc tgagttaagt gt                                       22

<210> SEQ ID NO 177
<211> LENGTH: 21
<212> TYPE: DNA
<213> ORGANISM: Artificial Sequence
<220> FEATURE:
<223> OTHER INFORMATION: Synthetic DNA

<400> SEQUENCE: 177
tcctcaattt ccctgtgttt g                                        21

<210> SEQ ID NO 178
<211> LENGTH: 20
<212> TYPE: DNA
<213> ORGANISM: Artificial Sequence
<220> FEATURE:
<223> OTHER INFORMATION: Synthetic DNA

<400> SEQUENCE: 178
tgcacactaa cagcatgacg                                          20

```
<210> SEQ ID NO 179
<211> LENGTH: 21
<212> TYPE: DNA
<213> ORGANISM: Artificial Sequence
<220> FEATURE:
<223> OTHER INFORMATION: Synthetic DNA

<400> SEQUENCE: 179
gaatttcttt cctctgcctg a                                              21

<210> SEQ ID NO 180
<211> LENGTH: 22
<212> TYPE: DNA
<213> ORGANISM: Artificial Sequence
<220> FEATURE:
<223> OTHER INFORMATION: Synthetic DNA

<400> SEQUENCE: 180
gggataaacc agacaagtag gc                                             22

<210> SEQ ID NO 181
<211> LENGTH: 20
<212> TYPE: DNA
<213> ORGANISM: Artificial Sequence
<220> FEATURE:
<223> OTHER INFORMATION: Synthetic DNA

<400> SEQUENCE: 181
ggacatgagc atggacatca                                                20
```

GENE RELATING TO ESTIMATION OF POSTOPERATIVE PROGNOSIS FOR BREAST CANCER

CROSS REFERENCE TO RELATED APPLICATIONS

This application is a divisional application of U.S. application Ser. No. 12/785,213 filed May 21, 2010, now abandoned, which was a divisional application of U.S. application Ser. No. 10/590,219, filed on Jan. 17, 2007, now abandoned, which was a National Stage of PCT/JP04/12455 filed Aug. 24, 2014 and claims the benefit of Japanese Patent Application No. JP 2004-048593, filed on Feb. 24, 2004. The contents of U.S. application Ser. No. 10/590,219; PCT/JP04/12455; and Japanese Patent Application No. JP 2004-048593 are incorporated by reference herein in their entireties.

TECHNICAL FIELD

The present invention relates to a gene correlated with prediction of the postoperative prognosis of breast cancer. Further, the present invention relates to a method of inspecting the postoperative prognosis of breast cancer using this gene, a method of screening cancer therapeutic medicines for controlling the postoperative prognosis of breast cancer, and a diagnosis kit for the postoperative prognosis of breast cancer.

BACKGROUND ART

Breast cancer is a disease situated as a superior cause for female lethality due to cancer, however, there are found still no dominant reasons for determining the grade of malignancy and survival prognosis from the biological standpoint.

The condition of an estrogen receptor (ER) is one determining element for clinical and biological symptoms of human breast cancer. Adjuvant hormone therapeutics is usually effective in ER-positive breast cancer patients irrespective of age, condition in the menopause, correlation with axillary nodes, and tumor diameter. However, ER-negative breast cancer is resistance to this therapeutic method (J Clin Oncology (2001) 19, 3817-1827, Breast Cancer (2001) 8, 298-304). Patients having an ER-negative tumor necessarily show the same response to chemical therapy. Since existent indices cannot classify breast cancer of this type depending on clinical symptom, the postoperative prognosis is recognized to be various (J Natl Inst (1991) 83, 154-155, J Natl Cancer Inst (2000) 93, 979-989).

Prognosis of breast cancer patients with no lymph node metastasis (node-negative breast cancer; n0) is better than that of metastatic breast cancer patients. However, in Japan, the present inventors have found that 16% of node-negative breast cancer patients relapse within 5 years after the initial operation (Clin Cancer Res (2000) 6, 3193-3198).

Prediction of the postoperative prognosis of breast cancer patients shows increasing in importance from the standpoint of adjuvant therapeutics currently utilizable. A gene marker which is useful in identifying patients showing a possibility of relapsing after an operation gives a merit which suitable preoperative adjuvant therapeutics can be applied to a high risk patient, and enables prevention of occurrence of unnecessary, complicated and uncomfortable side effects.

Conventionally, postoperative procedures for individual patients are determined depending on tumor diameter and the stage, metastasis to a lymph node, diagnosis by clinicopathological factors, search of a hormone receptor, and the like, however, they are not critical methods (Cancer (1982) 50, 2131-2138, Histopathology (1991) 19, 403-410, Int J Cancer (1996) 69, 135-141, Am J Clin Oncol (1997) 20, 546-551, Eur J Cancer (2002) 38, 1329-1334, Jpn J Cancer Res (2000) 91, 293-300).

Recently, there is a prognosis marker for postoperative breast cancer patients, intending determination of an importance of mutations of genes. These gene mutations include a mutation of p53 (Breast Cancer Res Treat (2001) 69, 65-68), loss of heterozygosity in several alleles (Int J Clin Oncol (2001) 6, 6-12), and abnormal expressions of a BRCA2 gene (Int J Cancer (2002) 198, 879-882), WT1 gene (Clin Cancer Res (2002) 8, 1167-1171), HER2/neu gene (Arch Surg (2000) 135, 1469-1474) and Ki-67 gene (J Pathol (1999) 187, 207-216). However, these would not be recognized as effective prognosis predicting means when taking into consideration a fact which a cancer is a disease owing to accumulation of abnormalities of multiple genes.

Further, in these years, genome projects in various organisms are being progressed, and a lot of genes and their base sequences typically including a human gene are being clarified quickly. The function of a gene having a clarified sequence can be checked by various methods. As one of the effective methods, known is a gene expression analysis method utilizing clarified base sequence information. For example, there are developed methods utilizing various nucleic acid-nucleic acid hybridization reactions and various PCR reactions as typified by Northern Hybridization, and relations between various genes and expressions of their organism functions can be checked by these methods. Though the number of applicable genes is limited in these methods, there have been developed a methodology and a novel analysis method called DNA microarray method (DNA chip method) enabling lump expression analysis of multiple genes, for carrying out comprehensive and systemic analysis of extremely many genes such as one individual level, as being clarified recently through genome projects.

As the DNA microarray, a lot of shapes are known such as that in which DNA synthesis is conducted on many discrete cells applying a lithography technology (U.S. Pat. No. 5,445, 934), that in which cells composed of grooves or holes are formed on a board and a probe is fixed to the inner wall of the cell (Tokkyo KOKAI (unexamined Japanese patent application) Nos. 11-108928, 2000-78998), a microarray in which a probe is fixed to a gel such as acrylamide and the like for increasing the amount of a probe to be fixed on a chip (U.S. Pat. No. 5,770,721, Tokkyo KOKAI No. 2000-60554), and the like.

Also known is a microarray obtained by fabricating a nucleic acid fixed gel retaining fiber array which retains a nucleic acid fixed gel, and cutting this array along a direction crossing the fiber axis of the array (Tokkyo KOKAI Nos. 2000-270878, 2000-270879).

Recent studies have found that a cDNA microarray technology is effective for identification of a novel gene marker for cancer diagnosis. To date, some researchers have carried out microarray analysis of breast cancer, however, there is no description about data of breast cancer gene expression property capable of predicting the postoperative prognosis of breast cancer (Proc Natl Acad Sci USA (1999) 96, 9212-9217, Nature (2000) 406, 747-752, Proc Natl Acad Sci USA (2001) 98, 11462-11467, Cancer Res (2001) 61, 5979-5984, Cancer Res (2000) 60, 2232-2238, Cancer Res (2001) 61, 5168-5178, Proc Natl Acad Sci USA (2001) 98, 10869-10874). As one exception, it is shown that a specific profile of a lymph node metastasis negative tumor gives a prediction of a short interval before progressing to distant metastasis (N Engl J Med (2002) 347, 1999-2009).

DISCLOSURE OF THE INVENTION

The present invention has an object of providing innovative means for predicting the postoperative prognosis of breast cancer patients from the standpoint of gene expression, based on results obtained by genome-wide and comprehensive analysis on gene expression in breast cancer.

The present inventors have comprehensively analyzed gene expression of a human gene by a DNA microarray and compared gene expression functions of breast cancers in various conditions, thereby, establishing a system for predicting the postoperative prognosis of breast cancer.

That is, the present invention provides the following genes (groups) (1) to (8).

(1) A gene consisting of at least one of the following definitions correlated with prediction of the postoperative prognosis of breast cancer;
1) a marker gene group capable of establishing classification of genes from breast cancer patients died within 5 years after a surgical operation (5y-D group) and genes from patients survived free of disease for several years or more after the operation (5y-S group), depending on their expression functions, in estrogen receptor-negative breast cancer,
2) a marker gene group capable of establishing classification of genes from n0 breast cancer patients recurred within 5 years after an operation (5Y-R group) and genes from patients survived free of disease for 5 years or more after the operation (5Y-F group), depending on their expression functions, in (node-negative)(n0) breast cancer with no metastasis to a lymph node in the operation,
3) a marker gene group capable of establishing classification of genes from breast cancer patients died within 5 years after a surgical operation (5D group) and genes from patients survived free of disease for several years or mere after the operation (5S group), depending on their expression functions, in primary breast cancer.

(2) A gene selected from the following sequences correlated with prediction of the postoperative prognosis of primary breast cancer;
pro-alpha-1 type 3 collagen (PIIIP),
complement component Clr,
dihydropyrimidinase-like 3 (DPYSL3),
protein tyrosine kinase 9-like (PTK9L),
carboxypeptidase E (CPE),
alpha-tubulin,
beta-tubulin,
heat shock protein HSP 90-alpha gene,
malate dehydrogenase,
NADH dehydrogenase (ubiquinone) 1 beta subcomplex, 3 (NDUFB3).

(3) A gene selected from the following sequences highly expressed in a group of good prognosis correlated with prediction of the postoperative prognosis of primary breast cancer;
pro-alpha-1 type 3 collagen (PIIIP),
complement component Clr,
dihydropyrimidinase-like 3 (DPYSL3),
protein tyrosine kinase 9-like (PTK9L),
carboxypeptidase E (CPE),
alpha-tubulin,
beta-tubulin.

(4) A gene selected from the following sequences highly expressed in a group of bad prognosis correlated with prediction of the postoperative prognosis of primary breast cancer;
heat shock protein HSP 90-alpha gene,
malate dehydrogenase,
NADH dehydrogenase (ubiquinone) 1 beta subcomplex, 3 (NDUFB3).

(5) A gene selected from the following sequences correlated with prediction of the postoperative prognosis, in (node-negative)(n0) breast cancer with no metastasis to a lymph node in operation;
AF058701/DNA polymerase zeta catalytic subunit (REV3),
AI066764/lectin, galactoside-binding, soluble, 1 (galectin 1),
x15940/ribosomal protein L31,
Hs.94653/neurochondrin (KIAA0607),
M13436/ovarian beta-A-inhibin,
Hs.5002/copper chaperone for superoxide dismutase; CCS,
D67025/proteasome (prosome, macropain) 26S subunit, non-ATPase, 3,
M80469/MHC class I HLA-J gene,
Hs.4864/ESTs,
Hs.106326/ESTs.

(6) A gene selected from the following sequences highly expressed in a group of bad prognosis correlated with prediction of the postoperative prognosis, in (node-negative)(n0) breast cancer with no metastasis to a lymph node in operation;
AF058701/DNA polymerase zeta catalytic subunit (REVS),
AI066764/lectin, galactoside-binding, soluble, 1 (galectin 1),
x15940/ribosomal protein L31.

(7) A gene selected from the following sequences highly expressed in a group of good prognosis correlated with prediction of the postoperative prognosis, in (node-negative)(n0) breast cancer with no metastasis to a lymph node in operation;
Hs.94653/neurochondrin (KIAA0607),
M13436/ovarian beta-A-inhibin,
Hs.5002/copper chaperone for superoxide dismutase; CCS,
D67025/proteasome (prosome, macropain) 26S subunit, non-ATPase, 3,
M80469/MHC class I HLA-J gene,
Hs.4864/ESTs,
Hs.106326/ESTs.

(8) A gene selected from the following sequences correlated with prediction of the postoperative prognosis, in estrogen receptor-negative breast cancer;
Hs.108504/FLJ20113/ubiquitin-specific protease otubain 1
Hs.146550/MYH9/myosin, heavy polypeptide 9, non-muscle
Hs.194691/RAI3/retinoic acid induced 3
Hs.1975/TDRD3/tudor domain containing 3
Hs.203952/TRRAP/transformation/transcription domain-associated protein
Hs.278607/GSA7/ubiquitin activating enzyme E1-like protein
Hs.429/ATP5G3/
ATP synthase, H+ transporting, mitochondrial F0complex, subunitc (subunit9) isoform3
Hs.75305/AIP/aryl hydrocarbon receptor interacting protein
Hs.81170/PIM1/pim-1 oncogene
Hs.99987/ERCC2/
excision repaircross-complementingrodentrepairdeficiency,
complementationgroup2
Y12781/Transducin (beta) like 1 protein
Hs.104417/KIAA1205 protein
cl.21783/Hypothetical protein
Hs.112628/Hypothetical protein: MGC43581
Hs.170345/Hypothetical protein FLJ13710
Hs.53996/weakly similar to zinc finger protein 135
Hs.55422/Hypothetical protein Hs.112718/EST
Hs.115880/EST
Hs.126495/EST The present invention also provides a gene selected from the above-mentioned (8), as a gene highly expressed in a group of bad prognosis.

Further, the present invention provides a DNA microarray carrying thereon the gene according to any one of the above-mentioned (1) to (8) and/or a probe specific to the gene, and preferably, the DNA microarray is a fiber type microarray.

The above-mentioned gene and/or probe specific to the gene can be used as a marker in a method of inspecting the postoperative prognosis of breast cancer. Further, it can be also used as a marker for cancer therapeutic medicines for controlling the postoperative prognosis of breast cancer. The above-mentioned microarray can be used in a method of inspecting the postoperative prognosis of breast cancer.

Further, the present invention provides a method of screening cancer therapeutic medicines for controlling the postoperative prognosis of breast cancer using as a marker the above-mentioned gene and/or probe specific to the gene. The above-mentioned microarray can be used in the above-mentioned screening method.

The marker can be included as a reagent, and can be used as a diagnosis kit for the postoperative prognosis of breast cancer. The reagent kit includes a DNA microarray carrying thereon a marker, preferably, a fiber type microarray.

According to the means of the present invention, completely novel breast cancer correlated genes have been found and simultaneously, it has been found that these genes are correlated deeply with malignant degeneration of breast cancer and finally, exert an influence on the prognosis of breast cancer patients. Further, by establishing a mathematical formula for evaluating expression condition of the found gene, a completely novel and effective breast cancer postoperative prognosis predicting system has been developed. The system of the present invention from the standpoint of gene expression is believed to be an innovative prognosis predicting system arresting biological essentiality of a cancer, utterly different from conventional prognosis evaluation methods, when taking into consideration a fact which a cancer is a disease owing to abnormality of a gene.

BRIEF DESCRIPTION OF DRAWINGS

The patent or application file contains at least one drawing executed in color. Copies of this patent or patent application publication with color drawing(s) will be provided by the office upon request and payment of the necessary fee.

FIG. 2 is a photograph showing analysis results of semi-quantitative RT-PCR of RNAs derived from 5y-S group and 5y-D group.

FIG. 9 shows results illustrating prognosis indices (PI) of newly inspected 20 cases. The indices of all 10 patients survived free of disease for 5 years or more were higher than 7. On the other hand, the indices of patients died of breast cancer within 5 years after operation were lower than 7. Distribution of two groups is statistically significant (p=0.0002).

BEST MODE FOR CARRYING OUT THE INVENTION

Figures 1, 1A:
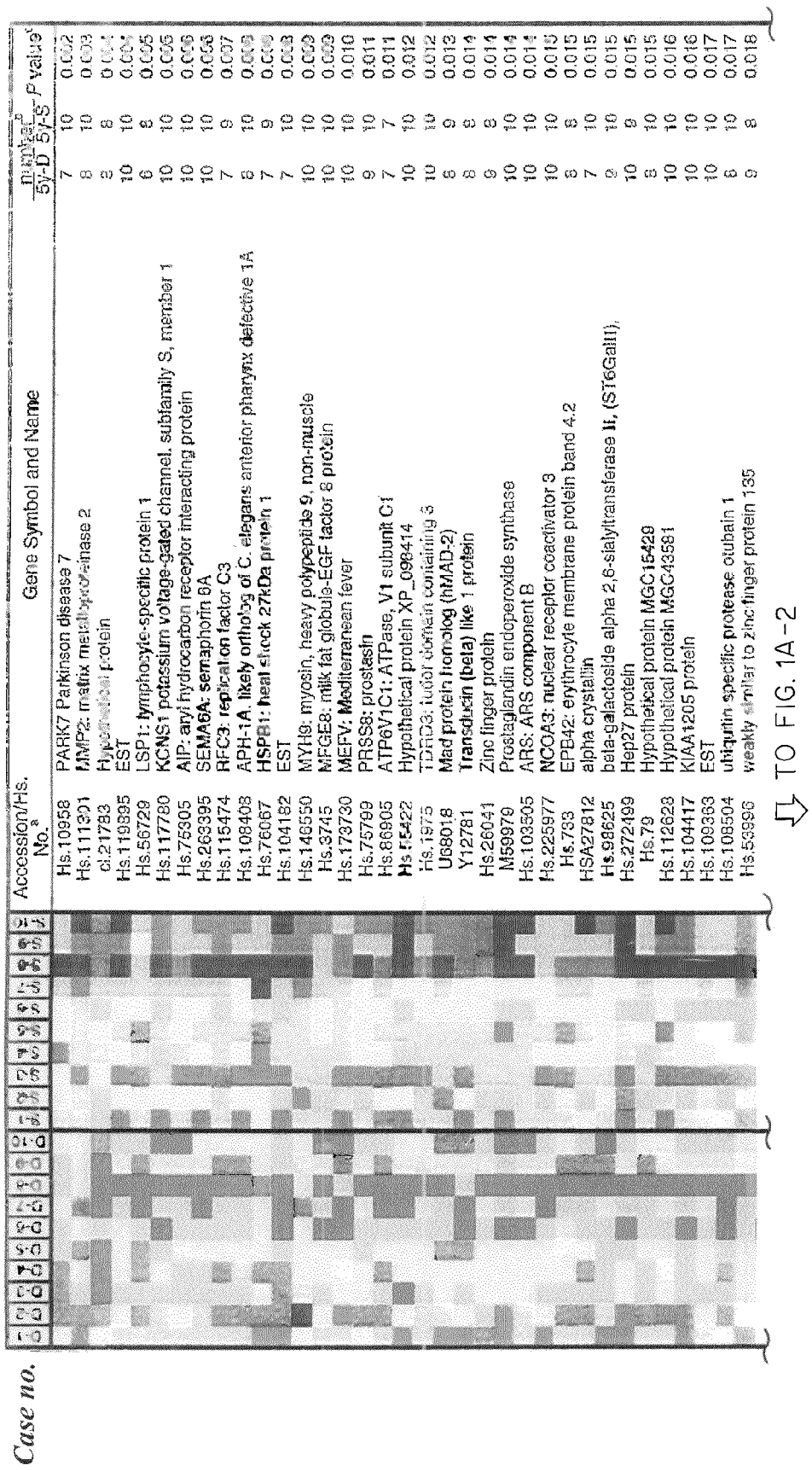
FIG. 1A-1 and FIG. 1A-2 are photographs showing a gene group (A) manifesting increase in expression in 5y-D group as compared with 5y-S group.

The marker gene group correlated with prediction of the postoperative prognosis of breast cancer as one aspect of the present invention is obtained by analysis by cDNA microarray of the expression functions of genes from patients manifesting death or recurring within 5 years after a surgical operation and patients survived for 5 years or more after the operation, in estrogen receptor-negative breast cancer, node-negative breast cancer and primary breast cancer.

Specifically, one aspect of the present invention is a gene consisting of at least one of the following definitions selected from known sequences correlated with prediction of the postoperative prognosis of breast cancer;

1) a marker gene group capable of establishing classification of genes from breast cancer patients died within 5 years after a surgical operation (5y-D group) and genes from patients survived free of disease for several years or more after the operation (5y-S group), depending on their expression functions, in estrogen receptor-negative breast cancer, 2) a marker gene group capable of establishing classification of genes from n0 breast cancer patients recurred within 5 years after an operation (5Y-R group) and genes from patients survived free of disease for 5 years or more after the operation (5Y-F group), depending on their expression functions, in (node-negative)(n0) breast cancer with no metastasis to a lymph node in the operation, 3) a marker gene group capable of establishing classification of genes from breast cancer patients died within 5 years after a surgical operation (5D group) and genes from patients survived free of disease for several years or more after the operation (5S group), depending on their expression functions, in primary breast cancer.

The gene correlated with prediction of the postoperative prognosis of breast cancer of the present invention is obtained by evaluating the data of a cDNA microarray using a Random-permutation test and a Mann-Whitney test. The present invention presents an approach more useful at clinical level, by evaluating gene expression functions by a combination of a cDNA microarray and a semi-quantitative PCR experiment.

In the present invention, a gene correlated with prediction of the postoperative prognosis of primary breast cancer has been identified by evaluating gene expression functions in breast cancer patients.

Specifically, one aspect of the present invention is a gene selected from the following sequences selected from known sequences correlated with prediction of the postoperative prognosis of primary breast cancer;
pro-alpha-1 type 3 collagen (PIIIP),
complement component C1r,
dihydropyrimidinase-like 3 (DPYSL3),
protein tyrosine kinase 9-like (PTK9L),
carboxypeptidase E (CPE),
alpha-tubulin,
beta-tubulin,
heat shock protein HSP 90-alpha gene,
malate dehydrogenase,
NADH dehydrogenase (ubiquinone) 1 beta subcomplex, 3 (NDUFB3).

In the present invention, "high expression" means that the expression level of a subject gene is, when compared with the average value of the expression levels of the same gene in a parent population, higher than the average value, for example, 2-fold or more of the average value.

In the present invention, "low expression" means that the expression level of a subject gene is, when compared with the average value of the expression levels of the same gene in a parent population, lower than the average value, for example, 2-fold or less of the average value.

Some of the above-mentioned genes are believed to be correlated with proliferation or distant metastasis of tumor cells, and for example, a heat shock protein HSP 90-alpha is a chaperone for a lot of kinases, and has a possibility of promoting growth of cancer cells (Neckers, L (2002) Trends Mol Med 8, S55-61). Malate dehydrogenase is an important enzyme correlated with energy accompanying aerobic or anaerobic metabolism, and the activity of malate dehydrogenase is correlated with a tumor marker for squamous cell carcinoma (Ross, C. D., et al. (2000) Otolaryngol Head Neck Surg 122, 195-200). NADH dehydrogenase (ubiquinone) 1 beta subcomplex, 3(NDUFB3) belongs to an mitochondrial electron transport chain, and chromosome abnormality in a region containing NDUFB3 is remarkable in a breast cancer cell line MDA-MB-231 (Xie, et al. (2002) Int J Oncol 21, 499-507).

The above-mentioned 10 genes correlated with prediction of the postoperative prognosis of primary breast cancer show different expressions in a group of good prognosis (5S group) and a group of bad prognosis (5Y group), and 7 genes among the 10 genes are genes highly expressed in a group of good prognosis (5S group).

Namely, one aspect of the present invention is a gene selected from the following sequences highly expressed in a group of good prognosis selected from known sequences correlated with prediction of the postoperative prognosis of primary breast cancer;
pro-alpha-1 type 3 collagen (PIIIP),
complement component C1r,
dihydropyrimidinase-like 3 (DPYSL3),
protein tyrosine kinase 9-like (PTK9L),
carboxypeptidase E (CPE),
alpha-tubulin,
beta-tubulin.

3 genes among the 10 genes correlated with prediction of the postoperative prognosis of primary breast cancer are genes highly expressed in a group of bad prognosis (5Y group). Namely, one aspect of the present invention is a gene selected from the following sequences highly expressed in a group of bad prognosis selected from known sequences correlated with prediction of the postoperative prognosis of primary breast cancer; heat shock protein HSP 90-alpha gene, malate dehydrogenase,
NADH dehydrogenase (ubiquinone) 1 beta subcomplex, 3 (NDUFB3).

Here, the prediction index (PI) for primary breast cancer is defined as described below and can be used for prediction of the postoperative prognosis of breast cancer.

Prediction index (PI)=(total of normalized expression ratios of the above-mentioned 7 genes highly expressed in a group of good prognosis in breast cancer tissue)−(total of normalized expression ratios of the above-mentioned 3 genes highly expressed in a group of bad prognosis in breast cancer tissue)

In the present invention, gene expression functions in breast cancer patients have been evaluated and 10 genes correlated with prediction of the postoperative prognosis of node-negative breast cancer have been identified.

Specifically, one aspect of the present invention is a gene selected from the following sequences selected from known sequences correlated with prediction of the postoperative prognosis, in (node-negative)(n0) breast cancer with no metastasis to a lymph node in operation;
AF058701/DNA polymerase zeta catalytic subunit (REV3),
AI066764/lectin, galactoside-binding, soluble, 1 (galectin 1),
x15940/ribosomal protein L31,
Hs.94653/neurochondrin (KIAA0607),
M13436/ovarian beta-A-inhibin,
Hs.5002/copper chaperone for superoxide dismutase; CCS,
D67025/proteasome (prosome, macropain) 26S subunit, non-ATPase, 3,
M80469/MHC class I HLA-J gene,
Hs.4864/ESTs,
Hs.106326/ESTs.

The above-mentioned genes correlated with prediction of the postoperative prognosis of node-negative breast cancer include genes correlated with proliferation and distant metastasis of tumor cells. For example, galectin 1 is an autocrine type cancer repressor for regulating cell differentiation (AxelH, et al. (2003) Int. J. Cancer, 103: 370-379). Further, a gene activating cancer metastasis is included.

The above-mentioned 10 genes correlated with prediction of the postoperative prognosis of node-negative breast cancer show different expressions in a group of good prognosis (5Y-F group) and a group of bad prognosis (5Y-R group), and 3 genes among the genes are genes highly expressed in a group of bad prognosis (5Y-R group). Namely, one aspect of the present invention is a gene selected from the following sequences highly expressed in a group of bad prognosis selected from known sequences correlated with prediction of the postoperative prognosis, in node-negative breast cancer in operation;
AF058701/DNA polymerase zeta catalytic subunit (REV3),
AI066764/lectin, galactoside-binding, soluble, 1 (galectin 1),
x15940/ribosomal protein L31.

7 genes among the 10 genes correlated with prediction of the postoperative prognosis of node-negative breast cancer are genes highly expressed in a group of good prognosis (5Y-F group). Namely, one aspect of the present invention is a gene selected from the following sequences highly expressed in a group of good prognosis selected from known sequences correlated with prediction of the postoperative prognosis, in node-negative breast cancer;
Hs.94653/neurochondrin (KIAA0607),
M13436/ovarian beta-A-inhibin,
Hs.5002/copper chaperone for superoxide dismutase; CCS,
D67025/proteasome (prosome, macropain) 26S subunit, non-ATPase, 3, M80469/MHC class I HLA-J gene,
Hs.4864/ESTs,
Hs.106326/ESTs.

Here, the prognosis score (PS) for node-negative breast cancer is defined as described below and can be used for prediction of the postoperative prognosis of breast cancer.

Prognosis score (PS)=(total of normalized expression ratios of the above-mentioned 3 genes highly expressed in a group of bad prognosis in breast cancer tissue)−(total of normalized expression ratios of the above-mentioned 7 genes highly expressed in a group of good prognosis in breast cancer tissue).

In the present invention, 20 genes correlated with prediction of the postoperative prognosis of estrogen receptor-negative breast cancer have been identified, by evaluating gene expression functions in breast cancer patients.

Specifically, one aspect of the present invention is a gene selected from the following sequences selected from known sequences correlated with prediction of the postoperative prognosis, in estrogen receptor-negative breast cancer;
Hs.108504/FLJ20113/ubiquitin-specific protease otubain 1
Hs.146550/MYH9/myosin, heavy polypeptide 9, non-muscle
Hs.194691/RAI3/retinoic acid induced 3
Hs.1975/TDRD3/tudor domain containing 3
Hs.203952/TRRAP/transformation/transcription domain-associated protein
Hs.278607/GSA7/ubiquitin activating enzyme E1-like protein
Hs.429/ATP5G3/ATP synthase, H+ transporting, mitochondrial F0complex, subunitc (subunit9) isoform3
Hs.75305/AIP/aryl hydrocarbon receptor interacting protein
Hs.81170/PIM1/pim-1 oncogene
Hs.99987/ERCC2/
excisionrepaircross-complementingrodentrepairdeficiency,
complementationgroup2
Y12781/Transducin (beta) like 1 protein
Hs.104417/KIAA1205 protein
cl.21783/Hypothetical protein
Hs.112628/Hypothetical protein: MGC43581
Hs.170345/Hypothetical protein FLJ13710
Hs.53996/weakly similar to zinc finger protein 135
Hs.55422/Hypothetical protein
Hs.112718/EST
Hs.115880/EST
Hs.126495/EST The above-mentioned genes correlated with prediction of the postoperative prognosis of estrogen receptor-negative breast cancer include genes correlated with proliferation and distant metastasis of tumor cells. For example, PIM1 is serine/threonine kinase, and there is a correlation between clinical results of prostate cancer and the expression (Oesterreich, S., et al. (1996) Clin Cancer Res, 2, 1199-1206). TRRAP protein is a subunit of a mammal HTA complex, and antisense RNA against TRRAP inhibits estrogen-dependent growth of breast cancer cells.

The above-mentioned 20 genes correlated with prediction of the postoperative prognosis of estrogen receptor-negative breast cancer show high expression in a group of bad prognosis (5y-D group). Namely, one aspect of the present invention is a gene selected from known sequences correlated with prediction of the postoperative prognosis, in the above-mentioned estrogen receptor-negative breast cancer highly expressed in a group of bad prognosis.

Here, postoperative prognosis of breast cancer can be predicted as described below, based on the expression of the above-mentioned gene correlated with prediction of the postoperative prognosis of estrogen receptor-negative breast cancer;

(1) when the expression levels in breast cancer tissue of the above-mentioned 20 genes correlated with prediction of the postoperative prognosis of estrogen receptor-negative breast cancer are compared with the average value in a parent population, and if the expression level of each gene is 2-fold or more of the average value in a parent population, one point is imparted, (2) when the procedure of (1) is carried out on 20 genes, and if the total point is 8 points or more, prognosis is decided to be bad.

The above-mentioned gene correlated with prediction of the postoperative prognosis of breast cancer can be used as a marker for inspection of breast cancer postoperative prognosis. Namely, one aspect of the present invention is a method of inspecting the postoperative prognosis of breast cancer using the above-mentioned gene as a marker.

The above-mentioned gene correlated with prediction of the postoperative prognosis of breast cancer can be used as a marker for screening of cancer therapeutic medicines for controlling the postoperative prognosis of breast cancer. Namely, one aspect of the present invention is a method of screening cancer therapeutic medicines for controlling the postoperative prognosis of breast cancer using the above-mentioned gene as a marker.

The above-mentioned gene correlated with prediction of the postoperative prognosis of breast cancer can be used as a marker for diagnosis of the postoperative prognosis of breast cancer. It is also possible to design probes specific to the above-mentioned gene and to use these probes as a marker. These probes can be designed, for example, by Probe Quest (registered trademark) manufactured by Dyna Com. Namely, one aspect of the present invention is a diagnosis kit for the postoperative prognosis of breast cancer containing a reagent using the above-mentioned gene as a marker.

The above-mentioned diagnosis kit can include a microarray. Namely, one aspect of the present invention is the diagnosis kit, wherein the diagnosis kit includes a microarray.

The microarray of the above-mentioned diagnosis kit including a microarray includes a fiber type microarray. Here, for a method of preparing a fiber type microarray, the above-mentioned patent documents 6 to 7 are cited. Namely, one aspect of the present invention is the above-mentioned diagnosis kit wherein the microarray is a fiber type microarray.

Next, aspects of the present invention will be specifically illustrated by examples, but the present invention is not limited to these examples.

Example 1

Evaluation of Gene Expression Function for Prediction of the Postoperative Prognosis in Estrogen Receptor-Negative Breast Cancer
(Tissue Sample)

An informed consent was obtained according to a guide line accepted by an ethics committee of Cancer Society and by Nippon Medical School, then, primary breast cancer and tissue from adjacent normal mammary gland were collected from breast cancer patients who undergone an operation in 1995 to 1997 in Cancer Society attached hospital (Tokyo). The tissue was quickly frozen and preserved at −80° C. For 954 patients, all members were clinically traced during a period of 5 years or more or until death, and samples were selected from 10 estrogen receptor-negative breast cancer patients died within 5 years after the operation (5y-D) and 10 patients survived free of disease for 5 years or more after the operation (5y-S). The backgrounds of both the patient groups were allowed to coincide in age, lymph node metastasis, tumor diameter and tissue type (Table 1).
(Clinical Feature of 20 Cases of Breast Cancer)

TABLE 1

| group | Case No. | ER condition | Age | Sex | Process[a] | TNM classification[b] Tumor | Lymph node | TTD[c] |
|---|---|---|---|---|---|---|---|---|
| 5y-D | 3281 | Negative | 34 | Female | a2 | T2 | N1b | 9 |
|  | 3459 | Negative | 64 | Female | a2 | T4 | N3 | 6 |
|  | 3550 | Negative | 73 | Female | a2 | T4 | N1b | 12 |
|  | 3892 | Negative | 62 | Female | a2 | T2 | N1a | 21 |
|  | 3948 | Negative | 60 | Female | a2 | T2 | N1a | 51 |
|  | 4020 | Negative | 50 | Female | a2 | T2 | N3 | 28 |
|  | 3654 | Negative | 46 | Female | a2 | T4 | N1b | 19 |
|  | 4118 | Negative | 53 | Female | a2 | T1 | N1a | 21 |
|  | 4462 | Negative | 34 | Female | a1 | T2 | N1a | 24 |
|  | 4126 | Negative | 51 | Female | b5 | T4 | N3 | 6 |
| 5y-S | 3656 | Negative | 31 | Female | a2 | T2 | N1a | >60 |
|  | 3197 | Negative | 42 | Female | a1 | T1 | N1a | >60 |
|  | 3662 | Negative | 58 | Female | a2 | T2 | N0 | >60 |
|  | 3241 | Negative | 47 | Female | a2 | T2 | N1a | >60 |
|  | 3267 | Negative | 51 | Female | a2 | T2 | N1a | >60 |
|  | 3329 | Negative | 60 | Female | a2 | T2 | N1a | >60 |
|  | 3345 | Negative | 43 | Female | a1 | T2 | N2 | >60 |
|  | 3556 | Negative | 59 | Female | a2 | T3 | N0 | >60 |
|  | 3558 | Negative | 57 | Female | a2 | T3 | N1b | >60 |
|  | 3658 | Negative | 42 | Female | a1 | T2 | N1a | >60 |

[a]a1: invasive papillotubular carcinoma. a2: invasive solid-tubular carcinoma. b5: squamous cell carcinoma.
[b]TNM classification: clinical classification by Japan Breast Cancer Society
[c]TTD: time to death after surgery (months)

All patients underwent postoperative adjuvant therapy according to "Postoperative clinical protocol for breast cancer (nyugan no tameno shujutsugo no rinsho no purotokoru)" of Cancer Society attached hospital. In each case, selection of adjuvant therapy was determined strictly based on surgical operation type, lymph node involvement condition, and presence of local or distant metastasis. In the study of the present invention, all patients did not have distant metastasis before the adjuvant chemical therapy and did not undergo radiation therapy or chemical therapy before the surgical operation.
(Clinicopathological Parameter)

The following parameters were checked: tissue type, tumor diameter and invasion (t factor), lymph node involvement, and conditions of estrogen receptor (ER) and progesterone receptor (PgR). Tumors were classified into the following types according to TNM classification and to tissue classification of Japan Breast Cancer Society (1989); noninvasivetubular (1a), invasivepapillotubular (a1), invasive solid-tubular (a2), invasivescirrhouscarcinoma (a3), and other special types (b). The classification is basically the same as breast cancer tissue classification of WHO. t factors were classified into the following types according to histological TNM classification; tumor with a maximum size of 2 cm or less (t1), tumor with no Invasion into skin or pectoral muscle and with a maximum size of 2 cm or more (t2), and tumor with invasion into skin or pectoral muscle (t3).
(Design and Construction of cDNA Microarray)

From 25344 cDNAs selected from UniGene database, "genome wide cDNA microarray" was constructed. The cDNAs were made by RT-PCR using poly(A)+ RNAs separated from various human organs. The PCR products were spotted on slide glasses of type 7 (Amersham Biosciences UK Limited, Buckinghamshire, UK) using Array Spotter Generation III (Amersham Biosciences). Each slide contains 384 house-keeping genes.

(Preparation and Proliferation of RNA)
A tumor raw material was quickly frozen at −80° C. immediately after collection. RNA was extracted using TRIzol (Invitrogen Inc., Carlsbad, Calif., USA), further, purified using RNeasykits (Quiagen Inc., Valencia, Calif.). The purity of each RNA was evaluated by a spectrophotometry and electrophoresis on 1.2% modified formamide gel. The high purity RNA was defined as a sample having an absorbance ratio (260 nm/280 nm) of 1.8 to 2.0 and in which 28S/18S liposomal bands show a ratio of 1.8 or more on formamide gel electrophoresis. After treating with 1 unit of DNaseI (Epicentre Technologies, Madison, Wis.) (1 unit/μl), RNA amplification by T7RNA polymerase was carried out using 2 μg of RNA from each sample as a starting raw material. Amplification was carried out twice, and the amplified RNA (aRNA) was purified by RNeasykits (Quiagen Inc., Valencia, Calif.). The amount of each aRNA was measured by a spectrophotometer, and the quality was checked by formamide gel electrophoresis.
(Labeling of aRNA, Hybridization and Scanning)

cDNA for microarray analysis was prepared from aRNA. aRNAs (5 to 10 μg) from breast cancer and normal mammary gland tissue were labeled with Cy5 (cancer sample) and Cy3 (normal sample) using aminoallyl-cDNA labelingkits (Ambion, Austin, Tex.). The Cy3-labeled cDNA probe and the Cy5-labeled cDNA probe were mixed and heated at 95° C. for 5 minutes, then, quenched with ice for 30 seconds, and hybridized on a microarray. The mixed probes were added to formamide (Sigma-Aldrich Corp., St. Louis, Mo., USA) having a 50% final concentration of microarrayhybridization solution version 2 (Amersham Biosciences UK Limited, Buckinghamshire, UK). After hybridization at 40° C. for 15 hours, the microarray slides were washed first with 1×SSC and 0.2% SDS at 55° C. for 10 minutes, then, washed twice with 0.1×SSC/0.2% SDS each for 1 minute at room temperature. All treatments were carried out by Automated Slide Processor System (Amersham). The signal strength of each hybridization was scanned by Gene Pix 4000A (Axon Instruments, Inc., Foster City, Calif., USA), and evaluated by Gene Pix 3.0 (Axon Instruments) by a spectrophotometry. The scanned signals were normalized by a method described in the following literature (the total gene normalization method) (Yang Y H, Dudoit S, Luu P, et al. (2002) Nucleic Acids Res 30, e15; Manos E J, Jones D A. (2001) Cancer Res 61: 433-348).

(Signal Analysis and Selection of Genes Showing Different Expressions)

The signal strength of each hybridization was evaluated by a photometry by Gene Pix 3.0 (Axon Instruments, Inc., Foster City, Calif., USA). For normalizing mRNA expression levels between cancer and control, the Cy5:Cy3 ratio in each gene expression was adjusted. As a result, the averaged Log (Cy5: Cy3 ratio) of the house keeping genes was zero. 27 house keeping genes were adopted from a house-keeping panel in Web site http://www.nhgri.nih.gov/DIR/LCG/ARRAY/exp-n.html. For each microarray slide, the cut off value of (S/N) ratio was set at 3.0. Genes with signal strengths of Cy3 and Cy5 lower than the cut off value were excluded out of the investigation.

(Mann-Whitney Test)

For investigating genes showing apparently different expressions between 5y-D tumor and 5y-S tumor, Mann-Whitney test was applied to a series of samples X. X represents Cy5/Cy3 signal strength ratio of each gene and each sample (Ono K, Tanaka T, Tsunoda T, et al. (2000) Cancer Res 2000; 60: 5007-5011). The U value was calculated for genes imparting significant signals in at least 5 samples in both groups. Genes showing U values of lower than 23 or larger than 77 were selected. Since the U value is obtained by calculation for 5y-S group based on 5y-D group in each gene based on each X value, U values lower than 23 were evaluated to manifest higher expression in 5y-S group than in 5y-D group. However, genes with U values higher than 77 were evaluated to manifest higher expression in 5y-D group than in 5y-S group. Base on this criterion, 183 genes were highly expressed in 5y-S group and 31 genes were highly expressed in 5y-S group. Thus, only genes in which intermediate expression values show a difference of 2-fold or more between two groups ($\mu XD/\mu XS \leq 0.5$ or $\geq 2.0$, $\mu XD$ and $\mu XS$ represent average X values in 5y-D and 5y-S group, respectively) were defined as genes correlated with prognosis. As a result, 110 genes in total were selected. Of them, 90 genes were expressed at higher level in 5y-D tumor group and 20 genes were expressed at higher level in 5y-S tumor group.

(Random-Permutation Test)

Further, for evaluating values of 110 genes selected by the Mann-Whitney test, a permutation test was carried out. A possibility, Ps of a gene for correlating with a group difference was also assumed. When each gene is represented by an expression vector $v(g)=(X1, X2, ---, X20)$ (Xi shows a gene expression level of i-th sample in the first sample group), an ideal expression pattern is expressed by $c=(c1, c2, ---, c20)$ ($ci=+1$ or $0$, depending on whether i-th sample belongs to S group or D group).

Correlation between a gene and a group difference Pgc was defined as described below. That is, $Pgc=(\mu_S-\mu_D)/(\delta_S+\delta_D)$; $\mu_S(\mu_D)$ and $\delta_S(\delta_D)$ show standard deviation of $\log_2 X$ of the gene "g" of each sample in a newly defined S (or D) gimp.

The permutation test was carried out while substituting the coordinate of c. The correlation values, Pgc were calculated between all permutations. These procedures were repeated for 10000 times. Accidentally, the p value showing a possibility of a gene for classifying two groups was evaluated for each of 110 genes selected. Finally, 71 gene highly expressed in 5y-D case and 15 gene expressed low in 5y-S case were selected.

(Semi-Quantitative RT-PCR)

RNA (2 µg) was treated with DNase I (Epicentre Technologies, Madison, Wis., USA), and single-stranded cDNAs were subjected to reverse transcription using Reverscript IIreverse-transcriptase (manufactured by Wako Pure Chemical Industries, Ltd., Osaka, Japan) and oligo (dT) 12-18 primer. Single-stranded cDNAs were adjusted in the concentration for the subsequent PCR amplification by monitoring expression of GAPD (glyceraldehyde-3-phosphatedehydrogenase) as a quantitative control. Each PCR was carried out under the following reaction conditions using Gene Amp PCR system 9700 (Applied Biosystems, Foster City, Calif., USA) at an amount of 1×PCR buffer of 30 µl.

94° C. 5 minutes, (94° C. 30 seconds, 60° C. 30 seconds, and 72° C. 30 seconds) for 25 to 35 cycles.

Primer sequences used in RT-PCR are as described below:

```
GAPD (control) forward,
                                       SEQ ID No. 1
5'-GGA AGGTGA AGG TCG GAG T-3' reverse,
                                       SEQ ID No. 2
5'-TGG GTG GAA TCA TAT TGGAA-3';

Hs.108504F,
                                       SEQ ID No. 3
5'-ACA CTT CAT CTG CTCCCT CAT AG-3';

Hs.108504R,
                                       SEQ ID No. 4
5'CTG CCT AGA CCT GAGGAC TGT AG-3';

Hs.146550F,
                                       SEQ ID No. 5
5'ACT GAG GCC TTT TGGTAG TCG-3';

Hs.146550R,
                                       SEQ ID No. 6
5'TCT CTT TAT TGT GATGCT CAG TGG-3';

Hs.76607F,
                                       SEQ ID No. 7
5'AAA TCC TTC TCG TGT GTTGAC TG-3';

Hs.76607R,
                                       SEQ ID No. 8
5'CAG TCA TGA GGG CTA AAAACT GA-3';

Hs.1975F,
                                       SEQ ID No. 9
5'GAA GAC AAC AAG TTT TAC CGG G-3';

Hs.1975R,
                                       SEQ ID No. 10
5'ATG GTT TTA TTG ACG GCAGAA G-3';

Hs.203952F,
                                       SEQ ID No. 11
5'AGG ACA CGT CCT CTCCTC TCT C-3';

Hs.203952R,
                                       SEQ ID No. 12
5'TAA AGC TAG CGA AGGAAC GTA CA-3';

Hs.278607F,
                                       SEQ ID No. 13
5'TCC CTT CTG TTT CCT CAG TGT T-3';

Hs.278607R,
                                       SEQ ID No. 14
5'CCT GCC CCG ATA AAA ATA TCT AC-3';
```

-continued

Hs.429F,
SEQ ID No. 15
5'TTG ACC TTA AGC CTC TTTTCC TC-3';

Hs.429R,
SEQ ID No. 16
5'ATA ACG TAC ATT CCC ATGACA CC-3';

Hs.75305F,
SEQ ID No. 17
5'ACT TTC AAG ATG GGACCA AGG-3';

Hs.75305R,
SEQ ID No. 18
5'ATA TAC ACA GAA GCATGA CGC AG-3';

Hs.81170F,
SEQ ID No. 19
5'TTG CTG GAC TCT GAAATA TCC C-3';

Hs.81170R,
SEQ ID No. 20
5'TTC CCC TGT ACA GTATTT CAC TCA-3';

Hs.99987F,
SEQ ID No. 21
5'CTG AGC AAT CTG CTCTAT CCT CT-3';

Hs.99987R,
SEQ ID No. 22
5'GTT CCA GAT TCG TGAGAA TGA CT-3';

Y12781F,
SEQ ID No. 23
5'ACC AGT AAC AAC TGT GGGATG G-3';

Y12781R,
SEQ ID No. 24
5'CAA ATG AGC TAC AAC ACACAA GG-3';

Hs.104417F,
SEQ ID No. 25
5'CCC CCT CCA CCTTGTACA TAA T-3';

Hs.104417R,
SEQ ID No. 26
5'GTT TTC GTT TGG CTGGTT GTG-3';

cl.21783F,
SEQ ID No. 27
5'GTC TGA GAT TTT ACTGCA CCG-3';

cl.21783R,
SEQ ID No. 28
5'GGA TGG AGC TGG AGGATA TTA-3';

Hs.112628F,
SEQ ID No. 29
5'ATT GCT AAG GAT AAGTGC TGC TC-3';

Hs.112628R,
SEQ ID No. 30
5'TGT CAG TAT AGA AGCCTG TGG GT-3';

Hs.170345F,
SEQ ID No. 31
5'TTC TTA GGC CAT CCCTTT TCT AC-3';

Hs.170345R,
SEQ ID No. 32
5'GCA TCT GAA TGT CTTTCT CCC TA-3';

Hs.53996F,
SEQ ID No. 33
5'CCA TAG GAT CTT GACTCC AAC AG-3';

Hs.53996R,
SEQ ID No. 34
5'ACT GGG AGT GGA GGAAAT TAG AG-3';

Hs.55422F,
SEQ ID No. 35
5'CTA ATG TAA GCT CCATTG GGA TG-3';

Hs.55422R,
SEQ ID No. 36
5'CAA ACT GCA AAC TAGCTC CCT AA-3';

Hs.112718F,
SEQ ID No. 37
5'AAG ACT AAG AGG GAA AAT GTG GG-3';

Hs.112718R,
SEQ ID No. 38
5'AGG TAA CCC AAA GTG ACA AAC CT-3';

Hs.115880F,
SEQ ID No. 39
5'TTA AGT GAG TCT CCT TGG CTG AG-3';

Hs.115880R,
SEQ ID No. 40
5'AGG GCC CCT ATA TCC AAT ACC TA-3';

Hs.126495F,
SEQ ID No. 41
5'GAT CTT TCA AGA TGAGCC AAG GT-3';

Hs.126495R,
SEQ ID No. 42
5'AGT CAT TCA GAA GCCATT GAG AC-3'

(Measurement of Signal Strength of RT-PCR Product and Calculation of Prognosis Score)

A PCR product was detected by 2% agarose gel electrophoresis and ethidium bromide staining. A gel was scanned by a digital image processing system (AlphaImager 3300; Alpha Innotech, San Leandro, Calif., USA) according to the Spot Density method. A two-dimensional region of each band was constructed, and pixel strength (gene expression) was obtained in which the density was defined as IDV (Integrated Density Value). Importance in a difference in IDV in each group was evaluated by the Student's t-test. As a result, 20 genes showing p values of 0.05 or lower in the t-test were selected as a candidate (Table 2). That is, expression levels of the 20 genes were significantly higher in the 5y-D group than in the 5y-S group. Base on this information, the present inventors have tried to establish a scoring system for predicting the postoperative prognosis. In this procedure, each gene was determined depending on whether the expression level of each sample was higher than the average expression level of 20 samples or not. When the expression level of a sample was 2-fold or more than the average, +1 point was imparted additionally. Next, points of all of the 20 genes were summed up fir obtaining the total vote (prognosis score) for each sample. As a result, a case of a sample of 8 points or more was evaluated as an indication of bad prognosis. On the other hand, a case of a sample of 8 points or less was evaluated as an indication of preferable prognosis.

TABLE 2

(20 candidate genes of prognosis scoring system)

| Hs./Accesion No. | kind |
|---|---|
| Hs.108504 | FLJ20113: ubiquitin-specific protease otubain 1 |
| Hs.146550 | MYH9: myosin, heavy polypeptide 9, non-muscle |
| Hs.194691 | RAI3: retinoic acid induced 3 |
| Hs.1975 | TDRD3: tudor domain containing 3 |
| Hs.203952 | TRRAP: transformation/transcription domain-associated protein |

TABLE 2-continued (20 candidate genes of prognosis scoring system)

| Hs./Accesion No. | kind |
|---|---|
| Hs.278607 | GSA7: ubiquitin activating enzyme E1-like protein |
| Hs.429 | ATP5G3: ATP synthase, H+ transporting, mitochondrial F0 complex, subunit c (subunit 9) isoform3 |
| Hs.75305 | AIP: aryl hydrocarbon receptor interacting protein |
| Hs.81170 | PIM1: pim-1 oncogene |
| Hs.99987 | ERCC2: excision repair cross-complementing rodent repair deficiency, complementation group 2 |
| Y12781 | Transducin (beta)like 1 protein |
| Hs.104417 | KIAA1205 protein |
| cl.21783 | Hypothetical protein |
| Hs.112628 | Hypothetical protein: MGC43581 |
| Hs.170345 | Hypothetical protein FLJ13710 |
| Hs.53996 | weakly similar to zinc finger protein 135 |
| Hs.55422 | Hypothetical protein |
| Hs.112718 | EST |
| Hs.115880 | EST |
| Hs.126495 | EST |

(Result)

257 genes highly expressed significantly in estrogen receptor-negative breast cancer tissue were clarified, and 378 genes expressed low were clarified likewise. For identifying genes showing different expressions between the 5y-D group and the 5y-S group, the data of a microarray was analyzed by the Mann-Whitney test and the Random-permutation test. As a result, 71 genes in total (including 10 EST and 9 genes encoding virtual protein) in 5y-D tumor were classified in common into a group of higher expression. In contrast, 15 genes (including 3 EST) were classified in common into a group of lower expression (FIG. 1).

Genes highly expressed in the 5y-D group include the following genes correlated with proliferation and metastasis of cancer cells; matrix metalloproteinase 2 (MMP2), heat shock protein 27 HSPB1), Pim-1 oncogene (PIM1) and transformation/transcription domain-associated protein (TR-RAP).

Genes expressed low in the 5y-D group include genes of HLA-C (major histocompatibility complex, class I, C) and specific kinase. A lot of genes having correlations with DNA repair, transcription, signal transduction, cytoskeleton and adhesiveness showed different expressions between two groups.

Figures 1, 1A, 2:
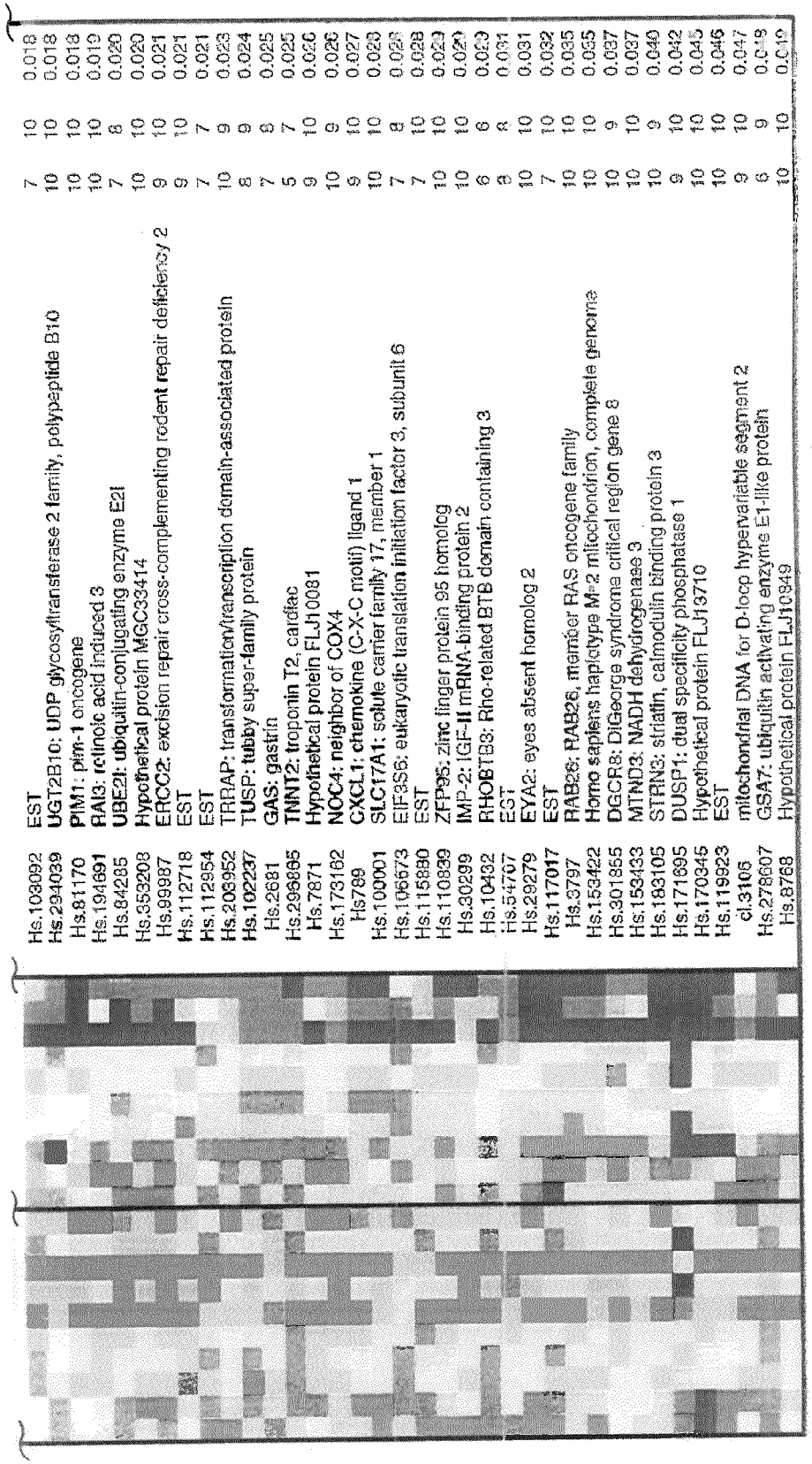
Figure 1B:
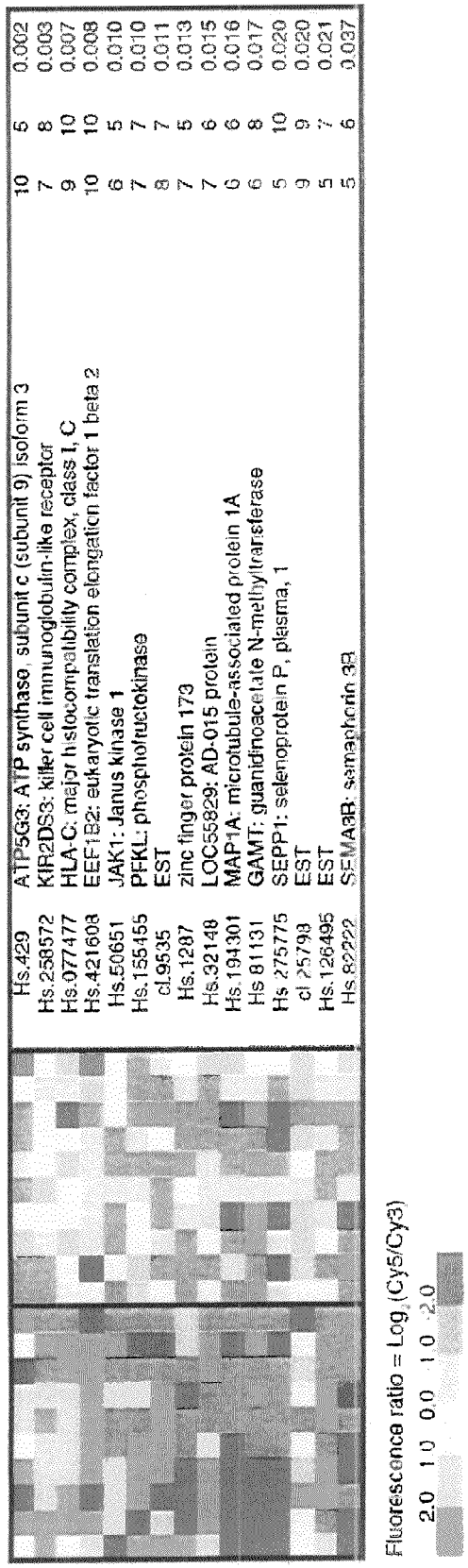
FIG. 1B is a photograph showing a gene group (B) manifesting decrease in expression in 5y-D group as compared with 5y-S group.
Figure 2:
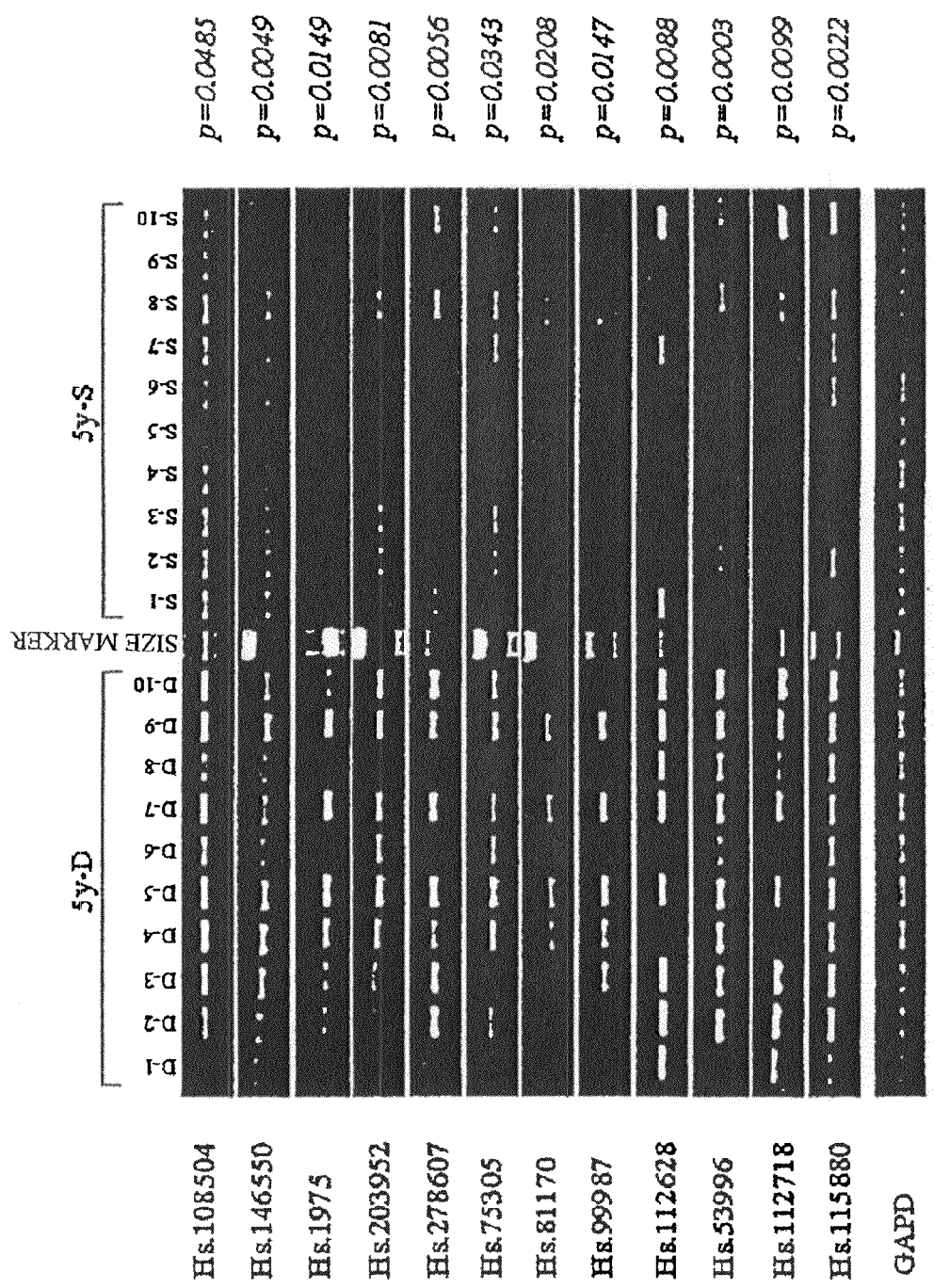

For confirming reliability of the data of a microarray, 20 genes highly expressed in the 5y-D group were selected (Hs.108504, Hs.146550, Hs.194691, Hs.1975, Hs.203952, Hs.278607, Hs.429, Hs.75305, Hs.81170, Hs.99987, Y12781, Hs.104417, cl.21783, Hs.112628, Hs.170345, Hs.53996, Hs.55422, Hs.112718, Hs.115880, and Hs.126495), and the expression levels of the genes were checked by semi-quantitative RT-PCR. The result coincided with the data of a microarray, and had a statistical significance for classifying the 5y-D group and the 5y-S group (typical data is shown in FIG. 2).

For constructing a scoring system for predicting the postoperative prognosis using the expression profile of a marker gene, prognosis score was calculated by the above-mentioned method. Briefly, a marker gene was selected according to the following standard.

(1) Higher signal strength than cut off level is shown in at least 60% of cases checked;

(2) $|\mu_D - \mu_S|$ is 1.0 or less. Here, $\mu_D(\mu_S)$ shows an average value derived from logarithm converted relative expression ratio in the case of 5y-D(5y-S).

Next, for identifying a marker gene capable of classifying the 5y-D group and the 5y-S group depending on the expression function, the Mann-Whitney test and the Random-permutation test were carried out. The result of a microarray correlated was confirmed by a semi-quantitative RT-PCR experiment. By the Student's t-test, 20 genes were selected as a prognosis marker (Table 2).

Depending on the prognosis score (PS) of the present invention, 20 patients were divided into 10 members predicted to show poor prognosis (PS is 11 or more) and 10 members predicted to show excellent prognosis (PS is less than 11). As a result, it was shown by comparison with the postoperative progress which the scoring system of the present invention has reliability with an accuracy of 80% in the 5y-D case and with an accuracy of 100% in the 5y-S case (FIG. 3A).

Figure 3:
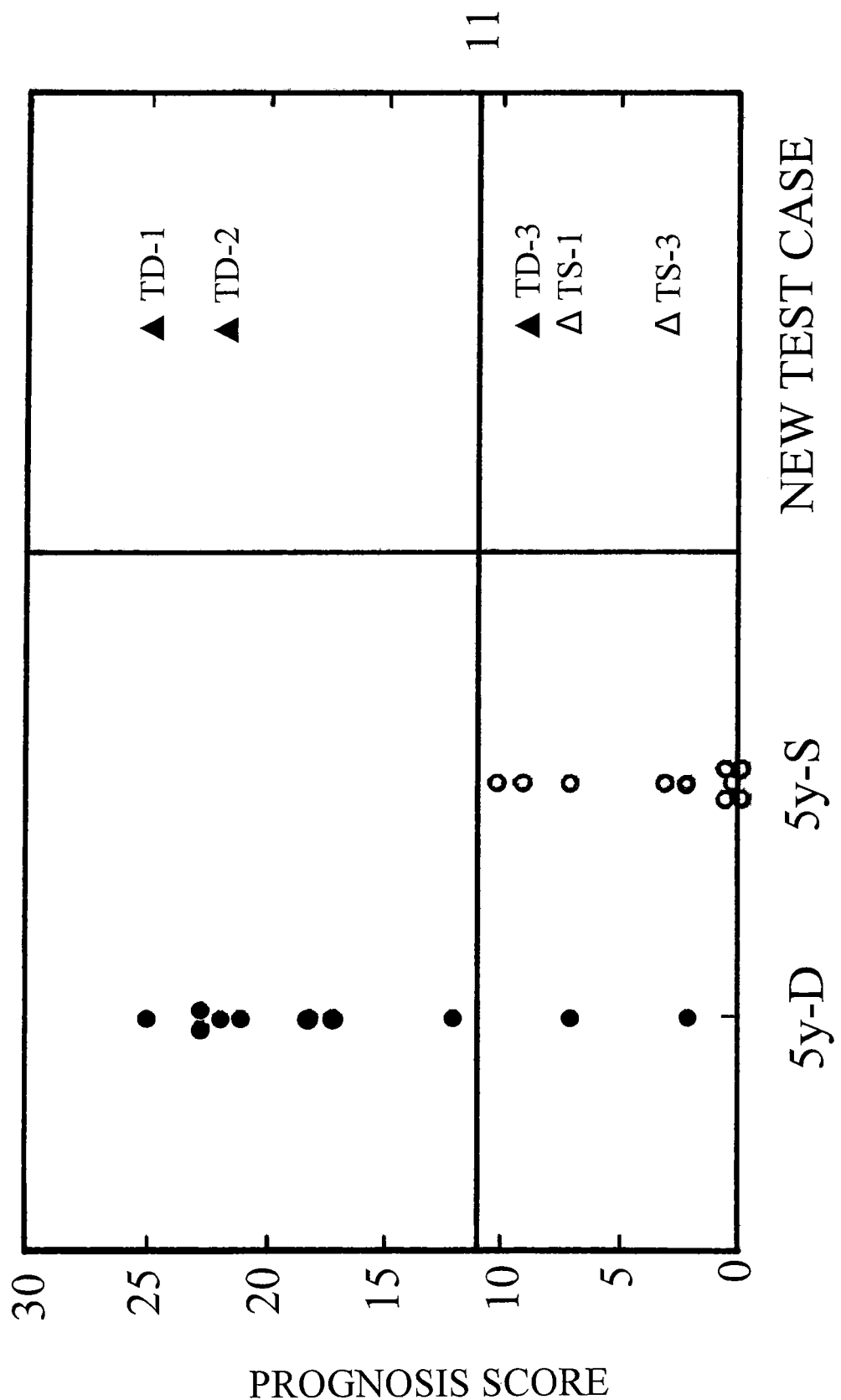
FIGS. 3 A and B show prognosis scores in individual patients.

Using the prognosis scoring system of the present invention, additional 5 cases were checked (FIG. 3B). The system predicted poor prognosis in 2 cases (PS>11; patient TD-1 and patient TD-2), and excellent prognosis in 3 cases (PS<11; patients TD-3, TS-1 and TS-2). As a result, this scoring system showed an accuracy of 80% regarding actual clinical results of these 5 cases.

Example 2

Evaluation of Gene Expression Function for Prediction of the Postoperative Prognosis in Node-Negative Breast Cancer (Tissue Sample)

A tissue sample was collected in the same manner as described in Example 1. Gene expression was investigated for tumors from 12 patients of node-negative (n0) cancer showed recurrence within 5 years after an operation (5 Y-R) and 12 patients survived free of disease for 5 years or more after the operation (5Y-F). The clinical backgrounds of both the patient groups were allowed to coincide in age, lymph node metastasis, tumor diameter, condition of hormone receptor, and pathological tissue (Table 3). The follow up intermediate period was 7.8 years, and the average period between the initial operation and recurring was 2.7 years in the 5Y-R group. All patients underwent the adjuvant therapy described in Example 1.

TABLE 3

(Clinical pathological data)

| Case | Age | Climacteric condition | Histological classification[a] | Position | Diameter (mm) | TNM classification[b] T | N | M | Stage | ER(+/−) | $P_gR$(+/−) | D.F.I.[c] |
|---|---|---|---|---|---|---|---|---|---|---|---|---|
| R-1 | 55 | Post. | a2 | Rt. | 25 | 2 | 1a | 0 | II | + | − | 12m |
| R-2 | 50 | Pre. | a3 | Lt. | 25 | 2 | 1a | 0 | II | + | + | 16m |
| R-3 | 42 | Pre. | a2 | Rt. | 25 | 2 | 0 | 0 | II | + | + | 49m |
| R-4 | 39 | Pre. | a3 | Rt. | 35 | 2 | 0 | 0 | II | + | − | 20m |

TABLE 3-continued (Clinical pathological data)

| Case | Age | Climacteric condition | Histological classification[a] | Position | Diameter (mm) | TNM classification[b] T | N | M | Stage | ER(+/−) | $P_gR$(+/−) | D.F.I.[c] |
|---|---|---|---|---|---|---|---|---|---|---|---|---|
| R-5 | 38 | Pre. | a2 | Lt. | 30 | 2 | 0 | 0 | II | + | + | 52m |
| R-6 | 61 | Post. | a3 | Lt. | 34 | 2 | 0 | 0 | II | − | − | 14m |
| R-7 | 54 | Post. | b3 | Lt. | 30 | 2 | 0 | 0 | II | − | − | 24m |
| R-8 | 37 | Pre. | a2 | Rt. | 23 | 2 | 0 | 0 | II | − | − | 25m |
| R-9 | 54 | Post. | a3 | Lt. | 25 | 2 | 1a | 0 | II | + | + | 47m |
| R-10 | 83 | Post. | a2 | Rt. | 28 | 2 | 1a | 0 | II | + | + | 38m |
| R-11 | 62 | Post. | a2 | Lt. | 23 | 2 | 0 | 0 | II | − | + | 40m |
| R-12 | 50 | Post. | a3 | Lt. | 35 | 2 | 0 | 0 | II | − | − | 25m |
| F-1 | 48 | Pre. | a2 | Lt. | 18 | 2 | 0 | 0 | II | + | + | 8Y |
| F-2 | 62 | Post. | a2 | Rt. | 25 | 2 | 0 | 0 | II | + | − | 8Y |
| F-3 | 57 | Post. | a1 | Rt. | 20 | 1 | 0 | 0 | I | + | + | 7Y10m |
| F-4 | 61 | Post. | a2 | Lt. | 30 | 2 | 1a | 0 | II | − | − | 7Y2m |
| F-5 | 42 | Pre. | a1 | Lt. | 12 | 1 | 1a | 0 | I | − | + | 7Y11m |
| F-6 | 51 | Pre. | a2 | Rt. | 28 | 2 | 1a | 0 | II | − | − | 7Y10m |
| F-7 | 59 | Post. | a2 | Rt. | 40 | 3 | 0 | 0 | II | − | − | 7Y5m |
| F-8 | 57 | Post.* | a2 | Rt. | 45 | 3 | 1b | 0 | II | − | − | 7Y5m |
| F-9 | 42 | Pre. | a1 | Lt. | 48 | 2 | 1a | 0 | II | − | + | 7Y3m |
| F-10 | 58 | Post. | a2 | Lt | 13 | 2 | 0 | 0 | II | − | − | 7Y3m |
| F-11 | 50 | Post. | a2 | Lt. | 25 | 2 | 0 | 0 | II | + | + | 7Y8m |
| F-12 | 55 | Post. | a1 | Rt. | 35 | 2 | 0 | 0 | II | + | + | 7Y5m |

[a]a1: invasive papillotubular carcinoma, a2: invasivesolid-tubularcarcinoma, a3: invasive schirrhous carcinoma
[b]TNM classification: clinically classified according to TNM classification by Japan Breast Cancer Society
[c]D.F.I.: period of no pathogeny (disease free interval)

(Clinicopathological Parameter)

The clinicopathological parameter was checked by the method described in Example 1. The histological grade was evaluated by a method of Elaston and Ellis (Abrams J S. Breast Cancer 2001; 8: 298-304). Lymphoduct invasion was evaluated to be deficient or positive (for example, evaluated to be positive when one or more cancer cells are present in lymphoducts around cancer). Fatinvasion was evaluated to be deficient or positive (for example, evaluated to be positive in the case of invasion into interstitial tissue).

(Preparation of cDNA Microarray)

"Genome wide cDNA microarray kit (Amersham Biosciences UK Limited, Buckinghamshire, UK)" with 25344 cDNAs was used. The PCR product was stopped on type 7 glass slides (Amersham Biosciences) using Array Spotter Generation III (Amersham Biosciences).

(Preparation and Proliferation of RNA)

Preparation and proliferation of RNA were carried out in the same method as described in Example 1.

(Labeling of aRNA, Hybridization and Scanning)

Labeling of aRNA, hybridization and scanning were carried out in the same method as described in Example 1.

(Mann-Whitney Test)

For identifying genes showing different expressions between a group of no disease and group of recurrence, normalized signals were analyzed by the Mann-Whitney test applied to a series of Xs. Here, X represents Cy5/Cy3 signal strength ratio of each gene and each sample. Genes showing a difference of 2-fold or more in expression strength between two groups were selected. Genes with signal-noise ratios of 3.0 or less were excluded from analysis.

The U value was calculated for genes imparting significant signals in at least 5 samples in both groups. Genes with U values of lower than 37 or larger than 107 were selected. Since the U value was obtained by calculation for 5Y-F group based on 5Y-R group in each gene based on each X value, genes with U values lower than 37 were evaluated to manifest higher expression in 5Y-F group than in 5Y-R group (first category). On the other hand, genes with U values higher than 107 were evaluated to manifest higher expression in 5Y-R group than in 5Y-F group (second category).

Based on this method, 78 genes were identified it the first category and 55 genes were identified in the second category. Thus, only genes showing a difference of 2-fold or more of the intermediate expression value between two grows ($\mu X_R/\mu X_F \leq 0.5$ or $\leq 2.0$, $\mu X_R$ and $\mu X_F$ represent average X values in 5Y-R and 5Y-F group, respectively) were defined as genes correlated with prognosis. In total, 98 genes were selected, and of them, 64 genes showed higher expression level in 5Y-F tumor and 34 genes showed higher expression level in 5Y-R tumor.

(Random-Permutation Test)

For evaluating values of genes selected by the Mann-Whitney test, a permutation test was carried out, and correlation to group difference (Ps) of genes selected was evaluated. When each gene is represented by an expression vector $v(g)=(X1, X2, ---, X24)$ (Xi shows a gene expression level of i-th sample in the first sample set), an idealized expression pattern is expressed by $c=(c1, c2, ---, c24)$ (ci=+1 or 0, depending on whether i-th sample belongs to F group or R group).

Correlation between a gene and a group difference Pgc was defined as described below. That is, $Pgc=(\mu F+\mu R)/(sF+sR)$; $\mu F(\mu R)$ and $sF(sR)$ show standard deviation of $\log_2 X$ of the gene "g" of each sample in a newly defined "F" group or "R" group.

The permutation test was carried out while substituting the coordinate of c. The correlation values, Pgcs were calculated between all permutations. These procedures were repeated for 10000 times. Accidentally, the p value showing a possibility of a gene for classifying two groups was evaluated for each of 58 genes selected.

(Semi-Quantitative RT-PCR)

RNA (5 µg) was treated with DNase I (Epicentre Technologies, Madison, Wis., USA), then, single-stranded cDNAs were subjected to reverse transcription using Reverscript II reversetranscriptase (manufactured by Wako Pure Chemical Industries, Ltd., Osaka, Japan) and 0.5 µg/µl oligo (dT) 12-18 primer. The preparations of single-stranded cDNAs were diluted for the subsequent PCR amplification by monitoring GAPDH as a quantitative control. All PCRs were carried out under the following reaction conditions using Gene Amp PCR system 9700 (Applied Biosystems, Foster City, Calif., USA) at an amount of 1×PCR buffer of 30 μl.

94° C. 2 minutes,
(94° C. 30 seconds, 58-62° C. 30 seconds, and 72° C. 30 seconds) for 27 to 35 cycles
72° C. 5 minutes.

Primer sequences for RT-PCR of GAPDH are as described below:

SEQ ID No. 43
(forward) 5'-GAA AGG TGA AGG TCG GAG T-3'

SEQ ID No. 44
(reverse) 5'-TGG GTG AAT CAT ATT GGA A-3'

TABLE 4A (Primer of semi-quantitative PCR (gene highly expressed in group of no disease))

| Ac./HS | SEQ ID No. | Forward | SEQ ID No. | Reverse |
|---|---|---|---|---|
| M90439 | 45 | CCAGACATCCATGGTACCTATAA | 46 | TATGCATTGAAACCTTACAGGGG |
| AF047472 | 47 | CTGTTAAACAAAGCGAGGTTAAGG | 48 | GGGTTCTGCATCTCGTTTATTAG |
| Hs.118251 | 49 | GACACATAGCTCATAGGCACACA | 50 | TTCTGGTACATGGTAAGTGCTCA |
| D26125 | 51 | TCCGCCATATTGATTCTGCTTA | 52 | GTTTGCTTTCTGGACCATGGATA |
| Hs.8619 | 53 | GATAACAACTGGACCACATCCC | 54 | AACAGGCAGACGAGGTAGACAC |
| X16135 | 55 | GAGAAGGATGGGTCCACCAGT | 56 | GTACATGGGCAGCACAAATGTAT |
| Hs.9006 | 57 | ATTTCATTGGTAGTATGGCCCAC | 58 | ATACCATGGGACAGGATTGTAAG |
| M18963 | 59 | GCTCAGACCAGCTCATACTTCAT | 60 | CCAAAGACTGGGGTAGGTAAAAC |
| X07979 | 61 | CTGGTGCTTTCTATCACCTCTTC | 62 | GACTAGTGTGAAACAAGATGGGC |
| AF018080 | 63 | CTTGAACCCAGGAGTTTGAGAC | 64 | GTGCCTCAGCTTTCTGAGTAGC |
| Hs.58464 | 65 | CTGGTGCTGACTATCCAGTTGA | 66 | CTGGTAAACTGTCCAAAACAAGG |
| S79867 | 67 | CTCTTACCTGGACAAGGTGCGT | 68 | GGATGAGCTCTGCTCCTTGAG |
| J02854 | 69 | CAATGTTTGACCAGTCCGAGA | 70 | CATGTTGTCTCAGTCCTCTATTGG |
| L35309 | 71 | GGACAGCAGCTGGAGTACACA | 72 | AATCAGATTTGTCGGTGCCTT |
| Hs.83097 | 73 | GGCTCTGCACTAAGAACACAGAG | 74 | ACAACTAGCTCTCAGTTCAGGCA |
| Hs.79137 | 75 | TGGAGCAGTATGACAAGCTACAA | 76 | AAGCAGCACTGCATAAACTGTTC |
| Hs.4864 | 77 | TAAGTACTTTCCTGTGGGTCGCT | 78 | CCACAAACAGGAAGCTATGTTCT |
| Y00052 | 79 | GTACTATTAGCCATGGTCAACCC | 80 | CTACAGAAGGAATGATCTGGTGG |
| Hs.5002 | 81 | ATCAGTACGGGGACCTTACAAAC | 82 | CCTGTACTGAGCTCTCCAAAGAC |
| U43519 | 83 | TCCCTAGCTTCCTCTCCACA | 84 | AGAATCATGCCTCCCCTTCT |
| Hs94653 | 85 | ACCCCTCAAGTGTAAGGAACTG | 86 | GGATCAAGAGTGTGTGTGTGTGT |
| X51441 | 87 | CAATGCCAGAGAGAATATCGAGA | 88 | GATACCCATTGTGTACCCTCTCC |
| Hs.108623 | 89 | CCACTCCACATAAGGGGTTTAG | 90 | GAGGTTCTAGCTAAGTGCAGGGT |
| Hs.5318 | 91 | CCATTGACATTGGAGTTAAGTATGC | 92 | GGCAAAGACCACATTTAGCAAT |
| Hs.69469 | 93 | GAAAGCCTATGTGAAAAGCTGGT | 94 | TTGTTTCCAGGCATTAAGTGTG |
| AA777648 | 95 | GCATCTTAGTCCACACAGTTGGT | 96 | GCCCTTACAGGTGGAGTATCTTC |
| Hs.106131 | 97 | CTCATAGCCAGCATGACTTCTTT | 98 | GGTTCACTTGTGACTGGTCATCT |
| X54079 | 99 | ACTTTTCTGAGCAGACGTCCAG | 100 | TATCAAAAGAACACACAGGTGGC |
| AI041182 | 101 | ACGTTATTCCCAGTTCCTAAACC | 102 | AGTCTCGGGTGACTCAATATGAA |
| AA148265 | 103 | AGTTGAACCCAGGTACCTTTCTC | 104 | CTAGGCCCTTTTAGAAAACATGG |
| Hs.4943 | 105 | TACTGGGAACGACTAAGGACTCA | 106 | TGCTGTGTTGAGTAGGTTTCTGA |
| Hs.106326 | 107 | TGAGAGTCCTCAGAGGGTATCAG | 108 | CTTGAAGTCAAGAGTCCTGGTGT |

TABLE 4A-continued (Primer of semi-quantitative PCR (gene highly expressed in group of no disease))

| Ac./HS | SEQ ID No. | Forward | SEQ ID No. | Reverse |
|---|---|---|---|---|
| M13436 | 109 | TTTCTGTTGGCAAGTTGCTG | 110 | CCCTTTAAGCCCACTTCCTC |
| X99920 | 111 | GATGAGAAGATGAAGAGCTTGGA | 112 | GAGGAAGCTTTATTTGGGAAGAG |
| U22970 | 113 | ACTTCCCTCTCTGCCTTTCTG | 114 | CAGATTGTTTTGGGCTTCTCACT |

TABLE 4B (Primer of semi-quantitative PCR (gene highly expressed in group of recurrence))

| Ac./HS | SEQ ID No. | Forward | SEQ ID No. | Reverse |
|---|---|---|---|---|
| X75252 | 115 | GTCTGGTCAGCTTTGCTTCC | 116 | GGCAAGTTCTGCACAGATGA |
| AA989127 | 117 | CAGCTCAGTGCACCATGAAT | 118 | GTGGGACTGAGATGCAGGAT |
| Hs.128520 | 119 | CACGGACTCATGAATGTAGTGAA | 120 | GTGTAGTGGCACGATCATAGCTT |
| HSMLN50 | 121 | GGGACCAAACAGACCAAAGA | 122 | CACCCCACAGAGCCTGTATT |
| AF058701 | 123 | CGGAAAGGCACTATTTCACAAT | 124 | ACAGGCCCACAGGTTTGTAAC |
| AF043473 | 125 | AAGCTCTTCAGCTGCGTCTC | 126 | CCTCCTCCTTTTCAGCTGTG |
| Hs.26052 | 127 | TCTGGAACCCTAAAAGTGTCGT | 128 | TCTTTCAACATCTCTCCACCCTA |
| Hs.77961 | 129 | AGATACCTGGAGAACGGGAAG | 130 | GGAAGTAAGAAGTTGCAGCTCAG |
| Hs.26484 | 131 | ATTAGGTTTCACCCAAAG | 132 | AGACGAGACTTGTTTTCTC |
| U44798 | 133 | CAGGGACTTGGTCACAGGTT | 134 | TTCTTCTCCCTCCCCTTGAT |
| Hs.77961 | 135 | GATTACATCGCCCTGAACGAG | 136 | TCCATCAACCTCTCATAGCAAA |
| X64707 | 137 | GTAAGATCCGCAGACGTAAGG | 138 | CTGAAGTCAGCCTCTGTAACCTC |
| Hs.6780 | 139 | ACTGACCCCACTTCTTGTGG | 140 | ACCCTTCCCTGTTGCTGTC |
| Hs.153428 | 141 | TCAAAGTATTTAGCTGACTCGCC | 142 | TAGTCACTCCAGGTTTATGGAGG |
| AI066764 | 143 | GGGAACTTGAATTCGTATCCATC | 144 | CTGAATCTCAAACCTGGAGAGTG |
| cl.5994 | 145 | GATCATCTTTCCTGTTCCAGAG | 146 | CTGGAAGGTTCTCAGGTCTTTA |
| D67025 | 147 | GTACGACCAGGCTGAGAAGC | 148 | ATCTTCGGGGCTATCCAACT |
| x16064 | 149 | TCAGCCACGATGAGATGTTC | 150 | TGTGGATGACAAGCAGAAGC |
| M80469 | 151 | ACCTTAGGAGGGCAGTTGGT | 152 | AGGGGTCACACCTTGAACAG |
| E02628 | 153 | GCATCCTACCACCAACTCGT | 154 | GCAGCATCACCAGACTTCAA |
| HUMTHYB4 | 155 | ACAAACCCGATATGGCTGAG | 156 | GCCAATGCTTGTGGAATGTA |
| Hs.116922 | 157 | TCGGACCATAATCCAAGTTACC | | |
| x15940 | 158 | TAACCCGAGAATACACCATCAAC | 159 | ATGGTTTTATTGACGGCAGAAG |

(Measurement of Signal Strength of RT-PCR Product and Calculation of Prognosis Score)

The signal strength of the RT-PCR product was measured and evaluated in the same method as described in Example 1, and 10 genes with p values of 0.05 or lower in the t-test were selected as a candidate of them, expression levels of 3 genes were higher in the 5y-R group than in the 5y-F group. The expression levels of 7 genes were higher in the 5y-F group than in the 5y-R group. Base on this information, the present inventors have tried to establish a scoring system for predicting the postoperative prognosis of node-negative breast cancer.

For obtaining expression level to be a subject of each gene, the expression ratio (ER) to the GAPDH expression was calculated according to the following formula:

ER of gene A=16 bit imaging score of semi-quantitative PCR (strength of band stained with ethidium bromide) of gene A of cancer sample X/16 bit imaging score of GAPDH of gene A of cancer sample X (Definition of Scoring System for Predicting Postoperative Prognosis of Node-Negative Breast Cancer)

For obtaining the postoperative gene prognosis index of node-negative breast cancer, prognosis score (PS) was defined; (sum of normalized expression ratios of genes highly expressed in 5Y-R group as compared in 5Y-F group)−(sum of normalized expression ratios of genes highly expressed in 5Y-F group as compared in 5Y-R group)

A significance of the expression ratio between two groups was evaluated by the Student's t-test. All statistical methods were carried out by Statview version 5.0 (SAS Institute, Cary, N.C.).

(Result)

Clinicopathological findings of 24 breast cancer patients whose genome-wide gene expressions have been investigated are summarized in Table 3. The present inventors have investigated the gene expression by a cDNA microarray composed of 25344 human genes, for tumors from node-negative breast cancer patients of 12 cases showing survival free of disease for 5 years or more after an operation (5Y-F) and node-negative breast cancer patients of 12 cases showing recurrence of breast cancer within 5 years after a surgical operation (5Y-R). The clinical backgrounds were allowed to coincide in age, tumor diameter, estrogen receptor and progesterone receptor, and pathology between two groups.

The data of a cDNA microarray was analyzed by the Mann-Whitney test and the Random-permutation test, and genes showing different expressions between 5Y-R tumor and 5Y-F tumor were identified. Through this filter, 58 genes in total were selected, and of them, 21 genes showed significant strong expression is 5Y-R tumor. 37 genes showed higher expression in 5Y-F tumor.

The 37 genes showed higher expression in 5Y-F tumor as compared in 5Y-R tumor had six ESTs and one virtual protein (Table 5A, a difference in expression between groups is expresses as "foldchange").

TABLE 5A (Gene with significant high expression in 5Y-F tumor as compared in 5Y-R tumor)

| Ac./HS | kind | fold change | p value |
|---|---|---|---|
| M90439 | molecular marker (EPC-1) gene | 2.324 | 0.0014 |
| AF047472 | spleen mitotic checkpoint BUB3 (BUB3) | 2.889 | 0.0021 |
| Hs.118251 | ESTs | 2.121 | 0.0031 |
| D26125 | 3 alpha-hydroxysteroid/dihydrodiol dehydrogenase DD4, partial cds | 2.084 | 0.0038 |
| Hs.8619 | SRY(sex determining region Y)-box 18 | 3.375 | 0.0041 |
| X16135 | novel heterogeneous nuclear RNP protein, L protein | 4.839 | 0.0042 |
| Hs.9006 | VAMP(vesicle-associated membrane protein)-associated protein A, 33 kDa | 3.807 | 0.0058 |
| M18963 | islet of Langerhans regenerating protein (reg) | 2.022 | 0.0060 |
| X07979 | integrin beta 1 subunit | 2.997 | 0.0068 |
| AF018080 | PYRIN (MEFV) | 4.016 | 0.0071 |
| Hs.58464 | ESTs | 5.415 | 0.0079 |
| S79867 | type I keratin 16 [human, epidermal keratinocytes, mRNA Partial, 1422 nt] | 2.254 | 0.0090 |
| J02854 | myosin light chain (MLC-2) | 2.668 | 0.0090 |
| Z35309 | adenylate cyclase8(brain) | 2.264 | 0.0094 |
| Hs.83097 | hypothetical protein FLJ22955 | 4.979 | 0.0096 |
| Hs.79137 | protein-L isosparate(D-aspartate)o-metyltransferase | 2.401 | 0.0105 |
| Hs.4864 | ESTs | 2.043 | 0.0107 |
| Y00052 | Peptidylprolyl isomerase A(cyclophilin A) | 2.966 | 0.0107 |
| Hs.5002 | copper chaperone for superoxide dismutase; CCS | 2.032 | 0.0114 |
| U43519 | dystrophin-related protein 2 (DRP2) | 2.022 | 0.0114 |
| Hs.106326 | ESTs | 4.733 | 0.0123 |
| Hs.94653 | neurochondrin(KIAA0607) | 2.08 | 0.0129 |
| M13436 | ovarian beta-A-inhibin | 2.946 | 0.0135 |
| X51441 | serum amyloid A (SAA) protein partial, clone pAS3-alpha | 2.383 | 0.0155 |
| Hs.108623 | thrombospondin 2 | 2.019 | 0.0174 |
| Hs.5318 | ESTs | 4.38 | 0.0174 |
| Hs.69469 | GA17 protein | 2.279 | 0.0197 |
| AA777648 | peripheral myelin protein 22 | 2.386 | 0.0209 |
| Hs.106131 | ESTs | 2.022 | 0.0213 |
| X54079 | heat shock protein HSP27 | 5.637 | 0.0217 |
| D67025 | proteasome (prosome, macropain) 26S subunit, non-ATPase, 3 | 3.179 | 0.0359 |
| M80469 | MHC class I HLA-J gene | 3.572 | 0.0380 |
| AI041182 | ov77e07.x1 Soares_testis_NHT Homo sapiens cDNA clone IMAGE: 1643364 | 2.321 | 0.0380 |
| AA148265 | RIBOSOMAL PROTEIN L21. | 2.019 | 0.0440 |
| Hs.4943 | Inter-Alpha-Trypsin Inhibitor Heavy Chain LIKE gene | 2.426 | 0.0442 |
| X99920 | S100 calcium-binding protein A13 | 3.326 | 0.0456 |
| U22970 | interferon-inducible peptide (6-16) gene | 2.741 | 0.0465 |

In Table 5B, 21 genes highly expressed in the 5Y-R group are listed. Of them, five genes are ESTs and one gene encodes a virtual protein. From the panel including 58 genes, marker for postoperative prognosis were selected according to the following standard; (1) Having signal strength than cut off level situated in at least 60% of cases; (2) |μR|μF|>1.0. Here, μR(μF) shows an average value derived from logarithm converted expression ratio in the case of 5Y-R or 5Y-F.

TABLE 5B (Gene with significant high expression in 5Y-R tumor as compared in 5Y-F tumor)

| Ac./HS | kind | fold change | p value |
|---|---|---|---|
| X75252 | Prostatic Bindig protein | 4.506 | 0.0011 |
| AA989127 | major histocompatibility complex, class I, C | 5.731 | 0.0060 |
| Hs.128520 | ESTs | 1.419 | 0.0067 |
| HSMLN50 | ESTs | 3.482 | 0.0071 |
| AF058701 | DNA polymerase zeta catalytic subunit (REV3) | 2.185 | 0.0085 |
| AF043473 | delayed-rectifier K+ channel alpha subunit (KCNS1), Potassium voltage-gated channel, delayed-rectifier, subfamily S, member 1 | 4.786 | 0.0144 |
| Hs.26052 | hypothetical protein MGC43306 | 4.829 | 0.0150 |
| Hs.77961 | major histocompatibility complex, class I, B | 5.775 | 0.0152 |
| Hs.26484 | HIRA interacting protein 3 | 5.07 | 0.0157 |
| U44798 | U1-snRNP binding protein homolog (70 kD) | 2.615 | 0.0194 |
| Hs.77961 | MHC class I HLA-Bw62 | 5.775 | 0.0209 |
| X64707 | BBC1 mRNA(ribosomal protein L13) | 2.758 | 0.0210 |
| Hs.6780 | PTK9L protein tyrosine kinase 9-like (A6-related protein) | 2.749 | 0.0220 |
| Hs.153428 | Ests | 3.164 | 0.0234 |
| AI066764 | lectin, galactoside-binding, soluble, 1 (galectin 1) | 2.606 | 0.0275 |
| cl.5994 | ESTs | 2.844 | 0.0286 |
| x16064 | Tumor protein, translationally-controlled 1 | 3.567 | 0.0366 |
| E02628 | polypeptide chain elongation factor-1 alpha | 4.055 | 0.0427 |
| HUMTHYB4 | thymosin beta-4 | 4.05 | 0.0436 |
| Hs.116922 | ESTs | 2.538 | 0.0494 |
| x15940 | ribosomal protein L31. | 2.125 | 0.0499 |

7 genes highly expressed in 5Y-F tumor as compared in 5Y-R tumor (Hs.94653, M13436, Hs.5002, D67025, M80469, Hs.4864 and Hs 106326; p=0.0018, 0.0011, 0.001, 0.008, 0.0081, 0.0018 and 0.001; each according to Student's t-test) and 3 genes relatively highly expressed in 5Y-R tumor (AF058701, AI066764, and x15940; p=0.0351, 0.00161 and 0.0001; each according to Student's t-test) coincided with standards, and were selected as a prognosis marker (Table 6).

TABLE 6

(Genes selected as prognosis marker for node-negative breast cancer)

| | |
|---|---|
| AF058701 | DNA polymerase zeta catalytic subunit (REV3) |
| AI066764 | lectin, galactoside-binding, soluble, 1 (galectin 1) |
| x15940 | ribosomal protein L31 |
| Hs.94653 | neurochondrin(KIAA0607) |
| M13436 | ovarian beta-A-inhibin |
| Hs.5002 | copper chaperone for superoxide dismutase; CCS |
| D67025 | proteasome (prosome, macropain) 26S subunit, non-ATPase, 3 |
| M80469 | MHC class I HLA-J gene |
| Hs.4864 | ESTs |
| Hs.106326 | ESTs |

Figure 4:
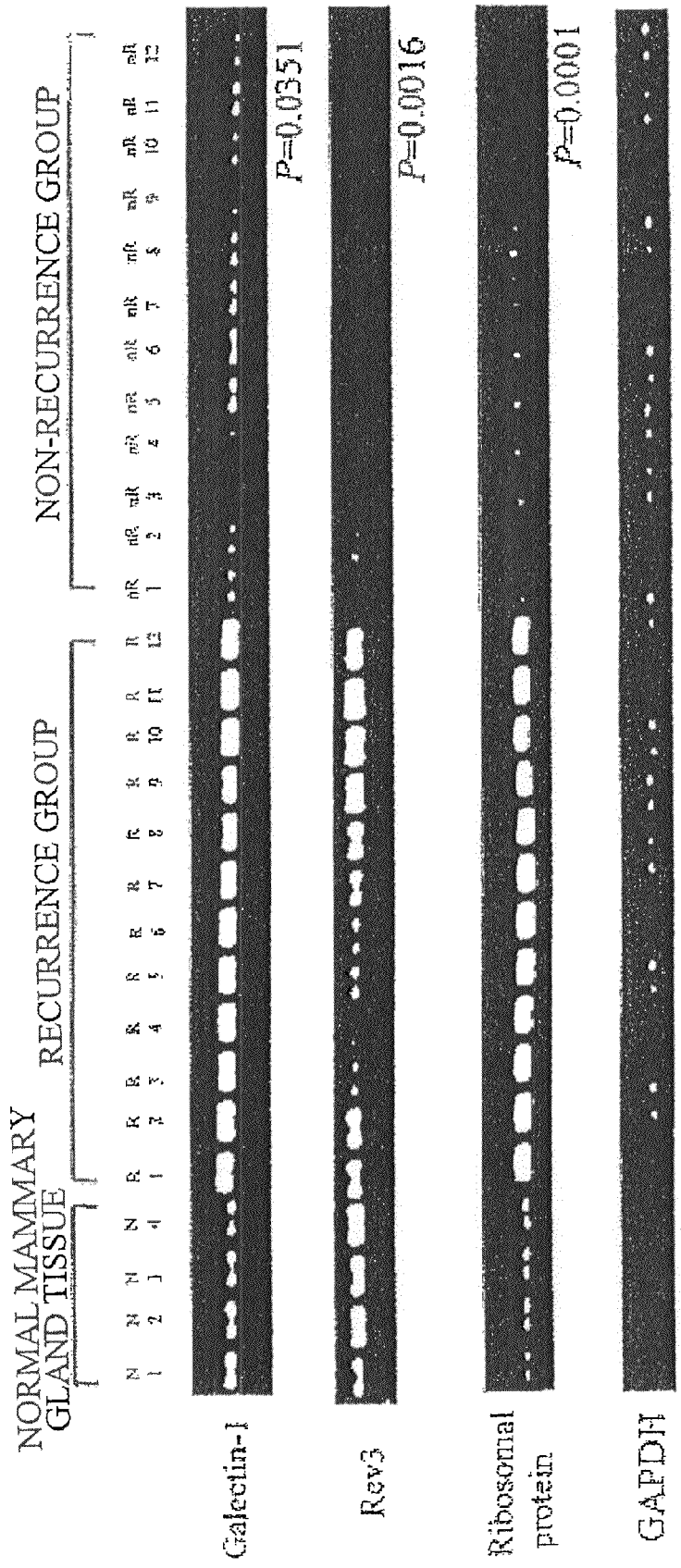
FIG. 4 is a photograph showing analysis results of semi-quantitative RT-PCR of RNAs derived from 5Y-F group and 5Y-R group.
Figure 5:
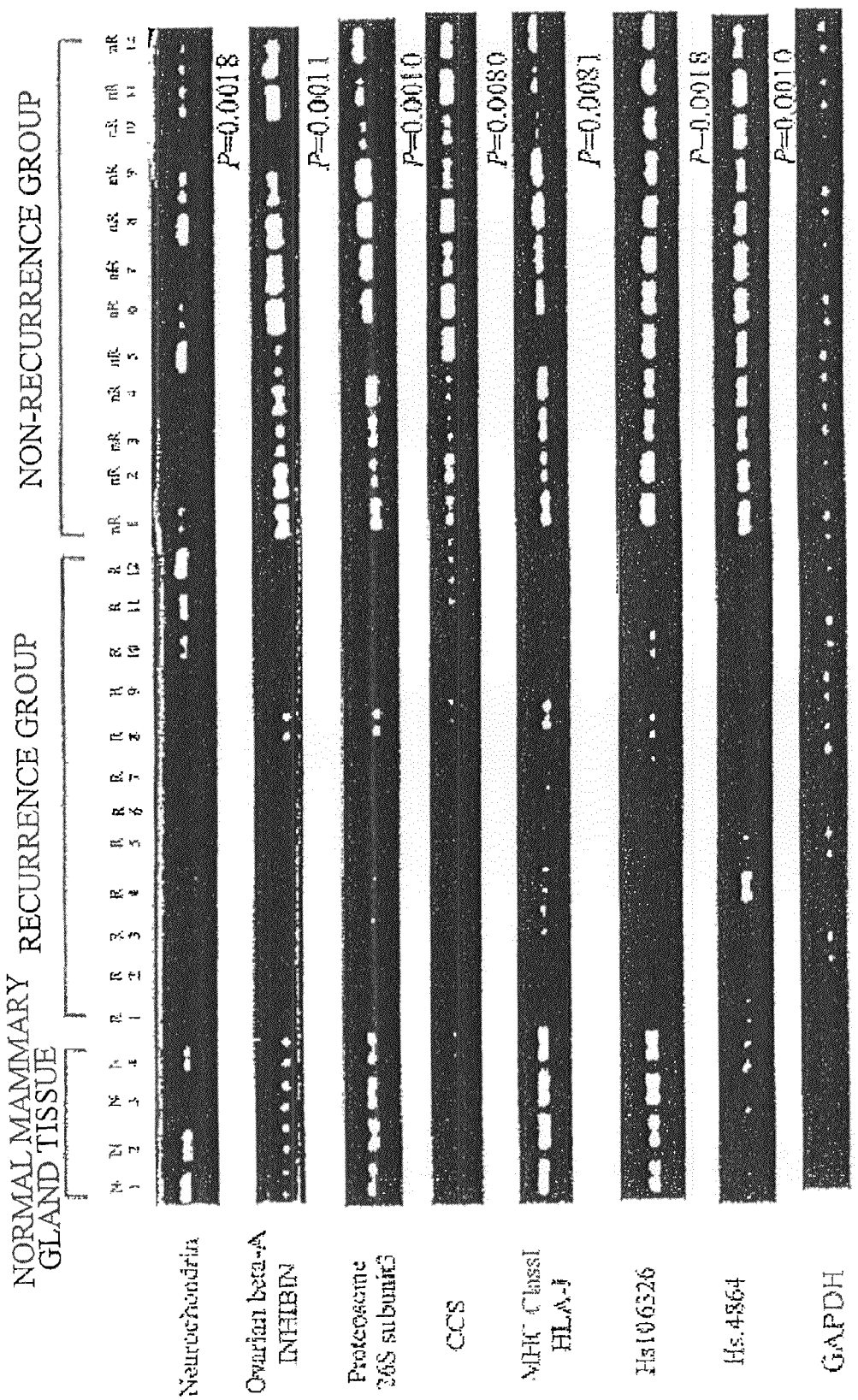
FIG. 5 is a photograph showing analysis results of semi-quantitative RT-PCR of RNAs derived from 5Y-F group and 5Y-R group.

Expressions of these markers were confirmed by a normalized semi-quantitative RT-PCR experiment for GAPDH expression. FIG. 4 shows results of RT-PCR of three marker genes highly expressed in samples from 12 patients showing recurrence of breast cancer (5Y-R group). FIG. 5 shows results of 7 marker genes highly expressed in the 5Y-F group (5 years survival). The expression ratios of these 10 genes were used for definition of prognosis index.

Prognosis score (PS) was defined as described below;

PS=(sum of normalized expression ratios of 3 genes highly expressed in 5Y-R tumor)−(sum of normalized expression ratios of 7 genes highly expressed in 5Y-F tumor)

Figure 6:
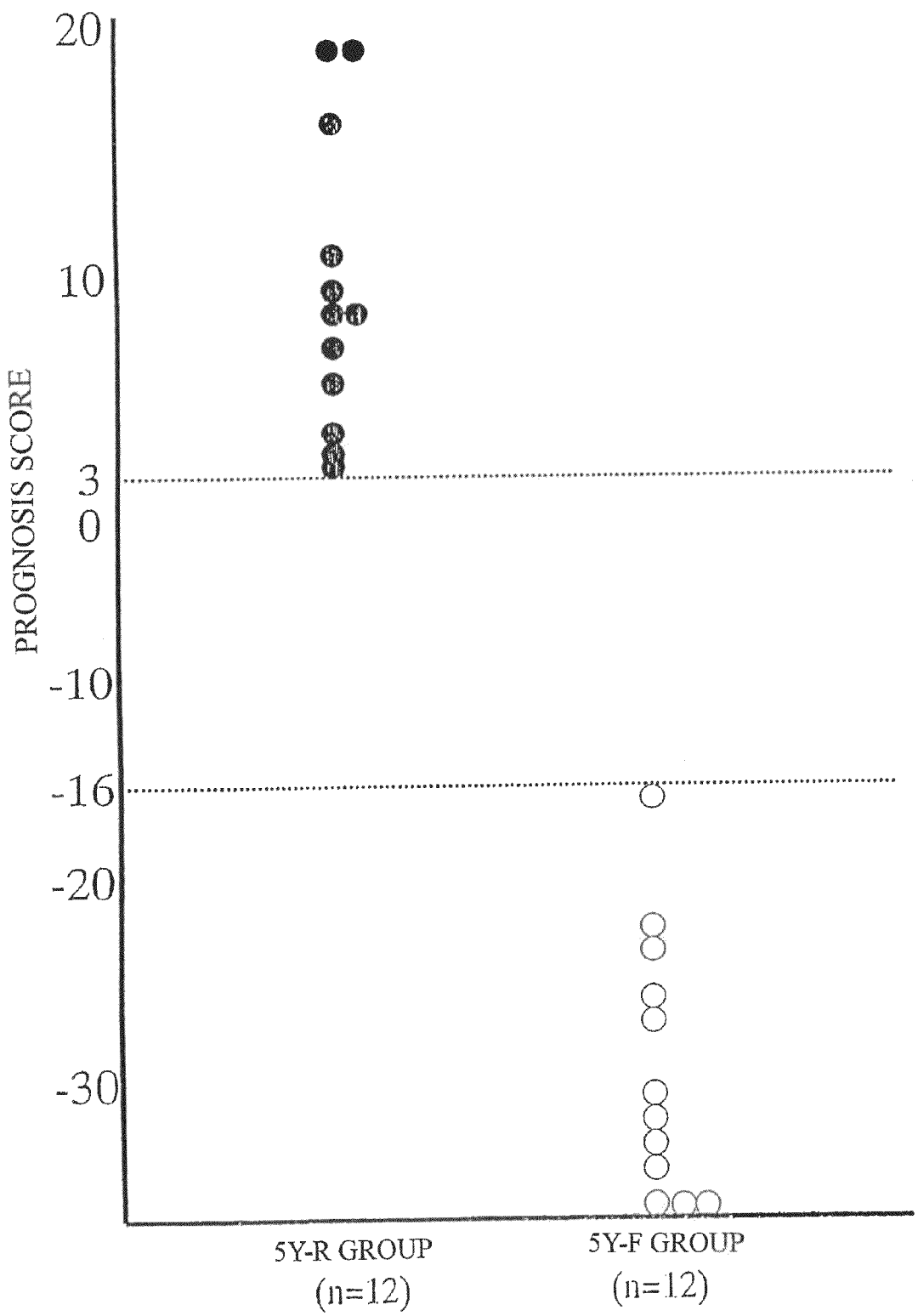
FIG. 6 shows prognosis scores in individual patients.

The prognosis scores of 24 cases investigated are summarized in Table 7 together with the expression ratio of each marker gene. The PS system predicted poor prognosis of cases R1 to R12 having prognosis scores of more than 3. On the other hand, excellent prognosis was predicted for cases F1 to F12 having scores of lower than −16. The predictions coincided with actual clinical results of them with an accuracy of 100% (FIG. 6). The average PS of the 5Y-R group was 9.44 and the average PS of the 5Y-F group was −28.92.

TABLE 7

(Prognosis score for recurrence of node-negative breast cancer)

| No. | x15940 | AF058701 | AI066764 | Hs.5002 | Hs.94653 | M13436 | M80469 | D67025 | Hs.4864 | Hs.106326 | PS |
|---|---|---|---|---|---|---|---|---|---|---|---|
| 1n | 8.90 | 2.70 | 8.35 | 1.50 | 0.82 | 1.47 | 2.43 | 2.72 | 2.60 | 2.55 | 5.86 |
| 2n | 7.02 | 2.19 | 7.48 | 1.14 | 0.50 | 1.51 | 2.32 | 1.27 | 1.89 | 0.62 | 7.44 |
| 3n | 7.57 | 2.36 | 10.96 | 1.40 | 0.55 | 2.29 | 3.51 | 2.38 | 1.79 | 0.44 | 8.53 |
| 4n | 8.57 | 2.79 | 9.78 | 1.75 | 1.42 | 2.02 | 3.30 | 3.03 | 3.44 | 3.02 | 3.16 |
| 5n | 14.96 | 2.56 | 18.01 | 3.88 | 0.53 | 0.67 | 3.96 | 2.76 | 3.78 | 1.83 | 18.12 |
| 6n | 16.94 | 3.97 | 12.76 | 0.11 | 0.73 | 1.50 | 3.19 | 2.01 | 3.60 | 4.41 | 18.12 |
| 7n | 14.51 | 3.02 | 11.62 | 0.37 | 2.24 | 2.05 | 2.14 | 1.45 | 1.64 | 2.96 | 16.30 |
| 8n | 9.50 | 2.81 | 10.43 | 2.86 | 1.64 | 1.95 | 5.40 | 3.18 | 1.89 | 1.79 | 4.03 |
| 9n | 8.29 | 2.96 | 8.32 | 0.78 | 0.55 | 1.91 | 1.50 | 1.31 | 1.40 | 2.80 | 9.32 |
| 10n | 6.78 | 2.06 | 10.59 | 0.39 | 1.93 | 0.70 | 2.49 | 3.56 | 1.27 | 0.84 | 8.25 |
| 11n | 7.30 | 1.38 | 10.89 | 3.03 | 2.82 | 0.46 | 2.18 | 3.09 | 2.00 | 2.16 | 3.83 |
| 12n | 8.60 | 3.81 | 15.86 | 3.31 | 3.46 | 0.70 | 3.19 | 1.82 | 2.54 | 2.95 | 10.30 |
| 1nR | 4.67 | 0.81 | 4.69 | 4.13 | 2.98 | 3.80 | 7.78 | 5.34 | 7.59 | 8.47 | −29.92 |
| 2nR | 4.32 | 0.63 | 3.88 | 2.82 | 2.68 | 2.89 | 4.51 | 3.74 | 4.86 | 9.28 | −21.95 |
| 3nR | 10.54 | 0.56 | 7.28 | 2.40 | 2.06 | 2.10 | 8.18 | 6.02 | 6.02 | 8.55 | −16.95 |

TABLE 7-continued (Prognosis score for recurrence of node-negative breast cancer)

| No. | x15940 | AF058701 | AI066764 | Hs.5002 | Hs.94653 | M13436 | M80469 | D67025 | Hs.4864 | Hs.106326 | PS |
|---|---|---|---|---|---|---|---|---|---|---|---|
| 4nR | 5.59 | 0.56 | 4.85 | 3.22 | 3.69 | 2.89 | 11.18 | 3.31 | 6.39 | 11.36 | −31.04 |
| 5nR | 5.56 | 0.18 | 4.97 | 5.57 | 4.57 | 1.15 | 3.18 | 4.85 | 5.56 | 12.68 | −26.85 |
| 6nR | 4.50 | 0.51 | 4.01 | 6.81 | 2.54 | 5.45 | 6.61 | 7.49 | 7.16 | 6.18 | −33.22 |
| 7nR | 5.09 | 0.97 | 4.72 | 3.14 | 3.74 | 5.57 | 7.95 | 3.94 | 7.90 | 9.71 | −31.17 |
| 8nR | 4.93 | 0.54 | 4.46 | 7.53 | 4.95 | 5.93 | 11.03 | 1.96 | 6.21 | 7.75 | −35.43 |
| 9nR | 5.25 | 1.17 | 5.15 | 3.09 | 3.39 | 3.30 | 10.05 | 2.66 | 4.76 | 10.82 | −26.50 |
| 10nR | 5.36 | 0.59 | 5.96 | 3.67 | 2.78 | 2.47 | 4.66 | 3.12 | 10.63 | 8.27 | −23.69 |
| 11nR | 4.99 | 1.02 | 5.71 | 7.48 | 4.51 | 6.22 | 4.61 | 4.28 | 10.65 | 9.20 | −35.23 |
| 12nR | 4.84 | 0.30 | 4.98 | 7.57 | 6.07 | 5.04 | 7.05 | 3.07 | 7.42 | 8.98 | −35.08 |

Example 3

Evaluation of Gene Expression Function for Prediction of the Postoperative Prognosis in Primary Breast Cancer (Tissue Sample)

A tissue sample was collected in the same manner as described in Example 1. Among 954 patients clinically traced during a period of 5 years or more or until death after an operation for breast cancer in a period from 1995 to 1997, 10 cases of death within 5 years after an operation and 10 cases of survival free of disease for 5 years or more after an operation were selected as a sample. The clinical backgrounds between two patient groups were allowed to coincide as strictly as possible regarding age, metastasis to lymph node, tumor diameter and tissue type (Table 8). The clinical backgrounds of additional 20 cases used for testing the final prediction system are summarized in Table 9.

TABLE 8

(Clinical profile of patients used for microarray analysis)

| | Case | T | N | M | Stage | Age | NL$^a$ | ly$^b$ | f$^c$ | ER$^d$ |
|---|---|---|---|---|---|---|---|---|---|---|
| Survived | MS1 | 2 | 1 | 0 | II | 52 | 4 | 1 | 2 | P |
| | MS2 | 2 | 2 | 0 | II | 47 | 2 | 0 | 1 | P |
| | MS3 | 2 | 2 | 0 | II | 40 | 5 | 0 | 1 | N |
| | MS4 | 2 | 2 | 0 | II | 64 | 3 | 0 | 1 | N/A |
| Dead | MD1 | 2 | 2 | 0 | II | 47 | 5 | 0 | 0 | P |
| | MD2 | 2 | 2 | 0 | II | 34 | 3 | 3 | 0 | N |
| | MD3 | 2 | 2 | 0 | II | 66 | 4 | 0 | 3 | N |
| | MD4 | 2 | 0 | 0 | II | 71 | 2 | 0 | 1 | P |

$^a$Number of lymph nodes involved
$^b$Lymph vessel invasion: 0, no cancer cells in vessels. 3, many cancer cells in vessels.
$^c$Fat invasion: 0, no invasion to fat tissue; 3, severe invasion to fat tissue.
$^d$Estrogen receptor status: P, positive; N, negative; N/A, not available.

TABLE 9

(Clinical profile of patients used for RT-PCR analysis)

| | Case | T | N | M | Stage | ly$^a$ | f$^b$ |
|---|---|---|---|---|---|---|---|
| Survived | S1 | 2 | 0 | 0 | II | 0 | 1 |
| | S2 | 2 | 2 | 0 | II | 1 | 0 |
| | S3 | 2 | 2 | 0 | II | 0 | 2 |
| | S4 | 2 | 1 | 0 | II | 1 | 0 |
| | S5 | 2 | 2 | 0 | II | 3 | 2 |
| | S6 | 2 | 0 | 0 | II | 0 | 0 |
| | S7 | 2 | 1 | 0 | II | 0 | 0 |
| | S8 | 2 | 1 | 0 | II | 0 | 2 |
| | S9 | 2 | 1 | 0 | II | 1 | 2 |
| | S10 | 2 | 1 | 0 | II | 0 | 0 |
| Dead | D1 | 2 | 1 | 0 | II | 0 | 1 |
| | D2 | 2 | 2 | 0 | II | 0 | 0 |
| | D3 | 2 | 2 | 0 | II | 3 | 0 |
| | D4 | 2 | 2 | 0 | II | 0 | 3 |
| | D5 | 2 | 2 | 0 | II | 1 | 3 |
| | D6 | 2 | 1 | 0 | II | 0 | 1 |
| | D7 | 2 | 0 | 0 | II | 0 | 1 |
| | D8 | 2 | 1 | 0 | II | 0 | 0 |
| | D9 | 2 | 4 | 0 | IV | 1 | 0 |
| | D10 | 2 | 1 | 0 | II | 0 | 2 |

| | Age$^c$ | lymph node correlation$^d$ |
|---|---|---|
| Survived | 52.8 | 7.6 |
| Dead | 56.0 | 5.4 |

$^a$Lymph vessel invasion
$^b$Fat infiltration
$^c$Mean of age
$^d$Average number of lymph nodes involved (Clinicopathological Parameter)

The clinicopathological parameters were checked by the method described in Example 1.

(Preparation of cDNA Microarray)

A cDNA microarray was prepared by the method described in Example 2.

(RNA Extraction and RNA Amplification)

RNA was extracted using TRIzol (Invitrogen, Carlsbad, Calif., USA). For removing degenerate RNA, each extracted RNA (1 µg) was subjected to electrophoresis on 3.0% formaldehyde denatured gel. For removing DNA mixing, purification was carried out using RNeasy kit (QIAGEN, Valencia, Calif.). Amplification was carried out based on T7 RNA polymerase base by Message Amp aRNA kit (Ambion, Austin, Tex.), and RNA used for microarray analysis was prepared. In the first amplification, RNA (5 µg) was used as a template. Thereafter, the firstly amplified RNA (aRNA) (2 µg) was used as a template for the second amplification. The amplified aRNAs were purified by RNeasy purification kit, and the amount of each aRNA was measured by a spectrophotometer.

(Labeling of aRNA, Hybridization and Data Analysis)

A hybridization probe was produced using aRNA (5 µg) for producing fluorescent probe obtained by second amplification, using Amino Allyl-cDNA labeling kit (Ambion, Austin, Tex.). Probes derived from cancer RNA and normal control RNA were labeled with Cy5 or Cy3 Mono-Reactive Dye (Amersham Bioscience UK Limited, Buckinghamshire, UK), respectively.

For removing an unbound dye, a labeled probe was purified by QIA quick PCR purification kit (QIAGEN, Valencia, Calif.). Each 10 pmol of fluorescent labeled probes from tumor and normal RNA were mixed with 4× microarray hybridization buffer (Amersham (UK)) and de-ionized formamide. The probe mixture was hybridized to a cDNA array at 40° C. for 15 hours. Thereafter, the mixture was washed with 0.1×SSC containing 0.2% SDS once for 5 minutes, then, twice or 10 minutes. All procedures were carried out in Automated Slide Processor System (Amersham). The signal strength of each hybridization was read by Gene Pix 4000 (Amersham) and evaluated by Gene Pix Pro M (Axon Instruments, Inc., Foster City, Calif., USA). The read signals were normalized by the total gene normalization method (Yang, Y. H., Dudoit, S., Luu, P., Lin, D. M., Peng, V., Ngai, J., and Speed, T. P. (2002). Nucleic Acids Res 30, e15; Manos, E. J., and Jones, D. A. (2001). Cancer Res 61, 433-438).

For confirming genes showing different expressions between a survival group and a dead group, normalized signals were analyzed by the Mann-Whitney test; the normalized signals were applied to a series of Xs. X represents Cy5/Cy3 signal strength ratio for each gene and each sample (Ono, K., et al. (2000). Cancer Res 60, 5007-5011). Genes showing a U value of 0 in the Mann-Whitney test and genes showing a difference of 2-fold or more in expression strength between two groups were selected. Genes with S/N ratios of less than 3.0 were excluded from investigation.

(Semi-Quantitative RT-PCR Experiment and Gene Expression Ratio)

For verifying the data of a microarray, the present inventors carried out a semi-quantitative RT-PCR experiment by reverse-transcribing RNA (10 μg). For adjusting the concentration of the transcribed cDNA, GAPDH was selected as an internal control, and semi-quantitative RT-PCR was carried out (Ono, K., et al. (2000). Cancer Res 60, 5007-5011). Primers for GAPDH were 5'-ggaaggtgaaggtcggagt-3 (Forward) and 5-tgggtggaatcatattggaa-3 (Reverse). After adjusting the concentration of the primer, semi-quantitative RT-PCR was carried out on selected genes in samples from the survival group and the dead group. Primers for the genes (Table 10) were designed based on sequence information of NCBIGen Bank (http://www.ncbi.nlm.nih.gov/) and primer 3 on website (http://www.genome.wi.mit.edu/cgi-bin/primor/primer3_www.cgi). Each semi-quantitative RT-PCR experiment was performed using, as a template, cDNA (1 μl) having been adjusted concentration, 5 U TakaraEXTaq (Takara, Otsu, Japan), 1×PCR buffer (10 mM Tris-HCl, 50 mM KCl, 1.5 mM MgCl$_2$), and 10 nM dNTPs and 10 pmol of forward and reverse primers, in a total amount of 30 μl.

SEQ ID No. 160
ggaaggtgaaggtcggat

SEQ ID No. 161
tgggtggaatcatattggaa

TABLE 10

(Primer of semi-quantitative PCR)

| gene | SEQ ID No. | Forward | SEQ ID No. | Reverse |
|---|---|---|---|---|
| PMP | 162 | CCTCCAACTGCTCCTACTCG | 163 | TCGAAGCCTCTGTGTCCTTT |
| C1r | 164 | GAAGTTGTGGAGGGACGTGT | 165 | GACTTCCAGCAGCTTCCATC |
| DPYSL3 | 166 | CATGTACTGAGCAGGCCAGA | 167 | AAGATCTTGGCAGCGTTTGT |
| PTK9L | 168 | TTGTGATTGAGGACGAGCAG | 169 | AATGGTTTCCCGCTCTAGGT |
| CPE | 170 | CTCCTGAGACCAAGGCTGTC | 171 | TGAAGGTCTCGGACAAATCC |
| α-tubulin | 172 | GGAACGCCTGTCAGTTGATT | 173 | CTCAAAGCAAGCATTGGTGA |
| β-tubulin | 174 | TCTGTTCGCTCAGGTCCTTT | 175 | TGGTGTGGTCAGCTTCAGAG |
| HSP 90-a | 176 | AAAAATGGCCTGAGTTAAGTGT | 177 | TCCTCAATTTCCCTGTGTTTG |
| MDH | 178 | TGCACACTAACAGCATGACG | 179 | GAATTTCTTTCCTCTGCCTGA |
| NDUFB3 | 180 | GGGATAAACCAGACAAGTAGGC | 181 | GGACATGAGCATGGACATCA |

For evaluating the strengths of gene expressions between the survival group and the dead group, each semi-quantitative PCR product (8 μl) was subjected to electrophoresis on 2.5% agarose gel, and stained with ethidium bromide. The concentration of each stained sample was measured by AlphaImager 3300 (Alpha Ironotech, San Leandro, Calif.) using background correction. For obtaining the expression level of each gene, the expression ratio was normalized with the expression level of GAPDH.

The expression ratio was defined by the following formula: Expression ratio of gene A=16 bit imaging score of semi-quantitative PCR (strength of band stained with ethidium bromide) of gene A in cancer sample X/16 bit imaging score of GAPDH in cancer sample X (Definition of Prognosis Index (PI) of Primary Breast Cancer)

The present inventors defined the prognosis index (PI) of primary breast cancer by subtracting the sum of normalized expression ratios of genes highly expressed in the 5D group from the sum of normalized expression ratios of genes highly expressed in the 5S group. A significance of expression ratios between two groups was evaluated by the Student's t-test. Comparison of PI between the 5S group and the 5D group was carried out by the Mann-Whitney test. All the statistics were storaged using Statview version 5.0 (SASInstitute Inc., Cary, N.C.).

(Result)

On a cDNA microarray composed of 18432 human genes, genome-wide gene expression functions of tumors from 8 breast cancer patients were examined. Four patients survived free of disease for 5 year or more after an operation (5S), and four patients died of breast cancer within 5 years after the operation (5D). The clinical backgrounds between two patient groups were allowed to coincide as strictly as possible regarding age, tumor diameter, metastasis to lymph node, hormone receptor condition and tissue type (Table 8).

For identifying genes showing different expressions between the 5D group and the 5S group, the present inventors analyzed the data of the cDNA microarray by the Mann-Whitney test. 23 genes in total among which six genes are ESTs/virtual proteins are genes showing a U value of 0 in the Mann-Whitney test and highly expressed in the 5S group (Table 11).

From 23 genes highly expressed in the 5S group and 21 gene highly expressed in the 5D group, prediction markers for postoperative prognosis were selected according to the following standards; (1) In microarray analysis, a difference in the signal strength between 5S and 5D is larger than 2.0-fold in all cases; (2) The signal strength differs significantly between 5S and 5D in semi-quantitative PCR (p value<0.05

TABLE 11

(Gene group highly expressed in survival group by microarray analysis)

| Gene name and detail | Accession Number | Fold change |
| --- | --- | --- |
| IMAGE: 39159 3' similar to gb: J04173 PHOSPHOGLYCERATE MUTASE, BRAIN FORM | R51864 | 4.304 |
| IMAGE: 22798 3', MRNA sequence | R39171 | 2.918 |
| cDNA clone IMAGE: 1693352 3', MRNA sequence | AI140851 | 2.891 |
| CCNDBP1 cyclin D-type binding-protein 1 | AF082569 | 3.202 |
| ESTs | AI446435 | 3.251 |
| pro-alpha-1 type 3 collagen | X14420.1 | 3.394 |
| complement component C1r | J04080.1 | 3.396 |
| DPYSL3 dihydropyrimidinase-like 3 | D78014 | 3.625 |
| ribosomal protein L6 | X69391.1 | 3.807 |
| PTK9L protein tyrosine kinase 9-like (A6-related protein) | Y17169.1 | 4.143 |
| *Homo sapiens* full length insert cDNA YN88E09 | AF075050.1 | 4.257 |
| somatostatin receptor isoform 2 (SSTR2) gene | M81839.1 | 5.475 |
| CPE carboxy peptidase E | NM 001873.1 | 5.807 |
| YR-29 hypothetical protein YR-29 | AJ012409.1 | 6.333 |
| IMAGE: 4822062, mRNA | BC034811 | 6.373 |
| KIAA1832 protein, partial cds | AB058735.1 | 13.352 |
| CREG cellular repressor of E1A-stimulated genes | AF084523.1 | 2.739 |
| *Homo sapiens* putative splice factor transformer2-beta mRNA, complete cds | U61267.1 | 2.55 |
| Human N-acetyl-beta-glucosaminidase (HEXB) mRNA, 3' end | M13519.1 | 2.698 |
| Human cytochrome b5 mRNA, complete cds | M22865.1 | 2.881 |
| Human pS2 mRNA induced by estrogen from human breast cancer cell line M CF-7 | X00474.1 | 2.702 |
| Human alpha-tubulin mRNA, complete cds | K00558 | 4.655 |
| *Homo sapiens* clone 24703 beta-tubulin mRNA, complete cds | AF070561.1 | 3.917 |

Table 12 describes 21 genes highly expressed in general in the 5D tumor, including 6 ESTs/virtual proteins, and having a U value of 0 in the Mann-Whitney test. In the table, a difference in gene expression between two groups is shown as "foldchange".

in Student's t-test); (3) The result of semi-quantitative PCR was re-confirmed by independent triple experiments. 7 genes highly expressed in the 5S tumor and 3 genes highly expressed in the 5D tumor satisfied these standards for selecting a prognosis marker.

TABLE 12

(Gene group highly expressed in dead group by microarray analysis)

| Gene name and detail | Accession Number | Fold change |
| --- | --- | --- |
| Lyam-1 mRNA for leukocyte adhesion molecule-1 | X16150.1 | 7.459 |
| APM2 adipose specific 2 | NM_006829.1 | 4.853 |
| DNA polymerase gamma mRNA, nuclear gene encoding mitochondrial protein | U60325.1 | 4.269 |
| FLJ22128 fis, clone HEP19543 | AK025781 | 4.109 |
| actin related protein 2/3 complex, subunit 4, 20 kDa (RPC4) | NM_005718.2 | 4.058 |
| Scd mRNA for stearoyl-CoA desaturase | AB032261.1 | 3.794 |
| novel heterogeneous nuclear RNP protein, L protein | X16135.1 | 3.771 |
| ENSA endosulfine alpha | AF157509.1 | 3.511 |
| IMAGE: 26483 5' similar to gb: X15183_cds1 HEAT SHOCK PROTEIN HSP 90-ALPHA | R12732 | 3.086 |
| malonyl-CoA decarboxylase (MYLCD) | NM_012213 | 3.067 |
| anion exchanger 3 brain isoform (bAE3) | U05596.1 | 2.889 |
| IMAGE: 43550 3', MRNA sequence | H05914 | 2.345 |
| cDNA FLJ23636 fis, clone CAS07176. | AK074216 | 2.426 |
| IMAGE: 26366 3' similar to gb: D16234 PROBABLE PROTEIN DISULFIDE ISOMERASE ER-60 PRECURSOR | R20554 | 2.519 |
| Similar to hypothetical protein PRO2831, clone MGC: 23813 IMAGE: 4273837, mRNA, complete cds | BC017905.1 | 2.551 |
| FLJ40629 hypothetical protein FJL40629 | AK097948.1 | 2.417 |
| ribosomal protein L29 (humrp129) mRNA, complete cds | U10248.1 | 2.203 |
| EST, clone IMAGE: 745452, 3' end | AA325869 | 2.591 |
| KIAA1554 KIAA1554 protein | AB046774.1 | 2.544 |
| IMAGE: 53316 3' similar to SP: MDHC_MOUSE P14152 MALATE DEHYDROGENASE, CYTOPLASMIC | R15814 | 2.867 |
| NADH dehydrogenase (ubiquinone) 1 beta subcomplex, 3 (12 kD, B12), clone MGC: 9039 IMAGE: 3881592 | BC018183 | 4.972 |

7 genes highly expressed in the 5S group are constituted of genes encoding pro-alpha-1 type 3 collagen (PIIIP), complement component C1r, dihydropyrimidinase-like 3 (DPYSL3), proteintyrosinekinase 9-like (PTK9L), carboxy peptidase E (CPE), α-tubulin and β-tubulin. The p values in the Student's t-test of these marker genes were 0.00039, 0.0012, 0.0042, 0.036, 0.039, 0.034 and 0.00069, respectively.

3 marker genes highly expressed in the 5D group encoded heat shock protein HSP 90-alpha gene, malatedehydrogenase, and NADH dehydrogenase (ubiquinone) 1 beta subcomplex 3 (NDUFB3). The p values in the Student's t-test of these genes were 0.05, 0.0055 and 0.011, respectively.

The present inventors normalized the experiment results of semi-quantitative RT-PCR by GAPDH as an internal control and evaluated the results, verifying selection of marker genes.

Figure 7:
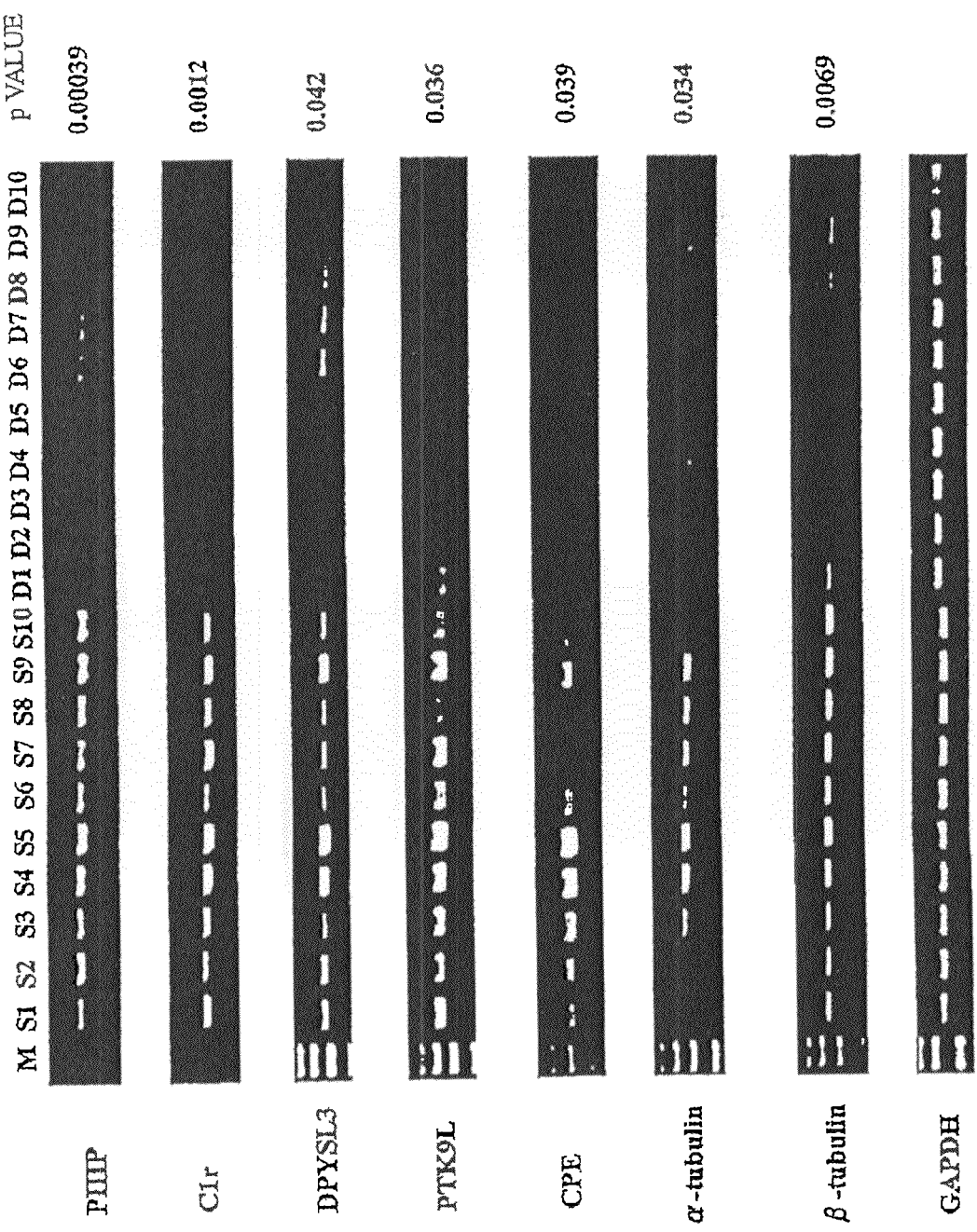
FIG. 7 is a photograph showing analysis results of semi-quantitative PCR of 7 genes highly expressed in 5S tumor.
M: marker ladder
S1-S10: newly inspected tissues of patients survived free of disease for 5 years or more after operation.
D1-D10: newly inspected cases of patients died of breast cancer within 5 years after operation.
Difference in expression strength was evaluated by Student's t-test; when p value is 0.05 or less, statistical significance is believed to be present.
Figure 8:
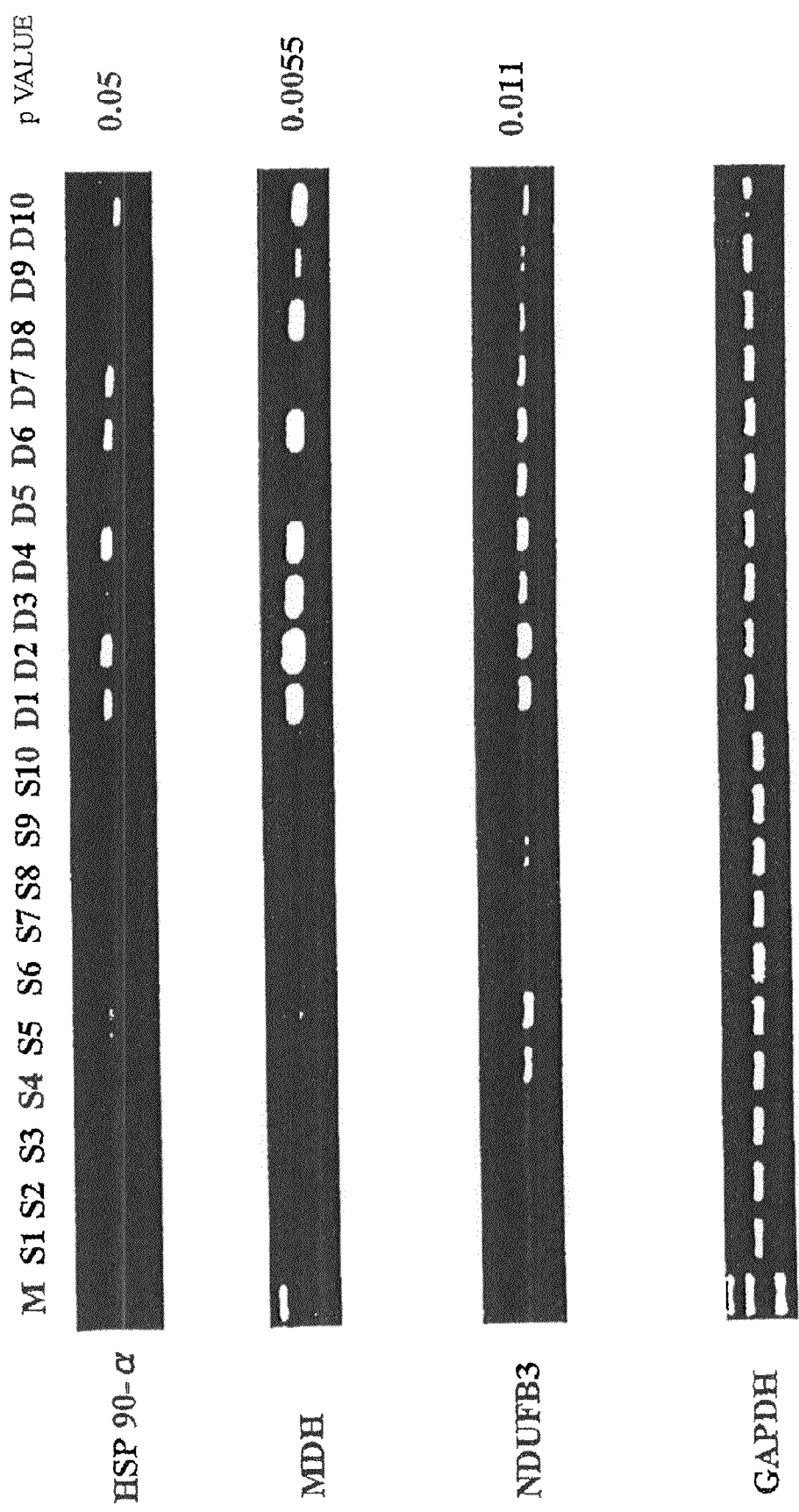
FIG. 8 is a photograph showing analysis results of semi-quantitative PCR of 3 genes highly expressed in 5D group. For explanation of marks, please see explanation in FIG. 7.

The present inventors carried out semi-quantitative PCR for checking additional 20 cases randomly selected. 10 of these patients died of breast cancer within 5 years after an operation, and remaining 10 patients survived free of disease for 5 years or more after the operation. FIG. 7 shows the results of RT-PCR of 7 marker genes highly expressed in the 5S tumor. FIG. 8 shows the results of RT-PCR of 3 marker genes highly expressed in the 5D tumor.

The present inventors defined the prognosis index (PI) as described below: (sum of normalized expression ratios of genes highly expressed in 5S group)−(sum of normalized expression ratios of genes highly expressed in 5D group). The expression ratios of the selected marker genes are summarized together with prognosis indices for further test examples in Table 13.

TABLE 13

(Expression ratio of gene and prognosis index)

| | Gene highly expressed in 5S | | | | | | | Gene highly expressed in 5D | | | | | |
|---|---|---|---|---|---|---|---|---|---|---|---|---|---|
| | PIIIP | C1r | DPYSL3 | PTK9L | CPE | A-tubulin | B-tubulin | HSP 90 | MDH | NDUFB3 | Sum of S* | Sum of D** | PI+ |
| S1 | 1.8 | 4.0 | 2.1 | 3.3 | 2.4 | 0.8 | 2.5 | 1.5 | 0.2 | 1.5 | 16.9 | 3.2 | 13.7 |
| S2 | 5.7 | 3.5 | 3.3 | 3.4 | 6.0 | 1.2 | 5.1 | 2.2 | 0.6 | 2.2 | 28.1 | 5.0 | 23.1 |
| S3 | 3.1 | 5.8 | 2.2 | 3.4 | 8.1 | 1.8 | 5.3 | 1.5 | 0.4 | 1.5 | 29.7 | 3.5 | 26.2 |
| S4 | 7.1 | 10.2 | 8.6 | 6.0 | 16.0 | 4.1 | 8.0 | 3.4 | 4.8 | 3.4 | 60.0 | 11.5 | 48.5 |
| S5 | 6.8 | 7.4 | 7.2 | 6.9 | 11.2 | 2.7 | 7.0 | 5.5 | 3.6 | 5.5 | 49.1 | 14.6 | 34.5 |
| S6 | 4.0 | 4.2 | 1.7 | 2.2 | 3.6 | 0.9 | 6.0 | 2.9 | 0.9 | 2.9 | 22.7 | 6.6 | 16.1 |
| S7 | 2.3 | 4.0 | 1.1 | 1.6 | 0.6 | 0.7 | 3.4 | 0.4 | 0.3 | 0.4 | 13.7 | 1.1 | 12.6 |
| S8 | 3.3 | 3.6 | 1.1 | 0.7 | 0.8 | 1.3 | 5.0 | 2.3 | 1.4 | 2.3 | 15.9 | 6.0 | 9.8 |
| S9 | 3.1 | 3.9 | 2.7 | 3.7 | 2.9 | 1.6 | 4.1 | 1.0 | 1.2 | 1.0 | 21.9 | 3.2 | 18.8 |
| S10 | 2.9 | 3.0 | 0.9 | 1.5 | 1.2 | 1.0 | 1.7 | 1.3 | 0.4 | 1.3 | 12.2 | 3.0 | 9.2 |
| D1 | 0.1 | 2.9 | 0.4 | 1.9 | 2.9 | 0.7 | 0.8 | 3.4 | 3.0 | 3.4 | 9.6 | 9.7 | −0.1 |
| D2 | 0.2 | 0.6 | 0.1 | 0.2 | 0.8 | 0.2 | 0.8 | 1.0 | 4.9 | 1.0 | 2.9 | 7.0 | −4.1 |
| D3 | 0.2 | 3.7 | 0.2 | 1.0 | 0.6 | 0.6 | 2.8 | 3.6 | 6.6 | 3.6 | 9.0 | 13.8 | −4.8 |
| D4 | 0.2 | 1.4 | 0.4 | 0.9 | 1.0 | 0.5 | 1.7 | 3.5 | 3.6 | 3.5 | 6.1 | 10.7 | −4.6 |
| D5 | 0.1 | 1.3 | 0.1 | 0.9 | 0.6 | 0.5 | 1.0 | 3.2 | 0.3 | 3.2 | 4.5 | 6.7 | −2.2 |
| D6 | 2.2 | 2.5 | 1.2 | 1.9 | 2.0 | 0.5 | 1.7 | 3.8 | 3.5 | 4.2 | 12.0 | 11.5 | 0.5 |
| D7 | 2.2 | 2.1 | 0.9 | 1.9 | 2.4 | 0.3 | 1.6 | 1.9 | 1.4 | 2.0 | 11.5 | 5.3 | 6.2 |
| D8 | 1.6 | 2.7 | 1.1 | 2.6 | 1.8 | 0.4 | 1.8 | 3.4 | 2.8 | 3.4 | 12.0 | 9.6 | 2.5 |
| D9 | 1.2 | 1.4 | 0.6 | 1.6 | 1.2 | 0.6 | 2.4 | 2.2 | 0.7 | 2.2 | 9.2 | 5.0 | 4.1 |
| D10 | 0.5 | 0.8 | 0.4 | 0.6 | 0.4 | 0.4 | 1.3 | 3.6 | 1.6 | 3.6 | 4.5 | 8.9 | −4.4 |

*Sum of ER of PIIP, C1r, DPYSL3, CPE, α and β-tubulin
**Sum of ER of HSP 90, MDH and NDUFP3
+PI: Sum of S − sum of D PI predicted correctly the actual clinical results of higher prognosis includes (>7) of 10 cases (S1 to S10) in total in the 5S group and prognosis indices (<7) of 10 cases (D1 to D10) in total in the 5D group. PI of the 5S group was 21.2. PI of the 5D group was −0.7. Here, by a PI value of 7 the 5S tumor and the 5D tumor were apparently distinguished (p 0.0002).

INDUSTRIAL APPLICABILITY

The postoperative prognosis prediction system of the present invention is effective for prediction of postoperative risk of a breast cancer patient. Further, the wide-range gene expression list of breast cancer correlated genes of the present invention can provide various information on progress of breast cancer, and a latent target molecule for breast cancer therapy was be predicted by the list.

The invention claimed is:

1. A method for predicting a postoperative prognosis in node-negative (n0) breast cancer with no metastasis to a lymph node in operation in a subject and treating the subject for breast cancer, the method comprising
measuring expression of a first and second set of genes in a breast cancer tissue from the subject in a DNA microarray;
normalizing the expression of the first and second set of genes relative to expression of at least one housekeeping gene in the breast cancer tissue;
calculating a prognosis score from the normalized expression of the first set of genes minus the normalized expression of the second set of genes; and
treating the subject for the node-negative (n0) breast cancer if the prognosis score is more than 3 and discontinuing treatment for the node-negative (n0) breast cancer if the prognosis score is lower than −16,
wherein the first set of genes are:
human DNA polymerase zeta catalytic subunit (REV3);
human galectin 1; and
human ribosomal protein L31, and
wherein the second set of genes are:
human ovarian beta-A-inhibin;
human proteasome (prosome, macropain) 26S subunit, non-ATPase, 3;
human MHC class I HLA-J gene,
a gene specifically amplified by a primer set of SEQ ID No. 77 and SEQ ID No. 78,
a gene specifically amplified by a primer set of SEQ ID No. 81 and SEQ ID No. 82,
a neurochondrin gene specifically amplified by a primer set of SEQ ID No. 85 and SEQ ID No. 86, and
a gene specifically amplified by a primer set of SEQ ID No. 107 and SEQ ID No. 108.

2. The method of claim 1, wherein the DNA microarray is a fiber type array.

3. The method of claim 1, wherein the measuring comprises preparing amplified RNA from the breast cancer tissue from the subject.

4. The method of claim 3, wherein the measuring further comprises hybridizing the amplified RNA to a DNA microarray comprising the first set of genes and the second set of genes.

5. The method of claim 4, wherein the amplified RNA are labeled.

6. The method of claim 5, wherein the measuring further comprises measuring hybridization between the labeled amplified RNA and the DNA on the DNA microarray.

7. The method of claim 6, wherein the measuring hybridization comprises measuring with a photometer.

8. The method of claim 1, wherein the DNA microarray is a cDNA microarray.

9. A method of treating a breast cancer patient, the method comprising
after performing an operation on the breast cancer patient, treating the patient for node-negative (n0) breast cancer with no metastasis to a lymph node, wherein the patient is selected for treatment if the patient has a poor postoperative prognosis of more than 3 determined by
measuring expression of a first and second set of genes in a breast cancer tissue from the subject in a DNA microarray;
normalizing the expression of the first and second set of genes relative to expression of at least one housekeeping gene in the breast cancer tissue;

calculating a prognosis score from the normalized expression of the first set of genes minus the normalized expression of the second set of genes; and
wherein the first set of genes are:
  human DNA polymerase zeta catalytic subunit (REV3);
  human galectin 1; and
  human ribosomal protein L31, and
wherein the second set of genes are:
  human ovarian beta-A-inhibin;
  human proteasome (prosome, macropain) 26S subunit, non-ATPase, 3;
  human MHC class I HLA-J gene,
  a gene specifically amplified by a primer set of SEQ ID No. 77 and SEQ ID No. 78,
  a gene specifically amplified by a primer set of SEQ ID No. 81 and SEQ ID No. 82,
  a neurochondrin gene specifically amplified by a primer set of SEQ ID No. 85 and SEQ ID No. 86, and
  a gene specifically amplified by a primer set of SEQ ID No. 107 and SEQ ID No. 108.

* * * * *